US009878162B2

(12) United States Patent
Mika et al.

(10) Patent No.: US 9,878,162 B2
(45) Date of Patent: *Jan. 30, 2018

(54) METHODS AND SYSTEMS FOR CONTROLLING BLOOD PRESSURE BY CONTROLLING ATRIAL PRESSURE

(71) Applicant: BackBeat Medical, Inc., New Hope, PA (US)

(72) Inventors: Yuval Mika, Closter, NJ (US); Darren Sherman, Fort Lauderdale, FL (US); Robert S. Schwartz, Inver Grove Heights, MN (US); Robert A. Van Tassel, Excelsior, MN (US); Daniel Burkhoff, Manhattan, NY (US)

(73) Assignee: BackBeat Medical, Inc., New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/372,603

(22) Filed: Dec. 8, 2016

(65) Prior Publication Data

US 2017/0080235 A1 Mar. 23, 2017

Related U.S. Application Data

(60) Continuation of application No. 14/667,931, filed on Mar. 25, 2015, now Pat. No. 9,526,900, which is a
(Continued)

(30) Foreign Application Priority Data

Dec. 19, 2013 (WO) .................. PCT/US2013/07660

(51) Int. Cl.
*A61N 1/365* (2006.01)
*A61F 2/24* (2006.01)
(Continued)

(52) U.S. Cl.
CPC ....... *A61N 1/36564* (2013.01); *A61N 1/3682* (2013.01); *A61N 1/36117* (2013.01);
(Continued)

(58) Field of Classification Search
CPC ....... A61N 1/365; A61N 1/36564; A61F 2/24; A61B 1/36
(Continued)

(56) References Cited

U.S. PATENT DOCUMENTS 3,683,934 A 8/1972 Bohdan et al.
3,814,106 A 6/1974 Berkovits
(Continued)

FOREIGN PATENT DOCUMENTS

CN 1662278 A 8/2005
CN 106029165 A 10/2016
(Continued)

OTHER PUBLICATIONS

Notice of Intention to Grant dated Jan. 3, 2017 in European Patent Application No. 13826807.3.
(Continued)

*Primary Examiner* — Carl H Layno
*Assistant Examiner* — Jon Eric C Morales
(74) *Attorney, Agent, or Firm* — Plumsea Law Group, LLC

(57) ABSTRACT

Systems and methods for controlling blood pressure by controlling atrial pressure and atrial stretch are disclosed. In some embodiments, a stimulation circuit may be configured to deliver a stimulation pulse to at least one cardiac chamber of a heart of a patient, and at least one controller may be configured to execute delivery of one or more stimulation patterns of stimulation pulses to the at least one cardiac chamber, wherein at least one of the stimulation pulses stimulates the heart such that an atrial pressure resulting
(Continued)

from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, and such that the blood pressure of the patient is reduced.

51 Claims, 21 Drawing Sheets

Related U.S. Application Data division of application No. 14/427,478, filed as application No. PCT/US2014/042777 on Jun. 17, 2014, now Pat. No. 9,370,662.

(51) Int. Cl.
    *A61N 1/36*     (2006.01)
    *A61N 1/368*     (2006.01)

(52) U.S. Cl.
    CPC ..... *A61N 1/36571* (2013.01); *A61N 1/36585* (2013.01); *A61F 2/2424* (2013.01); *A61F 2250/0013* (2013.01)

(58) Field of Classification Search
    USPC .................................................... 607/17, 23
    See application file for complete search history.

(56) References Cited

U.S. PATENT DOCUMENTS

| | | | |
|---|---|---|---|
| 3,939,844 A | 2/1976 | Pequignot | |
| 4,407,287 A | 10/1983 | Herpers | |
| 4,712,555 A | 12/1987 | Thornander et al. | |
| 4,719,921 A | 1/1988 | Chirife | |
| 4,899,752 A | 2/1990 | Cohen | |
| 5,063,239 A | 11/1991 | Schwenner et al. | |
| 5,163,429 A | 11/1992 | Cohen | |
| 5,213,098 A | 5/1993 | Bennett et al. | |
| 5,318,595 A | 6/1994 | Ferek-Petric et al. | |
| 5,584,868 A | 12/1996 | Salo et al. | |
| 5,601,613 A | 2/1997 | Florio et al. | |
| 5,601,615 A | 2/1997 | Markowitz et al. | |
| 5,612,380 A | 3/1997 | Lerner et al. | |
| 5,713,928 A | 2/1998 | Bonnet et al. | |
| 5,891,176 A | 4/1999 | Bornzin | |
| 5,928,271 A | 7/1999 | Hess et al. | |
| 6,271,015 B1 | 8/2001 | Gilula et al. | |
| 6,314,322 B1 | 11/2001 | Rosenberg | |
| 6,377,852 B1 | 4/2002 | Bornzin et al. | |
| 6,450,942 B1 | 9/2002 | Lapanashvili et al. | |
| 6,507,756 B1 | 1/2003 | Heynen et al. | |
| 6,580,946 B2 | 6/2003 | Struble | |
| 6,628,988 B2 | 9/2003 | Kramer et al. | |
| 6,666,826 B2 | 12/2003 | Salo et al. | |
| 6,668,195 B2 | 12/2003 | Warman et al. | |
| 6,699,682 B2 | 3/2004 | Gilula et al. | |
| 6,701,187 B1 | 3/2004 | Bornzin et al. | |
| 6,795,732 B2 | 9/2004 | Stadler et al. | |
| 6,832,113 B2 | 12/2004 | Belalcazar | |
| 7,001,611 B2 | 2/2006 | Kiso et al. | |
| 7,092,759 B2 | 8/2006 | Nehls et al. | |
| 7,096,064 B2 | 8/2006 | Deno et al. | |
| 7,098,233 B2 | 8/2006 | Maria et al. | |
| 7,103,410 B2 | 9/2006 | Kramer et al. | |
| 7,184,832 B2 | 2/2007 | Deno et al. | |
| 7,233,824 B2 | 6/2007 | Kleckner et al. | |
| 7,286,873 B2 | 10/2007 | Havel et al. | |
| 7,289,849 B2 | 10/2007 | Baynham et al. | |
| 7,346,394 B2 | 3/2008 | Liu et al. | |
| 7,348,173 B2 | 3/2008 | Gilula et al. | |
| 7,363,077 B1 | 4/2008 | Min et al. | |
| 7,548,782 B2 | 6/2009 | Kramer et al. | |
| 7,674,222 B2 | 3/2010 | Nikolic et al. | |
| 7,676,264 B1 | 3/2010 | Pillai et al. | |
| 7,711,420 B2 | 5/2010 | Baynham et al. | |
| 7,725,173 B2 | 5/2010 | Viertio-Oja et al. | |
| 7,725,185 B2 | 5/2010 | Liu et al. | |
| 7,765,008 B2 | 7/2010 | Ben-Haim et al. | |
| 7,869,874 B2 | 1/2011 | Levin et al. | |
| 8,027,724 B2 | 9/2011 | Wei et al. | |
| 8,046,070 B2 | 10/2011 | Salo et al. | |
| 8,086,315 B2 | 12/2011 | Schwartz et al. | |
| 8,165,674 B2 | 4/2012 | Levin et al. | |
| 8,187,160 B2 | 5/2012 | Criscione et al. | |
| 8,340,763 B2 | 12/2012 | Levin et al. | |
| 8,428,729 B2 | 4/2013 | Schwartz et al. | |
| 8,515,536 B2 | 8/2013 | Levin et al. | |
| 8,521,280 B2 | 8/2013 | Levin et al. | |
| 9,008,769 B2 | 4/2015 | Mika et al. | |
| 9,320,903 B2 | 4/2016 | Schwartz et al. | |
| 9,333,352 B2 | 5/2016 | Mika et al. | |
| 9,370,661 B2 | 6/2016 | Levin et al. | |
| 9,370,662 B2 | 6/2016 | Mika et al. | |
| 9,427,586 B2 | 8/2016 | Levin et al. | |
| 9,526,900 B2 * | 12/2016 | Mika ................. | A61N 1/36564 |
| 9,656,086 B2 | 5/2017 | Mika et al. | |
| 9,687,636 B2 | 6/2017 | Levin et al. | |
| 9,731,136 B2 | 8/2017 | Levin et al. | |
| 2002/0161410 A1 | 10/2002 | Kramer et al. | |
| 2002/0173826 A1 | 11/2002 | Lincoln et al. | |
| 2003/0060858 A1 | 3/2003 | Kieval et al. | |
| 2003/0083700 A1 | 5/2003 | Hill et al. | |
| 2003/0144702 A1 | 7/2003 | Yu et al. | |
| 2003/0144703 A1 | 7/2003 | Yu et al. | |
| 2003/0176896 A1 | 9/2003 | Lincoln et al. | |
| 2003/0199934 A1 | 10/2003 | Struble et al. | |
| 2004/0015081 A1 | 1/2004 | Kramer et al. | |
| 2004/0049235 A1 | 3/2004 | Deno et al. | |
| 2004/0138715 A1 | 7/2004 | Van Groeningen et al. | |
| 2004/0167410 A1 | 8/2004 | Hettrick | |
| 2004/0186523 A1 | 9/2004 | Florio | |
| 2004/0215255 A1 | 10/2004 | Vries | |
| 2004/0215266 A1 | 10/2004 | Struble et al. | |
| 2004/0215268 A1 | 10/2004 | Corbucci | |
| 2005/0038478 A1 | 2/2005 | Klepfer et al. | |
| 2005/0075676 A1 | 4/2005 | Deno et al. | |
| 2005/0090872 A1 | 4/2005 | Deno et al. | |
| 2005/0101998 A1 | 5/2005 | Kleckner et al. | |
| 2005/0102002 A1 | 5/2005 | Salo et al. | |
| 2005/0119285 A1 | 6/2005 | Matos et al. | |
| 2005/0149130 A1 | 7/2005 | Libbus | |
| 2005/0149131 A1 | 7/2005 | Libbus et al. | |
| 2005/0222640 A1 | 10/2005 | Schwartz et al. | |
| 2006/0173502 A1 | 8/2006 | Baynham et al. | |
| 2006/0173504 A1 | 8/2006 | Zhu et al. | |
| 2006/0247702 A1 | 11/2006 | Stegemann et al. | |
| 2007/0073352 A1 | 3/2007 | Euler et al. | |
| 2007/0083243 A1 | 4/2007 | Prakash et al. | |
| 2007/0299475 A1 | 12/2007 | Levin et al. | |
| 2007/0299477 A1 | 12/2007 | Kleckner et al. | |
| 2008/0027488 A1 | 1/2008 | Coles et al. | |
| 2008/0077187 A1 | 3/2008 | Levin et al. | |
| 2008/0109043 A1 | 5/2008 | Salo et al. | |
| 2009/0018608 A1 | 1/2009 | Schwartz et al. | |
| 2009/0036940 A1 | 2/2009 | Wei et al. | |
| 2009/0069859 A1 | 3/2009 | Whinnett et al. | |
| 2009/0082823 A1 | 3/2009 | Shuros et al. | |
| 2009/0207028 A1 | 8/2009 | Kubey et al. | |
| 2009/0240298 A1 | 9/2009 | Lian et al. | |
| 2009/0247893 A1 | 10/2009 | Lapinlampi et al. | |
| 2009/0254141 A1 | 10/2009 | Kramer et al. | |
| 2009/0281440 A1 | 11/2009 | Farazi et al. | |
| 2009/0281591 A1 | 11/2009 | Shuros et al. | |
| 2009/0318995 A1 | 12/2009 | Keel et al. | |
| 2010/0069989 A1 | 3/2010 | Shipley et al. | |
| 2010/0087889 A1 | 4/2010 | Maskara et al. | |
| 2010/0094370 A1 | 4/2010 | Levin et al. | |
| 2010/0121397 A1 | 5/2010 | Cholette | |

(56) References Cited

U.S. PATENT DOCUMENTS

| | | | |
|---|---|---|---|
| 2010/0121402 | A1 | 5/2010 | Arcot-Krishnamurthy et al. |
| 2010/0204741 | A1 | 8/2010 | Tweden et al. |
| 2011/0144712 | A1 | 6/2011 | Stahmann et al. |
| 2011/0160787 | A1 | 6/2011 | Greenhut et al. |
| 2011/0172731 | A1 | 7/2011 | Levin et al. |
| 2012/0041502 | A1 | 2/2012 | Schwartz et al. |
| 2012/0109237 | A1 | 5/2012 | Xiao et al. |
| 2012/0215272 | A1 | 8/2012 | Levin et al. |
| 2013/0331901 | A1 | 12/2013 | Levin et al. |
| 2014/0128934 | A1 | 5/2014 | Schwartz et al. |
| 2014/0163600 | A1 | 6/2014 | Levin et al. |
| 2014/0163636 | A1 | 6/2014 | Levin et al. |
| 2014/0180353 | A1 | 6/2014 | Mika et al. |
| 2016/0220824 | A1 | 8/2016 | Schwartz et al. |
| 2016/0243368 | A1 | 8/2016 | Mika et al. |
| 2016/0263383 | A1 | 9/2016 | Levin et al. |
| 2016/0339244 | A1 | 11/2016 | Levin et al. |
| 2017/0072203 | A1 | 3/2017 | Mika et al. |
| 2017/0239481 | A1 | 8/2017 | Mika et al. |
| 2017/0274190 | A1 | 9/2017 | Levin et al. |
| 2017/0291032 | A1 | 10/2017 | Levin et al. |
| 2017/0304048 | A1 | 10/2017 | Mika et al. |

FOREIGN PATENT DOCUMENTS

| | | | |
|---|---|---|---|
| CN | 104968392 | B | 11/2017 |
| EP | 2934669 | B1 | 6/2017 |
| EP | 3238777 | A2 | 11/2017 |
| JP | 2007-519441 | A | 7/2007 |
| JP | 2007-531609 | A | 11/2007 |
| JP | 2010-508979 | A | 3/2010 |
| JP | 2010-512958 | A | 4/2010 |
| JP | 2010-536481 | A | 12/2010 |
| JP | 2016-540589 | A | 12/2016 |
| WO | 9944682 | A1 | 9/1999 |
| WO | 03000252 | A1 | 1/2003 |
| WO | 2009035515 | A1 | 3/2005 |
| WO | 2005063332 | A1 | 7/2005 |
| WO | 2005097256 | A2 | 10/2005 |
| WO | 2007021258 | A1 | 2/2007 |
| WO | 2008057631 | A1 | 5/2008 |
| WO | 2008079370 | A1 | 7/2008 |
| WO | 2017044794 | A1 | 3/2017 |
| WO | 2017184912 | A2 | 10/2017 |

OTHER PUBLICATIONS

Notice of Allowance dated Jan. 18, 2017 in U.S. Appl. No. 15/143,742.
Amendment filed Jan. 19, 2017 in U.S. Appl. No. 13/960,015.
Response to Office Action filed Jan. 19, 2017 in Chinese Patent Application No. 201380072479.3, and English translation thereof.
Notice of Allowance dated Feb. 22, 2017 in U.S. Appl. No. 13/960,015.
Amendment filed Jun. 6, 2016 in U.S. Appl. No. 13/960,015.
Office Action dated Jun. 28, 2016 in U.S. Appl. No. 15/143,742.
Office Action dated Jul. 21, 2016 in U.S. Appl. No. 13/960,015.
Office Action dated Jul. 27, 2016 in U.S. Appl. No. 15/163,078.
Amendment filed Sep. 27, 2016 in U.S. Appl. No. 15/143,742.
Office Action dated Sep. 5, 2016 in Chinese Patent Application No. 201380072479.3, and English translation thereof.
Response to Office Action filed Sep. 27, 2016 in European Patent Application No. 13826807.3.
Amendment filed Oct. 26, 2016 in U.S. Appl. No. 15/163,078.
PCT Notification of Transmittal of the International Search Report and the Written Opinion of the International Searching Authority; International Search Report; and Written Opinion, dated Nov. 28, 2016 in International Application No. PCT/US2016/051023.
Arbel E.R., et al., "Successful Treatment of Drug-Resistant Atrial Tachycardia and Intractable Congestive Heart Failure with Permanent Coupled Atrial Pacing," Journal of the American College of Cardiology, 1978, vol. 41 (2), pp. 336-340.
Auricchio A., et al., "Cardiac Resyncbronization Therapy Restores Optimal Atrioventricular Mechanical Timing in Heart Failure Patients With Ventricular Conduction Delay," Journal of the American College of Cardiology, 2002, vol. 39 (7), pp. 1163-1169.
Auricchio A., et al., "Effect of Pacing Chamber and Atrioventricular Delay on Acute Systolic Function of Paced Patients With Congestive Heart Failure," Circulation—Journal of the American Heart Association, 1999, vol. 99 (23), pp. 2993-3001.
Braunwald E., et al., "Editorial: Paired Electrical Stimulation of the Heart: A Physiologic Riddle and a Clinical Challenge," Circulation, 1965, vol. 32 (5), pp. 677-681.
Calderone A., et al., "The Therapeutic Effect of Natriuretic Peptides in Heart Failure; Differential Regulation of Endothelial and Inducible Nitric Oxide Synthases," Heart Failure Reviews, 2003, vol. 8 (1), pp. 55-70.
Han B., et al., "Cardiovascular Effects of Natriuretic Peptides and Their Interrelation with Endothelin-1," Cardiovascular Drugs and Therapy, 2003, vol. 17 (1), pp. 41-52.
Information Manual, Model 5837 R-Wave Coupled Pulse Generator, Prelim. Ed. III , Medtronic, 1965, 20 pages.
PCT Notification Concerning Transmittal of International Preliminary Report on Patentability (IPER), International Application No. PCT/US2005/028415, from the International Bureau dated Feb. 21, 2008.
International Search Report and Written Opinion for Application No. PCT/US2005/28415, dated Jan. 19, 2006.
International Search Report and Written Opinion for Application No. PCT/US2014/042777, dated Jan. 2, 2015.
Invitation to Pay Additional Fees dated Oct. 17, 2014 in International Application No. PCT/US2014/042777.
Kerwin W.F., et al., "Ventricular Contraction Abnormalities in Dilated Cardiomyopathy: Effect of Biventricular Pacing to Correct Interventricular Dyssynchrony," Journal of the American College of Cardiology, 2000, vol. 35 (5), pp. 1221-1227.
Lister J.W., et al., "The Hemodynamic Effect of Slowing the Heart Rate by Paired or Coupled Stimulation of the Atria," American Heart Journal, 1967, vol. 73 (3), pp. 362-368.
Liu L., et al., "Left Ventricular Resynchronization Therapy in a Canine Model of Left Bundle Branch Block," American Journal of Physiology—Heart and Circulatory Physiology, 2002, vol. 282 (6), pp. H2238-H2244.
Lopez J.F., et al., "Reducing Heart Rate of the Dog by Electrical Stimulation," Circulation Research, 1964, vol. 15, pp. 414-429.
Nishimura K., et al., "Atrial Pacing Stimulates Secretion of Atrial Natriuretic Polypeptide without Elevation of Atrial Pressure in Awake Dogs with Experimental Complete Atrioventricular Block," Circulation Research, 1990, vol. 66 (1), pp. 115-122.
Notice of Allowance dated Dec. 16, 2014 in U.S. Appl. No. 13/826,215.
O'Cochlain B., et al., "The Effect of Variation in the Interval Between Right and Left Ventricular Activation on Paced QRS Duration," Journal of Pacing and Clinical Electrophysiology, 2001, vol. 24 (12), pp. 1780-1782.
Pappone C., et al., "Cardiac Pacing in Heart Failure Patients with Left Bundle Branch Block: Impact of Pacing Site for Optimizing Left Ventricular Resynchronization," Italian Heart Journal, 2000, vol. 1 (7), pp. 464-469.
PCT Notification of Transmittal of the International Search Report and the Written Opinion of the International Searching Authority; Declaration of Non-Establishment of International Search Report; and PCT Written Opinion of International Searching Authority, dated Apr. 24, 2014 in International Application No. PCT/US2013/076600.
Perego G.B., et al., "Simultaneous Vs. Sequential Biventricular Pacing in Dilated Cardiomyopathy: An Acute Hemodynamic Study," The European Journal of Heart Failure, 2003, vol. 5 (3), pp. 305-313.
Schoonderwoerd B.A., et al., "Atrial Natriuretic Peptides During Experimental Atrial Tachycardia: Role of Developing Tachycardiomyopathy," Journal of Cardiovascular Electrophysiology, 2004, vol. 15 (8), pp. 927-932.
Siddons et al., Cardiac Pacemakers, Pub. No. 680 of American Lecture Series, 1968, Thomas C. Publisher, pp. 200-217.

(56) References Cited

OTHER PUBLICATIONS

Verbeek X.A., et al., "Intra-Ventricular Resynchronization for Optimal Left Ventricular Function During Pacing in Experimental Left Bundle Branch Block," American Journal of Physiology—Heart and Circulatory Physiology, 2003, vol. 42 (3), pp. 558-567.
Verbeek X.A., et al., "Quantification of Interventricular Asynchrony during LBBB and Ventricular Pacing," American Journal of Physiology—Heart and Circulatory Physiology, 2002, vol. 283 (4), pp. H1370-H1378.
Whinnett Z.I., et al., "Haemodynannic Effects of Changes in Atrioventricular and Interventricular Delay in Cardiac Resynchronization Therapy Show a Consistent Pattern: Analysis of Shape, Magnitude and Relative Importance of Atrioventricular and Interventricular Delay," Heart, 2006, vol. 92 (11), pp. 1628-1634.
Willems R., et al., "Different Patterns of Angiotensin II and Atrial Natriuretic Peptide Secretion in a Sheep Model of Atrial Fibrillation," Journal of the American College of Cardiology, 2001, vol. 12 (12), pp. 1387-1392.
Zupan I., et al., "Effects of Systolic Atrial Function on Plasma Renin Activity and Natriuretic Peptide Secretion after High Rate Atrial and Ventricular Pacing in Dogs," Pacing and Clinical Electrophysiology, 2005, vol. 28 (Supp 1), pp. S270-S274.
Office Action dated Jan. 29, 2015 in U.S. Appl. No. 13/688,978.
Office Action dated May 4, 2015 in U.S. Appl. No. 13/854,283.
Office Action dated Jun. 4, 2015 in U.S. Appl. No. 13/957,499.
Office Action dated Jun. 10, 2015 in U.S. Appl. No. 13/960,015.
Office Action dated Jul. 13, 2015 in U.S. Appl. No. 14/642,952.
Office Action dated Aug. 14, 2015 in U.S. Appl. No. 13/688,978.
Amendment filed Oct. 9, 2015 in U.S. Appl. No. 14/642,952.
Amendment filed Oct. 16, 2015 in U.S. Appl. No. 14/854,281.
Amendment filed Nov. 5, 2015 in U.S. Appl. No. 13/688,978.
Office Action dated Nov. 4, 2015 in U.S. Appl. No. 14/427,478.
Amendment filed Nov. 30, 2015 in U.S. Appl. No. 13/957,499.
Amendment filed Dec. 3, 2015 in U.S. Appl. No. 13/960,015.
Notice of Allowance dated Dec. 18, 2015 in U.S. Appl. No. 13/854,283.
Notice of Allowance dated Jan. 8, 2016 in U.S. Appl. No. 14/642,952.
Amendment filed Jan. 13, 2016 in U.S. Appl. No. 14/427,478.
Final Office Action dated Jan. 20, 2016 in U.S. Appl. No. 13/960,015.
Notice of Allowance dated Feb. 12, 2016 in U.S. Appl. No. 13/688,978.
Notice of Allowance dated Feb. 12, 2016 in U.S. Appl. No. 14/427,478.
Office Action dated May 27, 2016 in European Patent Application No. 13826807.3.
Amendment filed Apr. 7, 2016 in U.S. Appl. No. 13/960,015.
Notice of Allowance dated Apr. 13, 2016 in U.S. Appl. No. 13/957,499.
Advisory Action dated Apr. 18, 2016 in U.S. Appl. No. 13/960,015.
Decision to Grant dated May 26, 2017 in European Patent Application No. 13826807.3.
Office Action dated Jun. 16, 2017 in U.S. Appl. No. 14/652,856.
Partial European Search Report dated Jul. 25, 2017 in European Patent Application No. 17169068.8.
Extended European Search Report dated Jul. 25, 2017 in European Patent Application No. 14871226.8.
Notice of Allowance dated Mar. 15, 2017 in U.S. Appl. No. 15/163,078.
Amendment filed Sep. 18, 2017 in U.S. Appl. No. 14/652,856.
Office Action dated Sep. 21, 2017 in U.S. Appl. No. 15/628,870.
Office Action dated Sep. 27, 2017 in U.S. Appl. No. 15/589,134.
Office Action dated Oct. 20, 2017 in U.S. Appl. No. 15/092,737.
Office Action dated Nov. 21, 2017 in U.S. Appl. No. 15/259,282.
Office Action dated Oct. 19, 2017 in Japanese Patent Application No. 2015-549718, and English translation thereof.
Office Action dated Nov. 6, 2017 in Australian Patent Application No. 2013361318.

\* cited by examiner

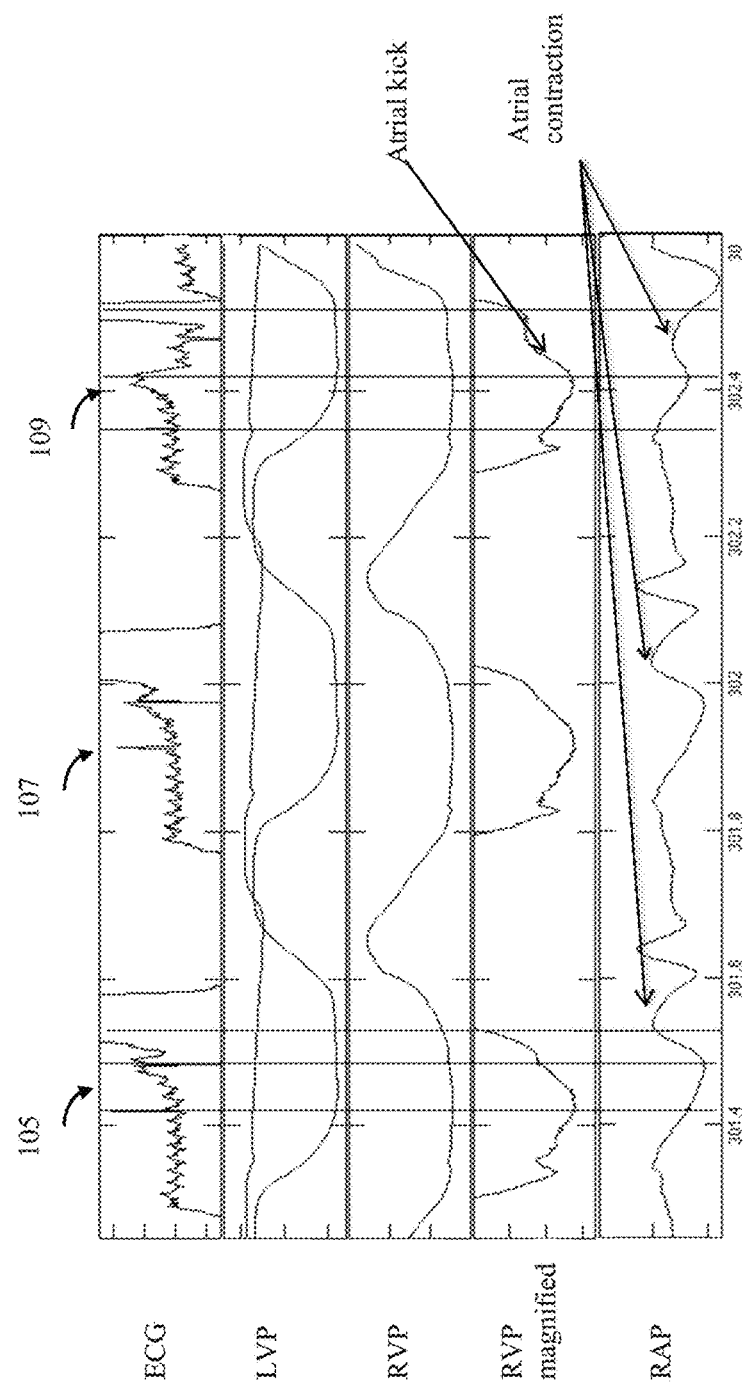

METHODS AND SYSTEMS FOR CONTROLLING BLOOD PRESSURE BY CONTROLLING ATRIAL PRESSURE

This application is a continuation of U.S. application Ser. No. 14/667,931, filed Mar. 25, 2015, now U.S. Pat. No. 9,526,900, issued Dec. 27, 2016, which is a division of U.S. application Ser. No. 14/427,478, filed Mar. 11, 2015, now U.S. Pat. No. 9,370,662, issued Jun. 21, 2016, which is a National Stage of International Application No. PCT/US2014/042777, filed Jun. 17, 2014, which claims the priority of International Application No. PCT/US2013/076600, filed Dec. 19, 2013, which claims the priority of U.S. application Ser. No. 13/826,215, filed Mar. 14, 2013, now U.S. Pat. No. 9,008,769, issued Apr. 14, 2015, the preceding two of which claim the benefit of U.S. Provisional Application No. 61/740,977, filed Dec. 21, 2012, and all of which are herein incorporated by reference in their entirety.

BACKGROUND OF THE INVENTION

1. Field of the Invention

Embodiments of the present invention relate to the field of treating hypertension through controlling cardiac functions, including filling and contractions. Specific embodiments include application of focal, electrical stimulation to the heart.

2. Description of Related Art

Variations in blood pressure are known to occur normally, due for example to increased activity (which normally elevates blood pressure) or significant blood loss (which tends to cause a reduction in blood pressure). Blood pressure is however normally maintained within a limited range due for example to the body's baroreflex, whereby elevated or decreased blood pressure affects cardiac function and the characteristics of the cardiovascular system by a feedback loop. Such feedback control is mediated by the nervous system as well as by the endocrine system (e.g., by natriuretic peptide). In hypertensive individuals, while baroreflex does function, blood pressure is maintained at an elevated level.

Hypertension, or high blood pressure (e.g., blood pressure of 140/90 mmHg or higher), is a serious health problem affecting many people. For example, approximately 74.5 million people aged 20 years and older and living in the United States have high blood pressure. Hypertension may lead to such life-threatening conditions as stroke, heart attack, and/or congestive heart failure. Approximately 44.1% of people with high blood pressure and under current treatment have satisfactory control of their hypertension. Correspondingly, 55.9% of the same people have poor control. Traditionally, treatment for hypertension has included medication and lifestyle changes. These two types of treatment are not effective for all patients. Additionally, side effects may prevent certain patients from taking medication. Accordingly, there remains a need for additional techniques for lowering blood pressure.

SUMMARY OF THE INVENTION

Methods and devices for reducing blood pressure are disclosed. Some embodiments treat hypertension mechanically instead of or in addition to treating hypertension pharmaceutically. In some embodiments, an electrical stimulator, such as a pacemaker or other type of device having a pulse generator, may be used to stimulate a patient's heart to reduce blood pressure. When the heart is stimulated in a consistent way to reduce blood pressure, the cardiovascular system may adapt to the stimulation over time and revert to a higher blood pressure. Therefore, in some embodiments, the stimulation pattern may be configured to be able to modulate the baroreflex such that the adaptation response of the cardiovascular system is reduced or even prevented.

In some embodiments, an electrical stimulator may be used to stimulate a patient's heart to cause at least a portion of an atrial contraction to occur while the atrioventricular valve is closed. Such an atrial contraction may deposit less blood into the corresponding ventricle than when the atrioventricular valve is opened during an atrial contraction, which may cause a practically immediate drop in blood pressure.

In some embodiments, an electrical stimulator may be used to stimulate a patient's heart such that an atrial pressure resulting from atrial contraction of an atrium overlaps in time a passive pressure build-up of the atrium, thereby providing an atrial pressure of the atrium that is a combination of the atrial pressure resulting from atrial contraction and the passive pressure build-up and is higher than an atrial pressure of the atrium would be without the stimulation. This may cause an increase in atrial stretch thereby reducing blood pressure through hormonal and/or neuronal pathways. This reduction in blood pressure may take some time to manifest, and its timeline would depend on the hormonal and/or neuronal pathways. The atrial pressure resulting from atrial contraction may culminate in a maximum atrial pressure resulting from atrial contraction. The passive pressure build-up of the atrium may culminate in a maximum passive pressure build-up of the atrium. Alternatively or additionally, overlapping in time an atrial pressure resulting from atrial contraction of an atrium and a passive pressure build-up of the atrium may include overlapping in time the maximum atrial pressure resulting from atrial contraction and the maximum passive pressure build-up. In some embodiments, overlapping the aforementioned maxima may result in a combined atrial pressure (of the atrial pressure resulting from atrial contraction and the passive pressure build-up) that is higher than an atrial pressure of the atrium would be without the stimulation.

In some embodiments, the electrical stimulator may be used to stimulate a patient's heart to cause within a single cardiac cycle at least a portion of an atrial contraction to occur while the atrioventricular valve is closed and/or to stimulate a patient's heart such that an atrial pressure resulting from atrial contraction of an atrium overlaps in time a passive pressure build-up of the atrium, thereby providing an atrial pressure of the atrium that is a combination of the atrial pressure resulting from atrial contraction and the passive pressure build-up and is higher than an atrial pressure of the atrium would be without the stimulation.

Some embodiments may use artificial valves in treating hypertension. In some medical conditions, where one or more of the atrioventricular (AV) valves malfunctions, the valve(s) may be replaced by implantation of artificial (prosthetic) valve(s). These artificial valves may be normally configured to passively open and close, as do natural valves, as a function of pressure differences between the atria and ventricles. Passive artificial valves are normally classified in three types based on their mechanical structure: caged ball valves, tilting disc valves, and bi-leaflet valves. As an alternative, some embodiments may use an active artificial valve that is configured to actively open and close.

In one aspect, an embodiment provides a system for reducing blood pressure in a patient having a pretreatment blood pressure. The system may comprise at least one stimulation electrode for stimulating at least one chamber of a heart of a patient with a stimulating pulse. The system may comprise at least one controller configured to execute a stimulation pattern of stimulating pulses to at least a chamber of the heart. The stimulation pattern may include a first stimulation setting and a second stimulation setting different from the first stimulation setting. At least one of the first stimulation setting and the second stimulation setting may be configured to reduce or prevent atrial kick and/or to control atrial pressure and/or stretch.

In one aspect, an embodiment provides a system for reducing blood pressure. The system may comprise at least one stimulation electrode for stimulating at least one chamber of a heart of a patient. The system may include at least one controller configured to execute a stimulation pattern comprising multiple stimulation pulses. At least one stimulation pulse of the multiple stimulation pulses may have a first stimulation setting configured to reduce atrial kick in at least one ventricle. At least one stimulation pulse of the multiple stimulation pulses may have a second stimulation setting configured to reduce the baroreflex response to the reduction in atrial kick such that the increase in blood pressure values occurring between stimulation pulses is limited to a predetermined value or range of values.

In another aspect, an embodiment provides a device for reducing blood pressure of a patient having a pretreatment blood pressure and a pretreatment ventricular filling volume. The device may comprise a stimulation circuit configured to deliver a stimulation pulse to at least one of an atrium and a ventricle. The device may comprise a processor circuit coupled to the stimulation circuit and optionally also to a sensing circuit.

In some embodiments, the device processor circuit may be configured to operate in an operating mode in which the device controls the AV delay, which, as used herein, may be taken to mean a delay occurring in a single heartbeat between ventricle excitation and/or contraction and atrial excitation and/or contraction. In addition, as used herein, the AV delay in a system or method may be taken to mean, within one heartbeat, a time delay between delivery of at least one excitatory stimulus to a ventricle and one of: the sensing of an onset of atrial excitation; the timing of an anticipated onset of atrial excitation; and the delivery of at least one excitatory stimulus to the atrium.

This AV delay may be set by delivering at least one stimulation pulse to both of at least one atrium and at least one ventricle. Optionally this stimulation is performed at a rate that is higher than the natural activity of the heart. Such rate may, for example, be set using at least one sensing electrode to sense the natural activity in the heart (e.g., in the right atrium when stimulation is not delivered) and adjusting the stimulation pulse delivery rate accordingly.

Optionally, when ventricular excitation is timed to commence before the delivery of one or more stimulation pulses to the atria, the delivery of stimulation pulses to the heart is timed such that one or more excitatory pulses are delivered to an atrium at a time that is earlier than the next anticipated natural onset of atrial excitation.

In some embodiments, the AV delay may be set by delivering at least one stimulation pulse to one or more ventricles but not to the atria. In such case, the natural activity of one or more of the atria may be sensed and the timing of ventricle excitation and/or contraction may be set to precede its natural expected timing based on the sensed atrial activity rate.

In some embodiments, the processor circuit may be configured to operate in an operating mode in which a ventricle is stimulated to cause ventricular excitation to commence between about 0 milliseconds (ms) and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. For example, the processor circuit may be configured to operate in an operating mode in which one or more excitatory pulses are delivered to a ventricle between about 0 ms and about 50 ms before a next atrial excitation is anticipated to take place. The time interval between the onset of atrial excitation and the moment that atrial excitation is sensed may be known or estimated, and used to calculate the timing of an onset of atrial excitation. For example, if it is known or estimated that atrial excitation is sensed 5 ms after the onset of atrial excitation and the ventricle is to be stimulated 20 ms before the onset of atrial excitation, then the ventricle is to be stimulated 25 ms before the next anticipated sensing of atrial excitation. In other embodiments, the processor circuit may be configured to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the processor circuit may be configured to operate in an operating mode in which one or more excitatory pulses are delivered to an atrium between about 0 ms and about 50 ms after one or more excitatory pulses are provided to the patient's ventricle. In such embodiments, the pacing may be timed without relying on sensing atrial excitation. Optionally, in such embodiments, atrial excitation is sensed in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

In some embodiments, the timing of the mechanical contraction in relation to electrical excitation of a chamber for a patient may be determined, for example, by sensing changes in atrial and ventricular pressures, sensing wall motion using ultrasound (e.g., echocardiography or cardiac echo), changes in impedance, or the opening and/or closing of a cardiac valve, using implanted and/or external sensors as known in the art. Examples for such sensors include pressure sensors, impedance, ultrasound sensors, and/or one or more audio sensors and/or one or more blood flow sensors.

The timing of the mechanical contraction in relation to electrical excitation of a chamber for a patient may be taken into account and the processor circuit may be configured accordingly, such that the one or more excitatory pulses are delivered to the heart in a timing that will generate a desired pattern of contraction. This may be performed in a closed loop mode, using one or more implanted sensors, and/or may be performed occasionally (e.g., on implantation of a device and/or during a checkup), for example, using an interface with an external measurement device.

The operating mode may include stimulating the ventricle to cause the ventricle to commence contraction before the onset of contraction of the at least one atrium.

The operating mode may include stimulating the ventricle to cause the ventricle to commence contraction before the end of contraction of the at least one atrium, thereby causing the AV valve to be closed during at least part of a contraction of the at least one atrium.

The operating mode may include stimulating the ventricle to cause the ventricle to commence contraction within less than 100 ms after the onset of contraction of the at least one atrium.

Optionally, care is taken to ensure that atrial contraction will commence before ventricle contraction has reached peak pressure. This is possible even in cases in which ventricular contraction will have commenced before the onset of atrial contraction, as atrial contraction is typically faster than ventricular contraction. Accordingly, one of the following settings may be selected:
  a. The operating mode may include stimulating the ventricle to cause the ventricle to commence contraction at any time during atrial contraction but before the atrium reaches its maximal pressure that is due to the atrial contraction.
  b. The operating mode may include stimulating the ventricle to cause the ventricle to commence contraction at any time during atrial contraction but after the atrium reaches its maximal pressure that is due to the atrial contraction.
  c. The operating mode may include stimulating the ventricle at such timing that contraction would commence in both the atrium and ventricle at essentially the same time (e.g., with no more than 5 ms from one another).
  d. The operating mode may include stimulating the ventricle to cause the ventricle to commence contraction at such timing that the peak of atrial contraction would occur when the ventricle is near or at maximal stretch, thus causing an increase in the stretch of the atrial wall, described in more detail below relative to the isovolumic phase and rapid ejection phase of the ventricle.

The operating mode may include stimulating the ventricle to cause the ventricle to contract at least partially before the onset of contraction of the at least one atrium, thereby causing the AV valve to be closed during the onset of contraction of the at least one atrium.

Optionally, the processor circuit may be configured to operate in an operating mode in which one or more excitatory pulses are delivered to an atrium between about 0 ms and about 50 ms after one or more excitatory pulses are delivered to the patient's ventricle.

In another aspect, an embodiment provides a method for reducing blood pressure of a patient having a pretreatment blood pressure and a pretreatment ventricular filling volume. The method may comprise delivering a stimulation pulse from a stimulation circuit to at least one of an atrium and a ventricle, and operating a processor circuit coupled to the stimulation circuit to operate in an operating mode in which a ventricle is stimulated to cause ventricular excitation to commence between about 0 ms and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. For example, the method may include delivering one or more excitatory pulses to a ventricle between about 0 ms and about 50 ms before a next atrial excitation is anticipated to take place. The time interval between the onset of atrial excitation and the moment that atrial excitation is sensed may be known and used to calculate the timing of the onset of atrial excitation. For example, if it is known or estimated that atrial excitation is sensed 5 ms after the onset of atrial excitation and the ventricle is to be stimulated 20 ms before the onset of atrial excitation, then the ventricle is to be stimulated 25 ms before the next anticipated sensing of atrial excitation. In other embodiments, the method may comprise operating a processor circuit coupled to the stimulation circuit to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the method may include delivering one or more excitatory pulses to an atrium between about 0 ms and about 50 ms after delivering one or more excitatory pulses to the patient's ventricle. In such embodiments, the pacing may be timed without relying on sensing atrial excitation. Optionally, such embodiments comprise sensing atrial excitation in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

In some embodiments, the timing of the mechanical contraction in relation to electrical excitation of a chamber for a patient may be evaluated using, for example, ultrasound (e.g., echocardiography or cardiac echo) or other known means. The timing of the mechanical contraction in relation to electrical excitation of a chamber for a patient may be taken into account and the timing of the delivery of the one or more excitatory pulses to the heart may be selected so as to generate a desired pattern of contraction.

The operating mode may include stimulating the ventricle to cause the ventricle to contract before the onset of contraction of the at least one atrium.

The operating mode may include stimulating the ventricle to cause the ventricle to contract before the onset of contraction of the at least one atrium, thereby causing the AV valve to be closed during at least part of a contraction of the at least one atrium.

The operating mode may include stimulating the ventricle to cause the ventricle to contract before the end of contraction of the at least one atrium, thereby causing the AV valve to be closed during the onset of contraction of at least atrium.

Optionally, the method comprises delivering one or more excitatory pulses to an atrium between about 0 ms and about 50 ms after delivering one or more excitatory pulses to the patient's ventricle.

In another aspect, an embodiment provides a device for reducing blood pressure of a patient having a pretreatment blood pressure and a pretreatment ventricular filling volume. The device may comprise a stimulation circuit configured to deliver a stimulation pulse to at least one cardiac chamber of a patient's heart. The device may comprise a processor circuit coupled to the stimulation circuit. The processor circuit may be configured to operate in an operating mode in which at least one cardiac chamber is stimulated to cause between about 40% of an atrial contraction and about 100% of an atrial contraction to occur at a time when an atrioventricular valve related to the atrium is closed, thereby reducing the ventricular filling volume from the pretreatment ventricular filling volume and reducing the patient's blood pressure from the pretreatment blood pressure. This can be achieved, for example, by causing the atrium to commence contraction about 60 ms or less before the closure of the AV valve. Optionally, this timing may be set periodically (e.g., upon implantation) based on data from an external sensor and/or as a closed loop using one or more implanted sensors.

In another aspect, an embodiment provides a device for reducing blood pressure of a patient having a pretreatment blood pressure and a pretreatment ventricular filling volume. The device may comprise a stimulation circuit configured to deliver a stimulation pulse to at least one cardiac chamber. The device may comprise a processor circuit coupled to the stimulation circuit. The processor circuit may be configured to operate in an operating mode in which at least one cardiac chamber is paced to cause about 50% to about 95% of an atrial contraction to occur during ventricular systole, thereby reducing the ventricular filling volume from the pretreatment ventricular filling volume and reducing the patient's blood pressure from the pretreatment blood pressure. This can be achieved, for example, by causing the atrium to commence contraction about 50 ms to 5 ms before commencement of ventricular contraction. Optionally, the timing of commencement of ventricular contraction may be set according to the timing of closure of an AV valve. Optionally, this timing may be set periodically (e.g., upon implantation) based on data from an external sensor and/or as a closed loop using one or more implanted sensors.

In another aspect, an embodiment provides a method, carried out with an implanted heart muscle stimulator associated with a heart of a patient, for treating a blood pressure disorder in the patient, the patient having a pretreatment blood pressure. The method may comprise stimulating a heart to cause an atrium thereof to contract while a heart valve associated with the atrium is closed such that the contraction distends the atrium, and the distending atrium results in reducing the patient's blood pressure from the pretreatment blood pressure. This can be achieved, for example, by causing the atria to contract at a time when the pressure in the ventricle is maximal so that the active force of atrial contraction will increase atrial pressure and atrial stretch above the maximal passive pressure and stretch caused by the contraction of the associated ventricle(s). In such cases, the timing of the maximal contraction of the atria should coincide with the end of the isovolumic period or during the rapid ejection period of the ventricle. Optionally, this timing may be set periodically (e.g., upon implantation) based on data from an external sensor and/or as a closed loop using one or more implanted sensors.

In another aspect, an embodiment provides a system for reducing blood pressure in a patient by controlling atrial pressure and atrial stretch. The system may include a stimulation circuit configured to deliver a stimulation pulse to at least one cardiac chamber of a heart of the patient, and at least one controller configured to execute the delivery of one or more stimulation patterns of stimulation pulses to the at least one cardiac chamber. The at least one of the stimulation pulses may stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, and such that the blood pressure of the patient is reduced.

The atrial pressure of the atrium resulting from the stimulation may cause an increased atrial stretch of the atrium that reduces blood pressure through hormonal and/or neural pathways.

The atrial pressure resulting from atrial contraction may culminate in a maximum atrial pressure resulting from atrial contraction. The passive pressure build-up of the atrium may culminate in a maximum passive pressure build-up of the atrium. Alternatively or additionally, overlapping in time an atrial pressure resulting from atrial contraction of an atrium and a passive pressure build-up of the atrium may include overlapping in time both a maximum atrial pressure resulting from atrial contraction and a maximum passive pressure build-up. In some embodiments, overlapping the aforementioned maxima may result in a combined atrial pressure (of the atrial pressure resulting from atrial contraction and the passive pressure build-up) that is higher than an atrial pressure of the atrium would be without the stimulation.

The at least one of the stimulation pulses may include stimulating the atrium of the heart. The at least one of the stimulation pulses may include stimulating a ventricle of the heart. The at least one of the stimulation pulses may also include pacing the atrium and the ventricle, optionally at a substantially equal rate, or pacing the atrium at a rate higher than a rate at which the ventricle is paced.

The at least one of the stimulation pulses may include stimulating the atrium such that the atrium contracts twice during a single cardiac cycle, for example, either by stimulation the atrium twice during a single cardiac cycle or by stimulation the atrium once during a single cardiac cycle.

Optionally, the at least one of the stimulation pulses may include stimulating the atrium such that the atrium contracts only once during a single cardiac cycle.

The at least one of the stimulation pulses may also include stimulating the heart such that atrial kick is reduced or prevented.

The one or more stimulation patterns may also include stimulating the heart such that atrial kick is reduced or prevented. The at least one of the stimulation patterns may include stimulating the heart at a plurality of heartbeats, wherein at least some of the stimulation pulses stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, and wherein at least some of the stimulation pulses are configured to reduce or prevent atrial kick.

A stimulation pulse may be provided such that in a single heartbeat both atrial kick is reduced or prevented and an atrial pressure resulting from atrial contraction of an atrium overlaps in time the passive pressure build-up of the atrium such that an atrial pressure of the atrium resulting from the stimulation is a combination of the atrial pressure resulting from atrial contraction and the passive pressure build-up and is higher than an atrial pressure of the atrium would be without the stimulation.

The at least one stimulation pattern may include at least one stimulation pulse set to have in a single heartbeat a first atrial contraction to commence when an atrioventricular valve is open and end after the atrioventricular valve is closed, and to elicit a second atrial contraction in which an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation. The first atrial contraction may be sensed and the second atrial contraction may be paced. Alternatively, the first atrial contraction and the second atrial contraction may be paced.

Alternatively, the at least one stimulation pattern may include at least one stimulation pulse set to have in a single heartbeat a first atrial contraction to commence when an atrioventricular valve is open and end before the atrioventricular valve is closed, and to elicit a second atrial contraction in which an atrial pressure resulting from atrial contraction of an atrium overlaps in time the passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation. The first atrial contraction may be sensed and the second atrial contraction may be paced. Alternatively, the first atrial contraction and the second atrial contraction may be paced.

The one or more stimulation patterns may include alternating between a plurality of stimulation patterns having a different ratio of: (1) first stimulation pulses that stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation; and (2) second stimulation pulses that stimulate the heart such that atrial kick is reduced or prevented. Optionally, the one or more stimulation patterns may include at least one stimulation pulse configured to reduce or prevent atrial kick and stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, both in a single cardiac cycle.

The one or more stimulation patterns may include alternating between a plurality of stimulation patterns having a different ratio of: (1) first stimulation pulses that stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation; and (2) second stimulation pulses that do not provide an atrial pressure resulting from atrial contraction of an atrium that overlaps in time a passive pressure build-up of the atrium.

The at least one stimulation pulse may include pacing at least one of the atrium of the heart and a ventricle of the heart such that a relative timings of excitation corresponds to an atrioventricular delay of approximately 2 ms.

The at least one stimulation pulse may include pacing at least one of the atrium of the heart and a ventricle of the heart such that a relative timing of excitation corresponds to an atrioventricular delay of between approximately 30 ms and approximately 0 ms, or even between 10 ms and 0 ms.

In another aspect, an embodiment provides a method for reducing blood pressure of a patient by controlling atrial pressure and atrial stretch. The method may be carried out with an implanted heart muscle stimulator associated with a heart of the patient. The method may include stimulating the heart to provide an atrial pressure resulting from atrial contraction that overlaps in time a passive pressure build-up of the atrium, such that the overlapping atrial pressure resulting from the atrial contraction and passive pressure build-up elicits an atrial pressure that is a combination of the atrial pressure resulting from atrial contraction and the passive pressure build-up and is higher than an atrial pressure of the atrium would be without the stimulation, and such that the blood pressure of the patient is reduced.

The atrial pressure of the atrium resulting from the stimulation may cause an increased atrial stretch of the atrium that reduces blood pressure through hormonal or neuronal pathways.

The atrial pressure resulting from atrial contraction may culminate in a maximum atrial pressure resulting from atrial contraction. The passive pressure build-up of the atrium may culminate in a maximum passive pressure build-up of the atrium. Alternatively or additionally, overlapping in time an atrial pressure resulting from atrial contraction of an atrium and a passive pressure build-up of the atrium may include overlapping in time both a maximum atrial pressure resulting from atrial contraction and a maximum passive pressure build-up. In some embodiments, overlapping the aforementioned maxima may result in a combined atrial pressure (of the atrial pressure resulting from atrial contraction and the passive pressure build-up) that is higher than an atrial pressure of the atrium would be without the stimulation. The method may therefore include stimulating the heart such that a maximum of atrial pressure resulting from atrial contraction of an atrium overlaps in time a maximum passive pressure build-up of the atrium.

The method may include stimulating the atrium of the heart. The method may include additionally or alternatively stimulating a ventricle of the heart. The method may also include pacing the atrium and the ventricle at a substantially equal rate, or pacing the atrium at a rate higher than a rate at which the ventricle is paced or contracts.

The method may further include stimulating the atrium such that the atrium contracts twice during a single cardiac cycle, for example, either by stimulating the atrium twice during a single cardiac cycle or by stimulating the atrium once during a single cardiac cycle.

Optionally, the method may include stimulating the atrium such that the atrium contracts only once during a single cardiac cycle.

The method may also include stimulating the heart such that atrial kick is reduced or prevented. Stimulating the heart may include delivering a stimulation pattern to the heart at a plurality of heartbeats, wherein at least some of the stimulation pulses in the stimulation pattern stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, and wherein at least some of the stimulation pulses are configured to reduce or prevent atrial kick. A stimulation pulse may be provided such that in a single heartbeat both atrial kick is reduced or prevented and an atrial pressure resulting from atrial contraction of an atrium overlaps in time the passive pressure build-up of the atrium such that an atrial pressure of the atrium resulting from the stimulation is a combination of the atrial pressure resulting from atrial contraction and the passive pressure build-up and is higher than an atrial pressure of the atrium would be without the stimulation.

Stimulating the heart may include delivering at least one stimulation pulse set to have in a single heartbeat a first atrial contraction to commence when an atrioventricular valve is open and end after the atrioventricular valve is closed, and to elicit a second atrial contraction in which an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation. The first atrial contraction may be sensed and the second atrial contraction may be paced. Alternatively, the first atrial contraction and the second atrial contraction may be paced.

Alternatively, stimulating the heart may include delivering at least one stimulation pulse set to have in a single heartbeat a first atrial contraction to commence when an atrioventricular valve is open and end before the atrioventricular valve is closed, and to elicit a second atrial contraction in which an atrial pressure resulting from atrial contraction of an atrium overlaps in time the passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation. The first atrial contraction may be sensed and the second atrial contraction may be paced. Alternatively, the first atrial contraction and the second atrial contraction may be paced.

The method may further include alternating between a plurality of stimulation patterns having a different ratio of: (1) first stimulation pulses that stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation; and (2) second stimulation pulses that stimulate the heart such that atrial kick is reduced or prevented. Optionally, the one or more stimulation patterns may include at least one stimulation pulse configured to reduce or prevent atrial kick and stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, both in a single cardiac cycle.

The method may further include alternating between a plurality of stimulation patterns having a different ratio of: (1) first stimulation pulses that stimulate the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation; and (2) second stimulation pulses that do not provide an atrial pressure resulting from atrial contraction of an atrium that overlaps in time a passive pressure build-up of the atrium.

The method may further include pacing at least one of the atrium of the heart and a ventricle of the heart such that a relative timing of excitation corresponds to an atrioventricular delay of approximately 2 ms.

The method may further include pacing at least one of the atrium of the heart and a ventricle of the heart such that a relative timing of excitation corresponds to an atrioventricular delay of between approximately 30 ms and approximately 0 ms.

In another aspect, an embodiment provides a method for reducing blood pressure of a patient, which may be carried out with an implanted heart muscle stimulator associated with a heart of the patient. The method may include delivering one or more stimulation patterns of stimulation pulses to at least one cardiac chamber of the heart of the patient. At least one of the stimulation pulses may have a first stimulation setting and at least one of the stimulation pulses may have a second stimulation setting different from the first stimulation setting. At least one of the first stimulation setting and the second stimulation setting may be configured to reduce or prevent atrial kick. Stimulation pulses having a stimulation setting configured to reduce or prevent atrial kick may be delivered based upon need.

Basing the delivery of stimulation pulses upon need may include one or more of the following:

a. Limiting the treatment to a time of need, for example, limiting the delivery of a stimulation setting configured to reduce or prevent atrial kick to a time when a patient's blood pressure is known to be or is expected to be abnormally high. This may include using real time feedback measurements of one or more blood pressure related parameters or basing an expected pattern of need on previous measurements taken from the same patient. For example, in some patients BP can be high 24 hours per day, while other patients may experience high BP only during a part of a 24-hour period (e.g., daytime or nighttime).

b. Preventing treatment when high BP is needed, for example, preventing the delivery of a stimulation setting configured to reduce or prevent atrial kick at such times as an increase in BP may be a healthy and thus a desired condition. For example, BP is known to increase when one is active and to reduce again when activity is reduced (e.g., when exercising or performing a physical task that is naturally associated with an increase in BP).

Stimulation pulses having a stimulation setting configured to reduce or prevent atrial kick may be provided only during part of a 24-hour period, which may be a night or part thereof, or may be a day or part thereof.

Stimulation pulses having a stimulation setting configured to reduce or prevent atrial kick may be provided only when heart rate is below a predefined threshold. The predefined threshold may be an absolute value, such as 90 bpm. The predefined threshold may be set at a value relative to the patient's average heart rate. For example, the predefined threshold may be at least one of 30 beats above average heart rate and above the $80^{th}$ percentile of the heart rate.

Stimulation pulses having a stimulation setting configured to reduce or prevent atrial kick may be provided only when the patient is at rest or at an activity level below a defined threshold. The method may further include determining whether the patient is at rest or at an activity level below a defined threshold by sensing at least one of motion, posture, respiration rate, and heart rate.

Optionally, the patient may be deemed to be "at rest" or "at a low activity level" when the patient's activity is low. For example, as long as the heart rate does not exceed a predefined threshold or only low activity is sensed (characterized, for example, by mild and/or slow motion and/or low rate of posture change and/or no significant increase in respiration, etc.), a patient may be considered "at rest" or "at a low activity level." For example, sitting activity such as while reading or talking, or motion around the house or at an office, may be deemed to be a sufficiently low activity level as to allow the delivery of stimulation pulses having a stimulation setting configured to reduce or prevent atrial kick.

The one or more stimulation patterns may be selected based on a measured blood pressure parameter. The method may further include changing the one or more stimulation patterns when baroreflex is sensed.

In another aspect, an embodiment provides a system for reducing blood pressure of a patient including a stimulation circuit configured to deliver one or more stimulation patterns of stimulation pulses to at least one cardiac chamber of the heart of the patient, and at least one controller configured to execute the delivery of the one or more stimulation patterns of stimulation pulses to the at least one cardiac chamber. At least one of the stimulation pulses may have a first stimulation setting and at least one of the stimulation pulses may have a second stimulation setting different from the first stimulation setting. At least one of the first stimulation setting and the second stimulation setting may be configured to reduce or prevent atrial kick. Stimulation pulses having a stimulation setting configured to reduce or prevent atrial kick may be delivered based upon need.

The at least one controller may be configured to deliver the stimulation pulses having a stimulation setting configured to reduce or prevent atrial kick, only during part of a 24-hour period. The part of a 24-hour period may be a night or part thereof, or may be a day or part thereof.

The at least one controller may be configured to deliver the stimulation pulses having a stimulation setting configured to reduce or prevent atrial kick, only when heart rate is below a predefined threshold. The predefined threshold may be an absolute value, such as 90 bpm. The predefined threshold may be set at a value relative to the patient's average heart rate. For example, the predefined threshold may be at least one of 30 beats above average heart rate and above the $80^{th}$ percentile of the heart rate.

The at least one controller may be configured to deliver the stimulation pulses having a stimulation setting configured to reduce or prevent atrial kick, only when the patient is at rest or at a low activity level. The system may be configured to determine whether the patient is at rest or at a low activity level by sensing at least one of motion, posture, respiration rate, and heart rate.

The at least one controller may be configured to select the one or more stimulation patterns based on a measured blood pressure parameter. The at least one controller may be configured to change the one or more stimulation patterns when baroreflex is sensed.

In another aspect, an embodiment may provide a method for adjusting a pulse setting in a system for controlling blood pressure. The method may include receiving atrial pressure data associated with an atrium of a heart of a patient during at least one cardiac cycle. The atrial pressure data may result from the system's delivering to the heart a stimulation pulse having a first pulse setting. The method may further comprise analyzing the atrial pressure data, and providing an adjusted second pulse setting according to the analysis, with the adjusted second pulse setting being different from the first pulse setting. The analyzing may include analyzing the atrial pressure data to estimate an overlap in time between an atrial pressure resulting from atrial contraction and a passive pressure build-up of the atrium. The analyzing may further include analyzing the atrial pressure data to estimate an overlap in time between a maximum atrial pressure resulting from atrial contraction and a maximum passive pressure build-up of the atrium. The analyzing may include analyzing the atrial pressure data to compare a first atrial pressure (or a maximal atrial pressure) attained in a cardiac cycle where a stimulation pulse was delivered, to a second atrial pressure of the atrium without the stimulation. The analyzing may also include plotting the atrial pressure data and/or mathematically analyzing the atrial pressure data.

In another aspect, an embodiment may provide a system for reducing blood pressure. The system may include means for providing information about pressure variation in an atrium during at least one cardiac cycle of a heart, means for generating stimulation pulses, and means for applying the stimulation pulses to at least one cardiac chamber. The means for generating stimulation pulses may be arranged to generate the stimulation pulses so as to control the timing of an atrial contraction relative to the timing of a ventricular contraction in a single cardiac cycle according to the information about pressure variation in the atrium.

The information about pressure variation in an atrium may include information about occurrence of an atrial contraction and/or information about occurrence of a ventricular contraction. The means for generating stimulation pulses may be arranged for generating for at least one cardiac cycle: at least one atrial stimulation pulse for generating an atrial contraction; and/or at least one ventricular stimulation pulse for generating a ventricular contraction. The means for generating stimulating pulses may be arranged: for generating the at least one atrial stimulation pulse, on the basis of the information about the occurrence of the atrial contraction and/or the information about the occurrence of the ventricular contraction, in a timed relationship to the occurrence of the atrial contraction and/or to the occurrence of the ventricular contraction; and/or for generating the at least one ventricular stimulation pulse on the basis of the information about the occurrence of the ventricular contraction and/or the information about the occurrence of the atrial contraction, in a timed relationship to the occurrence of the ventricular contraction and/or to the occurrence of the atrial contraction. The information about the occurrence of the atrial contraction may include information about the occurrence of a P wave pattern in the natural stimulation pattern of a cardiac cycle. The information about the occurrence of the ventricular contraction may include information about the occurrence of a QRS complex in the natural stimulation pattern of a cardiac cycle.

In another aspect, an embodiment may provide a system for reducing blood pressure. The system may include means for providing information about timing of one or more heart activity events, means for generating stimulation pulses, and means for applying the stimulation pulses to at least one cardiac chamber. The information about timing of one or more heart activity events may include at least one of: occurrence of an atrial contraction of an atrium, occurrence of a ventricular contraction of a ventricle, opening of an atrioventricular valve, closure of an atrioventricular valve, electrical activity of the atria, electrical activity of the ventricle, blood flow, atrial pressure of the atrium, changes in atrial pressure of the atrium, and heart rate. The means for generating stimulation pulses may be arranged to generate the stimulation pulses so as to set a timing of atrial contraction relative to ventricular contraction based on the information.

The timing of atrial contraction relative to ventricular contraction may correspond to an AV delay within a range of about 30 ms to about 0 ms. The means for generating stimulation pulses may be arranged to generate the stimulation pulses so as to: provide an excitatory stimulus to the atrium within a range of about 30 ms to about 0 ms before ventricular excitation occurs; provide an excitatory stimulus to the ventricle within a range of about 30 ms to about 0 ms after atrial excitation occurs; and/or provide an excitatory stimulus to the atrium and then within a range of about 30 ms to about 0 ms later provide an excitatory stimulus to the ventricle.

The information about timing of one or more heart activity events may include information about timing between two or more heart activity events in a single cardiac cycle.

The means for generating stimulation pulses may be arranged for generating for at least one cardiac cycle: at least one atrial stimulation pulse for generating an atrial contraction; and/or at least one ventricular stimulation pulse for generating a ventricular contraction. The means for generating stimulating pulses may be arranged: for generating the at least one atrial stimulation pulse, on the basis of the information about the occurrence of the atrial contraction and/or the information about the occurrence of the ventricular contraction, in a timed relationship to the occurrence of the atrial contraction and/or to the occurrence of the ventricular contraction; and/or for generating the at least one ventricular stimulation pulse on the basis of the information about the occurrence of the ventricular contraction and/or the information about the occurrence of the atrial contraction, in a timed relationship to the occurrence of the ventricular contraction and/or to the occurrence of the atrial contraction. The information about the occurrence of the atrial contraction may include information about the occurrence of a P wave pattern in the natural stimulation pattern of a cardiac cycle. The information about the occurrence of the ventricular contraction may include information about the occurrence of a QRS complex in the natural stimulation pattern of a cardiac cycle.

In another aspect, an embodiment provides another method for reducing blood pressure of a patient by controlling atrial pressure and atrial stretch. The method may be carried out with an implanted heart muscle stimulator associated with a heart of the patient. The method may include delivering one or more stimulation patterns of stimulation pulses to at least one cardiac chamber, wherein at least one of the stimulation pulses has a first stimulation setting and at least one of the stimulation pulses has a second stimulation setting different from the first stimulation setting, at least one of the first stimulation setting and the second stimulation setting being configured to have an atrium contract such that an atrial pressure resulting from atrial contraction of an atrium overlaps in time a passive pressure build-up of the atrium; and providing, through the overlapping atrial pressure resulting from atrial contraction and passive pressure build-up, an atrial pressure of the atrium that is a combination of the atrial pressure resulting from atrial contraction and the passive pressure build-up and is higher than an atrial pressure of the atrium would be without the stimulation, thereby causing increased atrial stretch of the atrium that reduces blood pressure through hormonal or neuronal pathways. Optionally, at least one of the first stimulation setting and the second stimulation setting may be configured to have an atrium contract such that a maximum atrial pressure resulting from atrial contraction overlaps in time a maximum passive pressure build-up in the atrium, and the method may include providing, through the overlapping maximum atrial pressure resulting from atrial contraction and maximum passive pressure build-up, an atrial pressure of the atrium that is higher than an atrial pressure of the atrium would be without the stimulation, thereby causing increased atrial stretch of the atrium that reduces blood pressure through hormonal or neuronal pathways.

In another aspect, an embodiment provides a system for reducing blood pressure of a patient by controlling atrial pressure and atrial stretch. The system may include a stimulation circuit configured to deliver one or more stimulation patterns of stimulation pulses to at least one cardiac chamber, and at least one controller configured to execute delivery of one or more stimulation patterns of stimulation pulses to at least one cardiac chamber. At least one of the stimulation pulses may have a first stimulation setting and at least one of the stimulation pulses may have a second stimulation setting different from the first stimulation setting. At least one of the first stimulation setting and the second stimulation setting may be configured to have an atrium of the heart contract such that an atrial pressure resulting from atrial contraction of an atrium overlaps in time a passive pressure build-up of the atrium, thereby providing an atrial pressure of the atrium that is a combination of the atrial pressure resulting from atrial contraction and the passive pressure build-up and is higher than an atrial pressure of the atrium would be without the stimulation, thereby causing increased atrial stretch of the atrium that reduces blood pressure through hormonal or neuronal pathways. Optionally, at least one of the first stimulation setting and the second stimulation setting may be configured to have an atrium of the heart contract such that a maximum atrial pressure resulting from atrial contraction overlaps in time a maximum passive pressure build-up in the atrium, thereby providing an atrial pressure of the atrium that is higher than an atrial pressure of the atrium would be without the stimulation, and causing increased atrial stretch of the atrium that reduces blood pressure through hormonal or neuronal pathways.

In another aspect, an embodiment provides a method for treating a blood pressure disorder in a patient by controlling atrial pressure and atrial stretch. The method may be carried out with an implanted heart muscle stimulator associated with a heart of the patient, with the patient having a pretreatment blood pressure. The method may include stimulating the heart to have an atrium thereof contract while a heart valve associated with the atrium is closed such that the contraction distends the atrium, and the distending atrium results in reducing the patient's blood pressure from the pretreatment blood pressure, preferably by causing the atrium to contract at a time when pressure in a ventricle is maximal so that active force of atrial contraction increases atrial pressure and stretch above maximal passive pressure and stretch caused by contraction of the ventricle.

In another aspect, an embodiment provides a system for reducing blood pressure. The system may comprise at least one stimulation electrode for stimulating at least one chamber of a heart of a patient with a stimulation pattern comprising at least one stimulation pulse. The system may include at least one controller configured to receive input relating to the patient's blood pressure and adjust the stimulation pattern based on said blood pressure. For example, the input may include receiving data sensed by one or more sensors (implanted or external) and/or receiving data provided by a user. For example, during implantation and/or periodic checks, a user may provide data regarding measured blood pressure. Optionally, the system includes an input port for receiving this input by wired and/or wireless communication from a measuring sensor and/or a user interface. The input may comprise data relating to blood pressure (BP) or a change in BP, which may be measured as systolic BP (SysBP), diastolic BP, mean arterial BP, and/or any other related BP parameter. For example, at least one sensor may sense the pressure or changes of pressure in one or more cardiac chambers and adjust the stimulation pattern based on the pressure or changes in pressure. In another embodiment, the sensor may sense the pressure in more than one chamber and adjust the stimulation based on the relation between the pressure waveforms of the two chambers.

The controller may be configured to adjust the stimulation pattern by performing an adjustment process that includes adjusting a parameter of a first stimulation setting of at least one of the at least one stimulation pulse.

The first stimulation setting may be configured to reduce or prevent atrial kick in at least one ventricle.

The parameter may include the adjustment of the AV delay. For example, a natural AV delay may be a range of 120 to 200 ms between the onset of atrial excitation and the onset of ventricular excitation, whether occurring naturally (i.e., without the delivery of a stimulus to the heart) or by setting the timing of the delivery of stimuli to one or more of the atrium and ventricle. Optionally, adjusting the AV delay means adjusting it from a normal AV delay (of, for example, 120 ms) to a shorter AV delay (for example, 0 to 70 ms from the onset of atrial excitation to onset of ventricular excitation; or an AV delay of 0 to −50 ms in which the ventricular excitation occurs before atrial excitation). In an embodiment, a stimulation setting having an AV delay of between −50 ms to 70 ms, preferably −40 ms to 60 ms, more preferably −50 ms to 0 or 0 to 70 ms, preferably >0 to 70 ms, is chosen to reduce or prevent atrial kick.

The stimulation pattern that is configured to reduce atrial kick may be configured to cause a reduction in blood pressure by at least a predetermined amount within about 3 sec from an application of electricity to the heart, and to maintain a reduction in blood pressure for a time interval of at least 1 minute. For example, a stimulation pattern may be selected and/or adjusted based on feedback relating to one or more sensed BP parameters.

The time interval may be at least 5 minutes.

The predetermined amount of blood pressure reduction may be 8 mmHg or more.

The predetermined amount of blood pressure reduction may be at least 4% of the patient's pretreatment blood pressure.

The patient's blood pressure may not exceed a predetermined average value during the time interval by more than a predetermined degree. The predetermined degree may be a difference of about 8 mmHg or less. In some embodiments, a patient's blood pressure may exceed a predetermined average value for some heartbeats, but the patient's average blood pressure may not exceed the predetermined average value.

The controller may be configured to execute a plurality of stimulation patterns and receive for each of the stimulation patterns a corresponding input data relating to the patient's blood pressure during the stimulation. The controller may be configured to calculate for each of the plurality of stimulation patterns at least one blood pressure variation parameter relating to the input data. The controller may be configured to adjust the stimulation pattern according to the blood pressure variation parameter.

The controller may be configured to adjust the stimulation pattern to be the one with the best blood pressure variation parameter.

The best blood pressure variation parameter may be one that displays the lowest degree of baroreflex, or the lowest degree or rate of adaptation as detailed herein.

The best blood pressure variation parameter may be one that displays a baroreflex or degree of adaptation within a predetermined range as detailed herein.

The at least two stimulation patterns of the plurality of stimulation patterns may each comprise at least one stimulation pulse having a stimulation setting configured to reduce or prevent atrial kick in at least one ventricle and/or to control atrial pressure and/or stretch. The at least two stimulation patterns may differ one from another by the number of times or the length of time the at least one stimulation pulse is provided in sequence.

The plurality of stimulation patterns may differ by the number of times or the length of time that the system is configured to elicit a predetermined AV delay in sequence.

The at least two stimulation patterns of the plurality of stimulation patterns may differ from another by one or more stimulation settings included within each of the at least two stimulation patterns.

The plurality of stimulation patterns may include a first stimulation pattern and a second stimulation pattern executed after the first stimulation pattern. The second stimulation pattern may have at least one stimulation setting that was set based on an algorithm using blood pressure variation parameters relating to the input data of the first stimulation pattern.

The system may comprise a blood pressure sensor for providing the input data relating to the patient's blood pressure.

The blood pressure sensor may be implantable.

The blood pressure sensor and the controller may be configured to operate at least partially as a closed loop.

In another aspect, an embodiment provides a system for reducing blood pressure. The system may comprise at least one stimulation electrode for stimulating at least one chamber of a heart of a patient with a stimulation pulse. The system may comprise a controller. The controller may be configured to provide a first stimulation pattern comprising at least one stimulation setting configured to reduce or prevent atrial kick in at least one ventricle for a first time interval and to receive a first input data relating to a patient's blood pressure during said first time interval. The controller may be configured to calculate at least one blood pressure variation parameter relating to the first input data. The controller may be configured to adjust at least one parameter of a second stimulation pattern comprising a second stimulation setting configured to reduce or prevent atrial kick in at least one ventricle. The second stimulation setting may be based upon the at least one blood pressure variation parameter. The controller may be configured to provide the second stimulation pattern for a second time interval.

In another aspect, an embodiment may provide a system for reducing blood pressure. The system may comprise at least one stimulation electrode for stimulating at least one chamber of a heart of a patient with a stimulation pulse. The system may comprise at least one controller configured to execute a stimulation pattern comprising at least one stimulation setting configured to reduce or prevent atrial kick in at least one ventricle. The stimulation pattern may be selected to cause an immediate reduction in blood pressure from an initial pressure value to a reduced pressure value and to maintain a patient's average blood pressure at rest at least 8 mmHg below the initial pressure.

The reduced blood pressure value may be maintained for a time interval of at least 1 minute.

In another aspect, an embodiment provides a kit for reducing blood pressure. The kit may comprise at least one device for setting a stimulation pattern for reducing blood pressure. The device may comprise at least one stimulation electrode. The device may comprise a controller for setting an adjustable stimulation pattern and a set of instructions for adjusting the stimulation pattern based on input relating to patient blood pressure.

In another aspect, an embodiment provides a system for reducing blood pressure. The system may comprise at least one stimulation electrode for stimulating at least one chamber of a heart of a patient. The system may comprise at least one controller configured to execute a stimulation pattern comprising at least one stimulation pulse having at least one stimulation setting configured to reduce or prevent atrial kick in at least one ventricle. The at least one stimulation setting may be configured such that maximum atrial stretch is at a value that is about equal to or lower than the maximum atrial stretch of the same heart when not receiving stimulation.

In any of the embodiments described herein, atrial stretch may be measured, calculated, and/or estimated as known in the art. Atrium contraction is known to affect atrial pressure and atrial stretch. The pressure and the stretch of an atrium depend on atrial volume, which depends on the amount of blood inside the atrium and the active force generated by the contraction of the muscle. In a healthy heart, as the atrium contracts, atrial pressure builds up. Atrial pressure drops when atrial contraction stops and blood is flowing out of the atrium to fill the ventricle. Then, when the ventricles contract, the AV valve closes and the atrium starts to fill again, since there is no valve that prevents the flow of blood from the venous system to the atrium. Pressure generated in the ventricle also increases atrial pressure via various mechanisms, one of which relates to the bulging of the AV valve into the atria. An increase in atrial pressure that occurs against a closed AV valve will also increase atrial stretch that relates to atrial volume and atrial pressure. The contraction of the atrium when the AV valve is closed increases both atrial pressure and atrial stretch since the closed valve prevents reduction in volume. An increase in stretch in the atrium stimulates baroreceptors (also known as stretch receptors) present in the atrium wall. These baroreceptors are involved in hormonal and/or neuronal reduction of blood pressure. Accordingly, in some embodiments, atrial stretch determination may include measuring atrial pressure. In some embodiments, atrial stretch determination may include measuring or estimating the dimension of an atrium (e.g., diameter, size, or circumference). In some cases, when a single atrial contraction occurs per cardiac cycle, the amount of blood in the atrium is expected to be larger than when the atrium contracts twice during a single cardiac cycle. Thus, if atrial contraction is performed once per cardiac cycle, and atrial contraction is fully against a closed valve, atrial pressure and/or atrial stretch may be higher than in cases when the atrium contracts twice per cycle. However, when the atrium contracts only against a closed valve there is also no atrial kick, and in some embodiments a balance may be struck (per cardiac cycle and/or per pacing pattern) between values set for atrial pressure (and atrial stretch) and atrial kick.

The at least one stimulation setting may be configured to cause an atrium to be at maximum contraction when the AV valve is open.

The at least one stimulation setting may be configured to alter the mechanics of at least one atrial contraction such that the mechanics of the at least one atrial contraction are different from the mechanics of a previous natural atrial contraction. The mechanics of atrial contraction may be assessed using any known technique including, for example, ultrasound (e.g., echocardiography or cardiac echo).

The at least one stimulation setting may be configured to reduce the force of at least one atrial contraction. The force of atrial contraction may be reduced, for example, by temporarily generating atrial spasm or atrial flutter. One example is the delivery of a burst of rapid stimulation pulses to the atrium for a short period of predefined time. The force of atrial contraction can be calculated from sensing of atrial pressure and/or a derivative thereof such as wall motion or flow using any known means. Such sensing may be used as a feedback in a closed loop and/or occasionally (e.g., upon implantation and/or checkups).

The at least one stimulation setting may be configured to prevent at least one atrial contraction. Atrial contraction may be prevented, for example, by temporarily generating atrial spasm or atrial flutter. One example is the delivery of a burst of rapid stimulation pulses to the atrium for a short period of predefined time.

In another aspect, an embodiment provides a system for reducing blood pressure. The system may comprise at least one stimulation electrode for stimulating at least one chamber of a heart of a patient. The at least one controller may be configured to execute a stimulation pattern of stimulation pulses to the heart of a patient. The at least one controller may be configured to receive input relating to the patient's AV valve status. This input may be provided by wired or wireless communication from an implanted or external acoustic sensor or blood flow sensor and/or via a user interface. The at least one controller may be configured to adjust the at least one stimulation pattern based on said valve status.

The input relating to the patient's AV valve status may be indicative of the timing of closure of the AV valve.

The input relating to the patient's AV valve status may be provided based on a heart sound sensor.

The input relating to the patient's AV valve status may be provided based on a blood flow sensor.

The blood flow sensor may include an implanted sensor.

The blood flow sensor may include an ultrasound sensor for sensing blood flow through the AV valve.

The blood flow sensor and the controller may be configured to operate at least partially as a closed loop.

The stimulation pattern may comprise at least one stimulation pulse configured to reduce or prevent the atrial kick in at least one ventricle.

The step of adjusting the at least one stimulation pattern may include adjusting the AV delay of at least one stimulation pulse.

In another aspect, an embodiment provides a system for reducing ventricular filling volume in a patient having a pretreatment ventricular filling volume. The system may comprise a stimulation circuit configured to deliver a stimulation pulse to at least one cardiac chamber. The system may comprise at least one controller configured to execute the delivery of one or more stimulation patterns of stimulation pulses to at least one cardiac chamber. At least one of the stimulation pulses may have a first stimulation setting and at least one of the stimulation pulses may have a second stimulation setting different from the first stimulation setting. At least one of the first stimulation setting and the second stimulation setting may be configured to reduce or prevent atrial kick, thereby reducing the ventricular filling volume from the pretreatment ventricular filling volume.

The first stimulation setting and the second stimulation setting may be configured to reduce or prevent atrial kick.

The first stimulation setting may have a different AV delay than the AV delay of the second stimulation setting.

At least one of the one or more stimulation patterns may be repeated at least twice in a period of one hour.

The at least one controller may be configured to execute the one or more stimulation patterns consecutively for a time interval lasting 10 minutes or longer. The first stimulation setting may be configured to reduce or prevent atrial kick in at least one ventricle for at least 50% of the time interval.

The second stimulation setting may have a longer AV delay than the first stimulation setting.

The second stimulation setting has a longer AV delay than the first stimulation setting.

The one or more consecutive stimulation patterns may comprise at least one stimulation pulse having the first stimulation setting for at least about 85% of the time interval.

The time interval may be at least 30 minutes long.

The time interval may be at least one hour long.

The time interval may be at least 24 hours long.

The one or more consecutive stimulation patterns may comprise at least one stimulation pulse having a third stimulation setting different from the first stimulation setting and the second stimulation setting and configured to reduce or prevent atrial kick in at least one ventricle.

The one or more consecutive stimulation patterns may comprise at least one stimulation pulse having a third stimulation setting different from the first stimulation setting and the second stimulation setting and configured not to reduce or prevent atrial kick in at least one ventricle for less than about 50% of the time interval.

The one or more consecutive stimulation patterns may comprise a third stimulation configured not to reduce or prevent atrial kick in at least one ventricle for about 20% or less of the time interval.

The one or more stimulation patterns may comprise a sequence of 10-60 stimulation pulses having the first stimulation setting. The first stimulation setting may be configured to reduce or prevent atrial kick in at least one ventricle, and a sequence of 1-10 heartbeats embedded within the 10-60 stimulation pulses. The sequence of 1-10 heartbeats may have a longer AV delay than the first stimulation setting.

The sequence of 1-10 heartbeats may include at least one stimulation pulse having a first stimulation setting configured to reduce or prevent atrial kick in at least one ventricle.

The sequence of 1-10 heartbeats may include at least one stimulation pulse having a second stimulation setting.

The sequence of 1-10 heartbeats may include a natural AV delay.

At least one heartbeat of the sequence of 1-10 heartbeats may occur without stimulation.

The first stimulation setting may be configured to reduce atrial kick in at least one ventricle and the second stimulation setting may be configured to reduce the baroreflex response or adaptation to the reduction in atrial kick such that the increase in blood pressure values occurring between stimulation pulses is limited to a predetermined value.

The second stimulation setting may be configured to allow an increase in blood pressure for about 1 heartbeat to 5 heartbeats.

The stimulation pattern may include multiple stimulation pulses having the first stimulation setting.

The stimulation pattern may include multiple stimulation pulses having the second stimulation setting.

Between about 1% of the multiple stimulation pulses and 40% of the multiple stimulation pulses of the stimulation pattern may have the second stimulation setting.

The stimulation pattern may include a ratio of stimulation pulses having the first stimulation setting to the stimulation pulses having the second stimulation setting that corresponds to a ratio of time constants of a response to increase and decrease in blood pressure.

The first stimulation setting may include a first AV delay and the second stimulation setting may include a second AV delay. The first AV delay may be shorter than the second AV delay.

The stimulation pattern may include multiple stimulation pulses having the first stimulation setting.

The stimulation pattern may include multiple stimulation pulses having the second stimulation setting.

Between about 1% of the multiple stimulation pulses and 40% of the multiple stimulation pulses of the stimulation pattern may have the second stimulation setting.

The stimulation pattern may include a ratio of stimulation pulses having the first stimulation setting to the stimulation pulses having the second stimulation setting that corresponds to a ratio of time constants of the response to increase and decrease in blood pressure.

The stimulation pattern may include a ratio of about 8 to about 13 stimulation pulses having the first stimulation setting to about 2 to about 5 the stimulation pulses having the second stimulation setting.

One of the first stimulation setting and the second stimulation setting may be configured to invoke a hormonal response from the patient's body.

In another aspect, an embodiment provides a system for reducing ventricular filling volume of a patient having a pretreatment ventricular filling volume. The system may comprise a stimulation circuit configured to deliver a stimulation pulse to at least one cardiac chamber. The system may comprise at least one controller configured to execute the delivery of one or more stimulation patterns of stimulation pulses to at least one cardiac chamber. At least one of the stimulation pulses may include a setting configured to cause a ventricular excitation to commence between about 0 ms and about 70 ms after the onset of atrial excitation, thereby reducing the ventricular filling volume from the pretreatment ventricular filling volume. For example, the processor circuit may be configured to operate in an operating mode in which one or more excitatory pulses are delivered to the ventricle between about 0 ms and about 70 ms after the onset of atrial excitation in at least one atrium occurs, or between about 0 ms and about 70 ms after one or more excitatory pulses are delivered to the atrium.

In some embodiments, the timing of a sensed atrial excitation may be determined by taking into account a delay between actual onset of excitation and the sensing thereof. For example, if a sensing delay is estimated to be 20-40 ms, and stimulation pulses are to be delivered 0-70 ms after onset of atrial excitation, a system may be set to deliver pulses between 40 ms before the next anticipated sensing event to 30 ms after the next anticipated sensing event or 30 ms after the next sensing event. Likewise, if the stimulation pulses are to be delivered to the ventricle 0-50 ms before onset of atrial excitation, assuming the same 20-40 ms sensing delay, a system may be set to deliver pulses between 40 ms before the next anticipated sensing event to 90 ms before the next anticipated sensing event. Sensing delays may be due to one or more of a distance between the site of onset of excitation and a sensing electrode, the level of the electrical signal, characteristics of the sensing circuit, and the threshold set of a sensing event. The delay may include, for example, the duration of the signal propagation from the origin of excitation to the electrode location, the duration related to the frequency response of the sensing circuit, and/or the duration necessary for the signal propagation energy to reach a level detectable by a sensing circuit. The delay may be significant and can range, for example, between about 5 ms to about 100 ms. One approach for estimating the delay is to use the time difference between an AV delay measured when both atrium and ventricle are sensed and the AV delay when the atrium is paced and the ventricle is sensed. Other approaches may use calculation of the amplifier response time based on the set threshold, signal strength, and frequency content. Other approaches may include modifying the delay used with atrial sensing until the effect on blood pressure is the same as the effect obtained by pacing both atrium and ventricle with the desired AV delay.

In another aspect, a system is provided for reducing ventricular filling volume in a patient having a pretreatment ventricular filling volume. The system may include a stimulation circuit configured to deliver a stimulation pulse to at least one cardiac chamber. At least one controller may be configured to execute the delivery of one or more stimulation patterns of stimulation pulses to at least one cardiac chamber for a time interval lasting 10 minutes or longer. At least one of the stimulation pulses may have a first stimulation setting configured to reduce or prevent atrial kick in at least one ventricle for at least 5 minutes of the time interval and at least one of the stimulation pulses has a second stimulation setting different from the first stimulation setting, thereby reducing the ventricular filling volume from the pretreatment ventricular filling volume.

In another aspect, a method is provided for reducing ventricular filling in a patient having a pretreatment ventricular filling volume. The method may include a step of delivering one or more stimulation patterns of stimulation pulses to at least one cardiac chamber for a time interval lasting 10 minutes or longer. At least one of the stimulation pulses may have a first stimulation setting configured to reduce or prevent atrial kick in at least one ventricle for at least 5 minutes of the time interval and at least one of the stimulation pulses has a second stimulation setting different from the first stimulation setting.

Other systems, methods, features, and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 12 shows a right atria pressure, magnified diastolic portion of right ventricular pressure, right ventricular pressure, left ventricular pressure and at the same graph aortic pressure and an electrocardiogram of a hypertensive canine heart;

DETAILED DESCRIPTION

The human heart comprises two atria and two ventricles. In a normal heart cycle, cardiac contraction begins with atrial contraction, which is followed by contraction of the ventricles.

The mechanical process of cardiac contraction is controlled by conduction of electricity in the heart. During each heartbeat, a wave of depolarization is triggered by cells in the sinoatrial node. The depolarization propagates in the atria to the atrioventricular (AV) node and then to the ventricles. In a healthy heart, atrioventricular delay (AV delay), i.e., the delay time between the onset of atrial excitation and the onset of ventricular excitation, is normally between 120 milliseconds (ms) and 200 ms. The relative timing of the atrial contraction and the ventricular contraction is affected inter alia by the relative timing of excitation of each chamber and by the time needed by the chamber to generate mechanical contraction as a result of the electrical activation (depending on size, speed of propagation, differences in myocyte properties, etc.).

Before contraction, the heart muscle is relaxed and blood flows freely into the ventricles from the atria, through a valve between them. This period can be divided into a rapid filling phase and a slow filling phase. The rapid filling phase commences just after the relaxation of the ventricle, during which blood from the venous system and the atria rapidly fills the ventricle. The rapid filling phase lasts for approximately 110 ms and is followed by the slow filling phase, which lasts until the start of the contraction of the atria. The duration of the slow filling phase depends on the heart rate. Thereafter, as an atrium contracts, pressure increases in the atrium and causes blood to flow more rapidly into the ventricle. This contribution of atrial contraction to ventricle filling is known as the "atrial kick." Atrial kick is normally responsible for about 10%-30% of ventricle filling.

Figure 17:
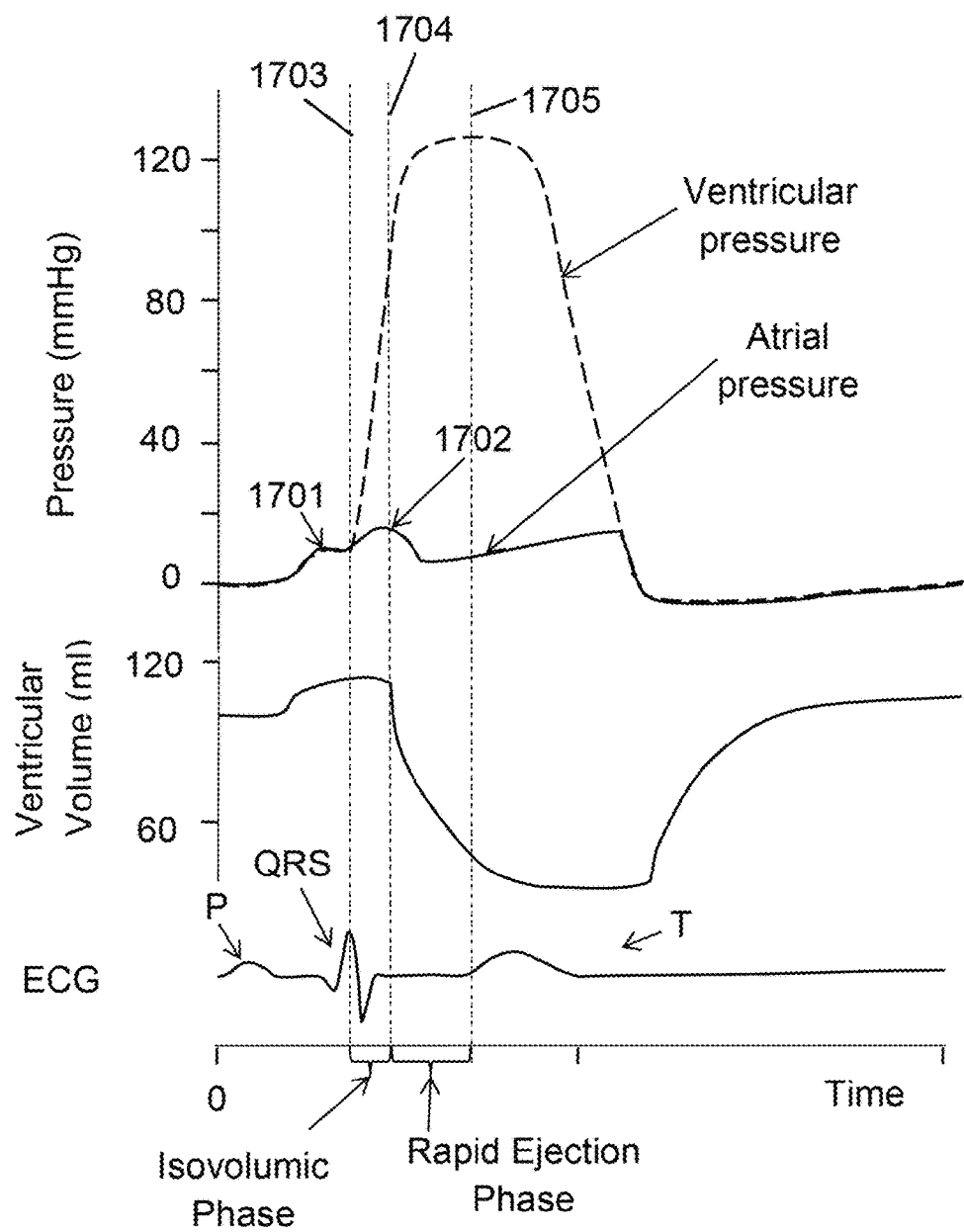
FIG. 17 is a graph showing ventricular volume, ventricular pressure, atrial pressure, and electrocardiogram (ECG) plotted against time, highlighting the isovolumic phase and rapid ejection phase of a single cardiac cycle.

FIG. 17 illustrates changes in ventricular volume, ventricular pressure, atrial pressure, and cardiac electrical activity over time through a single cardiac cycle. As used herein, a cardiac cycle is a period of time between two relaxations of the ventricle, between which only a single contraction of the ventricle takes place. The duration of the cardiac cycle is inversely proportional to the heart rate, such that the cardiac cycle duration increases as the heart rate decreases and decreases as the heart rate increases. At a typical human rate of 75 beats per minute, one cardiac cycle lasts about 0.8 seconds.

Referring to FIG. 17, a cardiac cycle may be said to begin at the onset of atrial excitation, when a P wave is observed in the ECG. Then, about 50-70 ms thereafter the atrium begins to contract, for a period of about 70-110 ms. As the atrium contracts, pressure builds up inside the atrium and reaches a maximal value after which the atrium begins to relax and pressure reduces. The maximal value is represented at the point 1701 in FIG. 17. Meanwhile, the electrical stimulus propagates to the ventricle and the onset of ventricle excitation occurs at an AV delay of about 120-200 ms later (the AV delay can be about 250 ms or even more in some unhealthy individuals). This excitation of the ventricle manifests on the ECG as the QRS complex. As the ventricle contracts, pressure builds up within it and passively closes the valves between each of the atria and a respective ventricle (AV valves), thus stopping the flow of blood from the atrium into the ventricle and preventing backflow.

During the next period of the ventricular contraction, a period known as isovolumic contraction, or isovolumic phase, that lasts approximately 50 ms, all ventricle valves are closed and the pressure in the ventricle rapidly rises with no significant change in volume, as shown in FIG. 17 by the ventricular pressure line and the ventricular volume line within the vertical lines 1703 and 1704 demarcating the isovolumic phase.

As ventricular pressure further increases, at the time indicated by line 1704 in FIG. 17, the valve between the ventricle and artery opens and blood is ejected out of the ventricle and away from the heart. This phase of ventricular contraction is divided into a rapid ejection phase and a decreased ejection phase. The rapid ejection phase lasts approximately 90-110 ms, during which about ⅔ of the stroke volume is ejected. The rapid ejection phase is represented in FIG. 17 as the period between lines 1704 and 1705.

During the isovolumic phase and in the beginning of the rapid ejection phase, the contraction of the ventricle typically causes a passive increase in atrial pressure. This increase in atrial pressure is considered to be attributable to a mechanical effect of the ventricles' contraction on the associated atria. For example, this atrial pressure increase may be due to the atria being tightly associated with the much larger ventricle; as the large ventricle muscle contracts, it affects the attached atrium. The increased atrial pressure may also result from the backward bulging of valves into the atria, which may be due to the increasing pressure in the ventricles. Passive filling of the atrium continues throughout the cardiac cycle (including between points 1701 and 1702) since there is no valve between the atrium and the vascular system. This continual passive filling in conjunction with the increased pressure due to the mechanical effects of the ventricular contraction, may contribute to the increase in atrial pressure. Thus, the passive atrial pressure increase peaks at some time between the second half of the isovolumic phase (i.e., about 25-35 ms after commencement of the isovolumic phase) and the beginning of the rapid ejection phase (e.g., within the first approximately 10 ms of the rapid ejection phase), as represented in FIG. 17 by point 1702. The passive atrial pressure build-up may be higher than the maximal atrial pressure due to atrial contraction, as shown in FIG. 17 by the higher atrial pressure at point 1702 relative to the lower atrial pressure at point 1701.

The rapid ejection phase is followed by the decreased ejection phase lasting about 130-140 ms. Thereafter, all valves close again and the ventricle relaxes in isovolumic relaxation for about 60-80 ms, during which the pressure in the ventricle drops. At this time, the valves between the ventricle and the atria reopen allowing blood to flow freely into the ventricle, after which a new cardiac cycle may commence.

Controlling Atrial Pressure and Atrial Stretch

In the present disclosure, cardiac stimulation may be used to increase atrial pressure and stretch and thereby reduce blood pressure (BP). Cardiac stimulation may achieve increased atrial pressure by stimulating the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation. Embodiments may reach maximum atrial pressure by causing maximum atrial contraction at a period of time overlapping the maximum passive increase in atrial pressure. For example, cardiac stimulation may be used to reach maximum atrial pressure resulting from atrial contraction during a time between about 25-35 ms after the beginning of the isovolumic phase and about 10 ms after the end of the isovolumic phase. Increasing atrial pressure (by overlapping in time atrial pressure resulting from atrial contraction with passive increase in atrial pressure) increases atrial stretch, which is known to affect blood pressure through hormonal and/or neuronal pathways. For example, an increase in atrial stretch may cause secretion of atrial natriuretic hormone or atrial natriuretic peptide, which in turn may reduce blood pressure.

In some embodiments, maximum atrial pressure resulting from atrial contraction is considered to have occurred at a period of time overlapping the maximum passive increase in atrial pressure if maximum atrial pressure resulting from atrial contraction fully or at least partially coincides with the maximum passive increase in atrial pressure. For example, maximum atrial pressure resulting from atrial contraction is considered to have occurred at a period of time overlapping the maximum passive increase in atrial pressure if the maximum atrial contraction is expected to occur within about 20 ms before or after the expected maximum passive increase in atrial pressure. In some embodiments, maximum atrial pressure means the highest part of the contraction or passive pressure increase, having a pressure value that is at least approximately 25% above the pressure value of the atrium at rest. Optionally, maximum atrial pressure resulting from atrial contraction is considered to have occurred at a period of time overlapping the maximum passive increase in atrial pressure if only one peak in pressure is observed from the atrial contraction and passive pressure increase, or if two peaks are observed, the maximum atrial pressure resulting from atrial contraction and the maximum passive increase in atrial pressure are no more than about 30 ms apart. Optionally the overlap in time can be detected mathematically by analyzing measured values and/or visually, for example, by plotting atrial pressure over time or atrial pressure change over time.

BP or a change in BP may be measured as systolic BP (SysBP), diastolic BP, mean arterial BP, BP in one or more chambers, and/or any other related BP parameter. In some embodiments, an electrical stimulator, such as a pacemaker or other type of device having a pulse generator, may be used to stimulate a patient's heart to reduce blood pressure. Electrodes electrically connected to the electrical stimulator with a wired or wireless connection may be placed adjacent a cardiac chamber. The electrical stimulator may be operated to deliver a pulse to the cardiac chamber via the electrode.

In some embodiments, stimulating the heart such that the atrium reaches an increased (and preferably, maximum) atrial pressure resulting from atrial contraction at a period of time overlapping the (preferably, maximum) passive pressure increase in atrial pressure may consequently reduce blood pressure. For simplicity, in the following description, such stimulation may be termed "AC (Atrial Contraction) stimulation." AC stimulation may include delivering at least one stimulation pulse to at least one chamber of a heart such that the atrium reaches maximum atrial pressure resulting from atrial contraction during the period between the second half of the isovolumic phase and the first approximately 10 ms of the rapid ejection phase. Such a stimulation pulse will be referred to herein as an "AC stimulation pulse" or "AC pulse."

As used herein, a "stimulation pulse" may comprise a sequence of one or more excitatory electrical pulses (or stimulation pulses) delivered to one or more chambers of the heart within the timeframe of a single heartbeat (when a single heartbeat is defined as a period of time between two relaxations of the ventricle, between which only a single contraction of the ventricle takes place). Optionally, such excitatory electrical pulses (or stimulation pulses) are also termed pacing pulses. For example, in some embodiments, a stimulation pulse may comprise one or more electrical pulses delivered to one or more locations in a ventricle and/or one or more electrical pulses delivered to one or more locations in an atrium. Thus, in some embodiments, the stimulation pulse may include a first electrical pulse delivered to an atrium and a second electrical pulse delivered to the corresponding ventricle. In some embodiments, the stimulation pulse may include a first electrical pulse delivered to an atrium, a second electrical pulse delivered to the corresponding ventricle, and a third electrical pulse delivered to the atrium after it has exited a refractory period associated with the first pulse. In some embodiments, a stimulation pulse may include a single pulse being delivered to a plurality of locations on one or more chambers of the heart.

In some embodiments, an AC pulse may be delivered at such timing relative to the cardiac cycle so as to have an atrial pressure resulting from atrial contraction of an atrium overlap in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation. Preferably, an AC pulse may be delivered at such timing relative to the cardiac cycle so as to have the atrium reach maximum atrial pressure resulting from atrial contraction at a time overlapping the maximum passive pressure increase of the atrium. Optionally, this timing of delivery of the AC pulse is set according to one or more sensed events, such as events relating to a cardiac cycle.

For example, atrial and/or ventricular excitation may be sensed and the AC pulse may be delivered to the atrium and/or ventricle accordingly. For example, a pacing pulse may be delivered to the atrium at such timing as is expected to be within about −20 to 30 ms from the sensing or pacing of a ventricle and at least approximately 20 milliseconds from the end of the refractory period of the atrium. Optionally, the heart rate and a ventricle excitation or contraction may be sensed and the timing of a next ventricle contraction or excitation may be estimated, and the AC pulse may be delivered so that an atrial pressure resulting from an atrial contraction in a future heartbeat overlaps in time a passive pressure increase of the atrium. Optionally, the AC pulse may be delivered so that an atrial contraction in a future heartbeat reaches maximum atrial pressure resulting from atrial contraction at a time overlapping the maximum passive pressure increase of the atrium. For example, the AC pulse may comprise a stimulus that is delivered to the atrium about 30 to 0 ms before the expected ventricular excitation or about 50-120 ms before the start of the expected ventricular contraction.

In some embodiments, the stimulation pulse may include a first atrial excitation that is sensed or paced, an electrical pulse that is delivered to the corresponding ventricle, and another electrical pulse that is delivered to the atrium after the atrium has exited a refractory period associated with the first excitation. For example, the time period between the first atrial excitation (e.g., delivery of a first excitatory pulse to the atrium) and the delivery of another excitatory pulse to the atrium may be between about 150 to 250 ms.

In some embodiments, an AC pulse comprises a first electrical pulse delivered to an atrium and a second electrical pulse delivered to the corresponding ventricle. The relative timing of the first electrical pulse and second electrical pulse is controlled to cause the atrium to contract at a time within the period between the second half of the isovolumic phase and early in the rapid ejection phase of the heart at that heartbeat. Since the time between delivery of an excitatory pulse and the onset of contraction is longer for a ventricle than for an atrium, the delay between the delivery of the first pulse and the second pulse may have a negative value, for example, between about −20 and 0 ms.

This precise timing may vary between different patients and between different conditions (e.g., different placement of one or more electrodes on the chambers). Accordingly, in some embodiments the settings of an AC pulse may be adjusted, for example, upon implantation of a device and/or periodically, for example, upon a periodic check or during use (for example, based on feedback from one or more associated sensors).

For example, AC pulses having different settings may be delivered to the patient and atrial pressure may be sensed, until a desired atrial pressure resulting from atrial contraction of an atrium overlapping in time a passive pressure build-up of the atrium is sensed. In some embodiments, a desired atrial pressure may be any pressure that exceeds an atrial pressure that the atrium would reach without the stimulation. Optionally, the desired atrial pressure may be selected as the highest (or being one of the highest) among a plurality of atrial pressures resulting from a plurality of AC pulses having different settings. For example, the AC pulses might differ by having different AV delay between a sensed or paced atrial contraction and a paced or sensed ventricular contraction. As a result, one or more AV pulse settings may be selected for use during a period of time for a given patient.

For example, AC pulses having different settings may be delivered to the patient and atrial pressure may be sensed, until a desired degree of overlap is observed between the maxima of maximum atrial pressure resulting from atrial contraction and passive pressure build-up of the atrium. For example, the AC pulses might differ by having different AV delay between a sensed or paced atrial contraction and a paced or sensed ventricular contraction. As a result, one or more AV pulse settings may be selected for use during a period of time for the given patient.

Optionally, the AC pulses may be delivered as part of pacing patterns that differ in the settings of different pulses within the patterns, and one or more patterns may be selected for repeated use, based on one or more parameters relating to the choice of pulses configured to reduce or prevent atrial kick as well as on the aforementioned pressure overlap.

A stimulation setting means one or more parameters of one or more stimulation pulses delivered in a single cardiac cycle. For example, these parameters may include, one or more of: power, a time interval between electrical pulses that are included in a single stimulation pulse (e.g., AV delay or delay between two atrial pulses), a period of delivery with respect to the natural rhythm of the heart, the length of a stimulation pulse or a portion thereof, and the site of delivery between two or more chambers and/or within a single chamber. An AC stimulation setting, or "AC setting," may include a setting of one or more AC pulses.

In some embodiments, sensing may include sensing electrical activity of one or more chambers of the heart, such as one or more of atrial excitation and/or ventricle excitation. In some embodiments, sensing includes using the sounds of a cardiac cycle to detect cardiac activity. For example, closure of the AV valves results in the first sound of a heartbeat. This closure also signifies the beginning of the isovolumic phase. Optionally, based on the timing of closure of the AV valve and the heart rate, a pulse setting may be selected for a future AC pulse. For example, a stimulatory pulse may be provided to the atrium about 80-10 milliseconds before the next anticipated closure of the AV valve.

Optionally, a refractory period of a cardiac chamber (e.g., an atrium) may be estimated as known in the art. The AC pulse may comprise delivering to the atrium a stimulation pulse that elicits atrial contraction. For example, the stimulation pulse may be timed for delivery after the end of the refractory period, or if delivered during the relative refractory period, have such electrical properties so as to elicit a contraction despite the relatively early timing.

In some embodiments, a heart rate is sensed as known in the art, for example, based on electric activity, sound, pressure, and/or any other means.

In some embodiments, one or more AC pulses may be provided as part of a sequence of pulses, or a pacing pattern, encompassing a plurality of heartbeats. A pacing pattern may comprise a plurality of pacing pulses having different settings. Optionally, all of the pulses may be AC pulses but some may have different pulse settings than others. Optionally, only some of the pulses in a given pattern may be configured to cause the atrium to reach an increased, or maximum, atrial pressure resulting from atrial contraction during the period between the second half of the isovolumic phase and early in the rapid ejection phase.

It is further noted that one or more pulse settings (e.g., timing between events, sensed and/or delivered) may be optimized and/or adjusted to suit a specific patient and/or variation in the patient's cardiac functioning.

For example, a patient's heart rate may vary for many reasons, including activity and time of day. Changes in heart rate may cause changes in the relative timing of cardiac events. Accordingly, one or more of the following parameters may be sensed and used to optimize and/or adjust the pulse setting.

For example, aortic pressure and/or sound associated with the opening of one or both cardiac valves can be used to pin point the timing of the beginning and/or end of the isovolumic phase and/or the beginning of the rapid ejection phase. Such timing may be compared with the time that a pulse is delivered and/or a cardiac event is sensed such that the desired timing of contraction would be achieved more precisely and/or more repeatedly.

In another example, one may measure the timing from the delivery or sensing of an excitation stimulus (to an atrium and/or to a ventricle) to when peak pressure is sensed in the atrium (due to contraction or passive pressure build-up).

Another option may be to adjust the AC pulse settings according to one or more of heart rate, patient activity, posture, and/or respiration rate.

In fact, a combination of the above may be used for adjustment and/or optimization. For example, one may measure one or more of the timing between atrial excitation and maximum atrial pressure resulting from atrial contraction, ventricle excitation, maximal atrial passive pressure, and the timing of the isovolumic phase and/or rapid ejection phase. Optionally, one may measure atrial pressure resulting from the delivery of stimulation pulses and adjustment may include selecting a stimulation setting according to the measured resulting pressure. These measurements may also be correlated with the patient's heart rate at different conditions. Using the specific measurements taken from the patient, the pulse setting may be adjusted or optimized.

The optimization and/or adjustment as discussed above may be performed as a closed loop, for example, in some cases where a sensor is associated with the implanting stimulation device. Alternatively, the optimization and/or adjustment may be performed as an open loop. The optimization and/or adjustment may be an ongoing process (especially if the sensor is implanted, for example, according to heart rate) and/or may be performed during implantation when a patient is provided with a device, occasionally, and/or upon need. Finally, the optimization and/or adjustment may be automated and/or involve a medical practitioner.

Embodiments may implement different pacing techniques to achieve AC stimulation and a desired overlap of the atrial pressure resulting from atrial contraction and the passive increase in atrial pressure. In some embodiments, AC stimulation may include pacing the atrium at an atrial rate substantially equal to an intrinsic ventricular rate or pacing the atrium at an atrial rate that is greater than the intrinsic ventricular rate. In addition, different pacing techniques may be implemented to achieve the desired AC stimulation with either a single contraction of the atrium or a double contraction of the atrium.

For a single contraction of the atrium, pacing techniques that achieve the desired AC stimulation may, for example, include:

a. Sensing the atrium (optionally involving anticipating the atrium activation) and pacing the ventricle;
b. Sensing the ventricle and pacing the atrium, which may require that the pacing of the atrium be performed before the anticipated time of ventricle sensing; or
c. Pacing the atrium and pacing the ventricle.

For a double contraction of the atrium, pacing techniques that achieve the desired AC stimulation may, for example, include:

a. Sensing first the atrium activation, sensing the ventricle, and pacing the atrium in the same cardiac cycle to create a second contraction;
b. Sensing the atrium, pacing the ventricle, and pacing the atrium in the same cardiac cycle to create a second contraction;
c. Pacing the atrium, sensing the ventricle, and pacing the atrium again; or
d. Pacing the atrium, pacing the ventricle, and pacing the atrium again.

Other pacing techniques may be employed to achieve the desired AC stimulation and overlap of the atrial pressure resulting from atrial contraction and the passive increase in atrial pressure. Accordingly, notwithstanding the particular benefits associated with the pacing techniques described herein, the present embodiments should be considered broadly applicable to any pacing technique that provides the desired AC stimulation and overlap.

Figure 18:
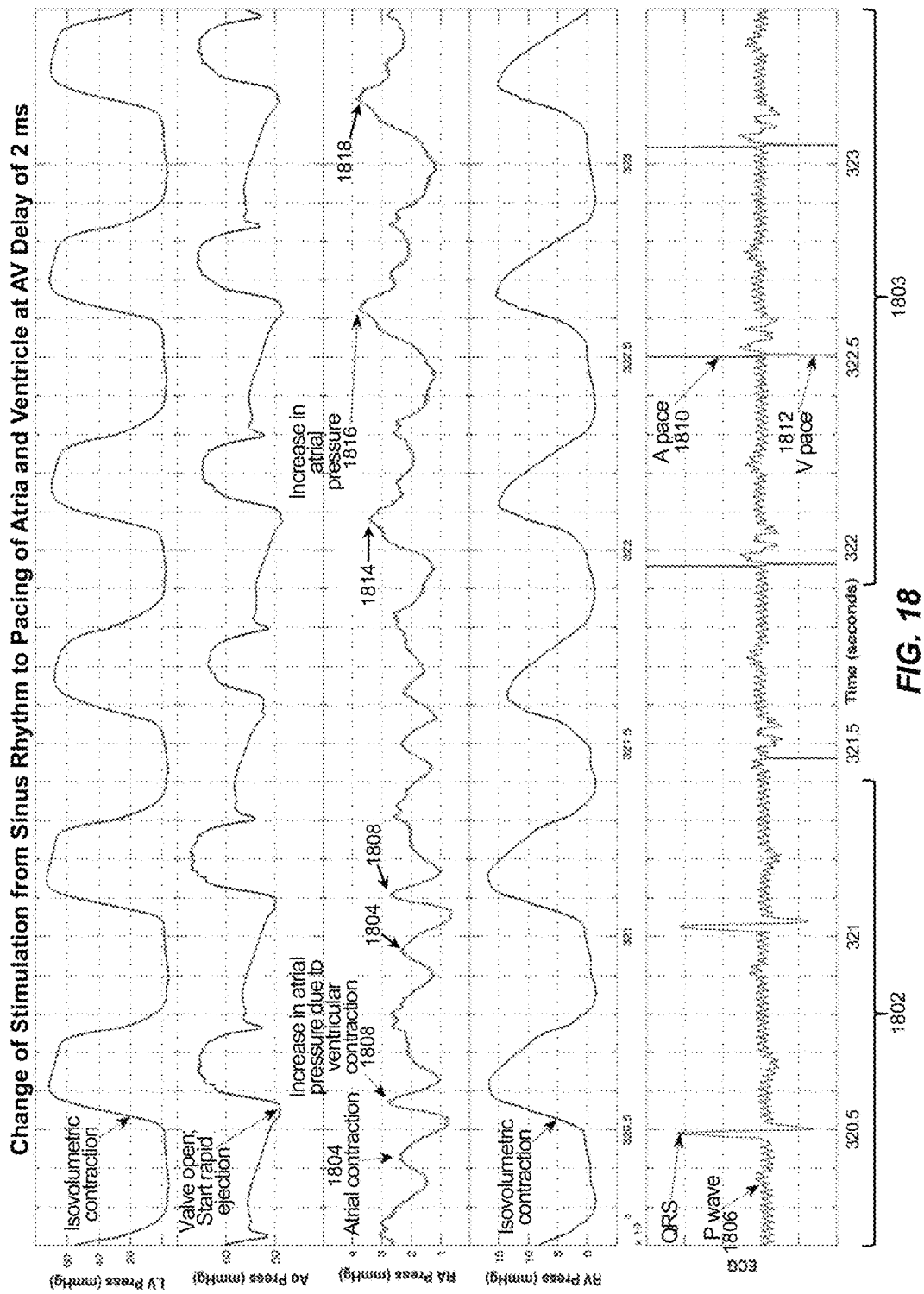
FIG. 18 is a set of graphs illustrating an electrocardiogram (ECG), right ventricle pressure (RV Press), right atrial pressure (RA Press), aortic pressure (Ao Press), and left ventricle pressure (LV Press) traced over a period of time in which stimulation is changed from sinus rhythm to pacing of an atria and a ventricle at an AV delay of 2 ms, showing a significant increase in atrial pressure, according to an embodiment.
Figure 19:
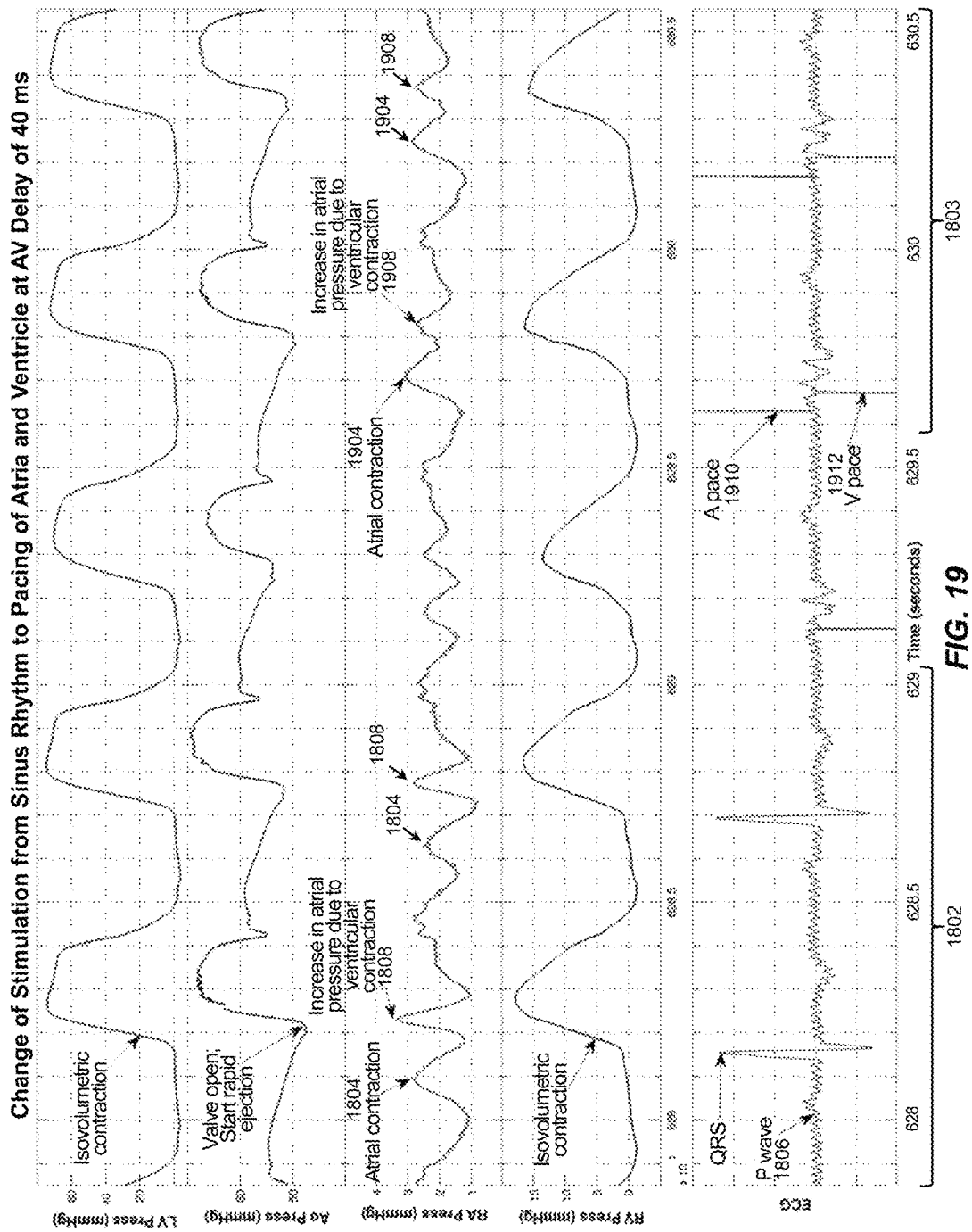
FIG. 19 is a set of graphs illustrating an electrocardiogram (ECG), right ventricle pressure (RV Press), right atrial pressure (RA Press), aortic pressure (Ao Press), and left ventricle pressure (LV Press) traced over a period of time in which stimulation is changed from sinus rhythm to pacing of an atria and a ventricle at an AV delay of 40 ms, showing no significant increase in atrial pressure.

FIGS. 18-19 are graphs illustrating two different stimulation patterns delivered to a healthy anesthetized canine heart, showing an electrocardiogram (ECG), right ventricle pressure (RV Press), right atrial pressure (RA Press), aortic pressure (Ao Press), and left ventricle pressure (LV Press) traced over a period of time. According to one embodiment, FIG. 18 illustrates a change of stimulation from sinus rhythm to pacing of the atria and ventricle at an AV delay of 2 ms, which resulted in an overlap of the pressure due to atrial contraction and the atrial pressure due to passive pressure increase. In this example, the pacing at an AV delay of 2 ms caused an overlap in time of the maximal pressure due to atrial contraction and the maximal atrial pressure due to passive pressure increase, as well as a measurable increase in atrial pressure, and therefore also atrial stretch. For comparative purposes, FIG. 19 illustrates an AV delay of 40 ms, which showed a lesser degree of overlap and yielded no significant increase in atrial pressure. Optionally, a higher degree of overlap may be defined as a function of the proximity of atrial pressure maxima—the closer the maxima, the higher the overlap, until the maxima overlap completely and a single maximum pressure is observed. Optionally, the degree of overlap is a function of the maximal sensed atrial pressure, with a higher pressure maximum value characterizing a higher degree of overlap.

In the experiments associated with FIGS. 18-19, a healthy canine heart was equipped with a pacemaker configured with algorithms that allow pacing at a specified AV delay. The pacemaker was connected to the heart via two pacing electrodes, one in the right atrial appendage and one in the right ventricular apex. Four solid state pressure sensors were inserted into the right atria, the right ventricle, the left ventricle, and the aorta. A single lead ECG was also connected to the animal. The sensors were connected to amplifiers and a data acquisition system (DAQ system), and the signal was sampled at the rate of 1 kHz and plotted, to provide the graphs shown in FIGS. 18-19. As shown, the graphs include from bottom to top the following plots: ECG, RV pressure, RA pressure, Ao pressure, and LV pressure.

In each experiment, the heart was allowed to contract using the natural sinus rhythm for a few beats and was then paced at both the atria and the ventricle with the designated AV delay.

Referring to each of FIGS. 18-19, during the period of time of sinus rhythm 1802, two distinct increases in atrial pressure can be seen. The first atrial pressure increase 1804 follows the atrial electrical activity (the P wave 1806) and corresponds to the contraction of the atria. The second atrial pressure increase 1808 occurs during the isovolumic contraction of the ventricle (characterized by a rapid increase in ventricle pressure) and continues through a short initial period of the rapid ejection phase (starting when the aortic pressure starts to increase). The effect of ventricle contraction on the atrial pressure causes the second atrial pressure increase 1808. As shown in the RA Press plots of FIGS. 18-19, the maximum atrial pressure reached during the isovolumic contraction is slightly higher than the maximum atrial pressure reached during contraction of the atria.

As described above, embodiments may include provisions to maximize atrial pressure, and therefore maximize atrial stretch. In particular, stimulation may be delivered to an atrium at such timing relative to the cardiac cycle so as to cause the atrium to reach maximum atrial pressure resulting from atrial contraction at a time overlapping the maximum passive pressure increase of the atrium. FIG. 18 illustrates one example of this timing, in which the atria and ventricle are paced at an AV delay of 2 ms, as represented by the atrial pace 1810 followed 2 ms later by the ventricular pace 1812. FIG. 18 shows three instances of this pacing.

Referring to the portions of the right atrial pressure plot (RA Press) in FIG. 18, with the three instances of pacing, significant increases in atrial pressure can be seen at points 1814, 1816, and 1818. Those significant pressure increases result from the simultaneous, or nearly simultaneous, atrial pressure increases due to atrial contraction and to contraction of the ventricle. In other words, comparing the sinus rhythm portion 1802 of the right atrial pressure plot to the AV delay paced portion 1803 of the right atrial pressure plot, the first and second atrial pressure increases 1804 and 1808 of the sinus rhythm portion 1802 are essentially superimposed in the AV delay paced portion 1803 such that the atrial pressure increases 1804 and 1808 are combined to provide the higher atrial pressure increases 1814, 1816, and 1818.

Optionally, an AC pulse may have a setting that includes a predefined AV delay between a sensed or paced atrial excitation and a paced or sensed ventricular excitation. The AV delay may be selected such that the atrial pressure resulting from atrial contraction and passive atrial pressure build-up overlap, essentially as described above, and such that the atrial pressure of the atrium that is a combination of the atrial pressure resulting from atrial contraction and the passive pressure build-up, is higher than an atrial pressure of the atrium would be without the stimulation (or with a different stimulation). The AV delay may be selected such that the maxima of atrial pressure resulting from atrial contraction and passive atrial pressure build-up overlap, essentially as described above. This setting may vary between patients and may, in time, even change for a given patient. Nonetheless, in most cases it is expected that an AV delay between about 30 ms and about 0 ms will be effective. In some patients (such as the examples shown with healthy canine hearts shown in FIG. 18), the AV delay between atrial excitation and ventricular excitation may be between about 30 ms and about 0 ms or between about 20 ms and about 0 ms.

It is noted that when sensing is used to detect a cardiac event upon which the AV delay is set, the following is optionally taken into account: firstly, when electrical excitation is sensed, there is a delay between actual excitation and its detection. This may be due to the location of the sensing electrode as well as to limitations of the sensing system. Thus, for example, the time period between a sensed atrial excitation and delivery of a pacing pulse to a ventricle would be shorter than the desired AV delay. When sensing is based on a mechanical event (e.g., contraction or valve closure), the time between actual excitation and the occurrence of the mechanical event also needs to be taken into account. Some examples for the relative timing of sensed events and the delivery of pacing pulses are disclosed herein.

In addition, as detailed in this application, the settings may be adjusted to suit the specific times of a patient upon implantation and/or periodically.

In contrast to the surprising beneficial results achieved by pacing with an AV delay that causes atrial contraction of an atrium to overlap in time a passive pressure build-up of the atrium, thereby providing an atrial pressure of the atrium that is a combination of the atrial pressure resulting from atrial contraction and the passive pressure build-up and is higher than an atrial pressure of the atrium would be without the stimulation (as in the example of FIG. 18), FIG. 19 illustrates an AV delay that is short relative to normal AV delays (e.g., 140 ms in canine hearts), but does not provide a significant increase in atrial pressure. As shown in FIG. 19, after the sinus rhythm portion 1802, the heart was paced at an AV delay of 40 ms during the AV delay paced portion 1803, as represented by the atrial pace 1910 followed 40 ms later by the ventricular pace 1912. FIG. 19 shows two instances of this pacing. Referring to the portions of the trace of the atrial pressure (RA Press) shortly after the pacing, despite the short 40 ms AV delay relative to a normal 140 ms AV delay, the 40 ms AV delay did not result in a significant increase in atrial pressure over the atrial pressure increases 1804 and 1808 of the sinus rhythm portion 1802. Instead, as shown in FIG. 19, the 40 ms AV delay resulted in two separate atrial pressure increases 1904 and 1908, which were roughly equivalent to the previous atrial pressure increases 1804 and 1808.

Comparing FIG. 18 with FIG. 19 therefore shows that significantly increased atrial pressure occurs when the contraction of the atria and the second half of the isovolumic contraction or early part of the rapid ejection phase of the ventricle occur simultaneously, or nearly simultaneously, as in FIG. 18. That significant increase in atrial pressure may provide a desired release of stress-related hormones for reducing blood pressure. Accordingly, embodiments pace the atria and ventricle at an AV delay of about 2 ms.

Figure 20A:
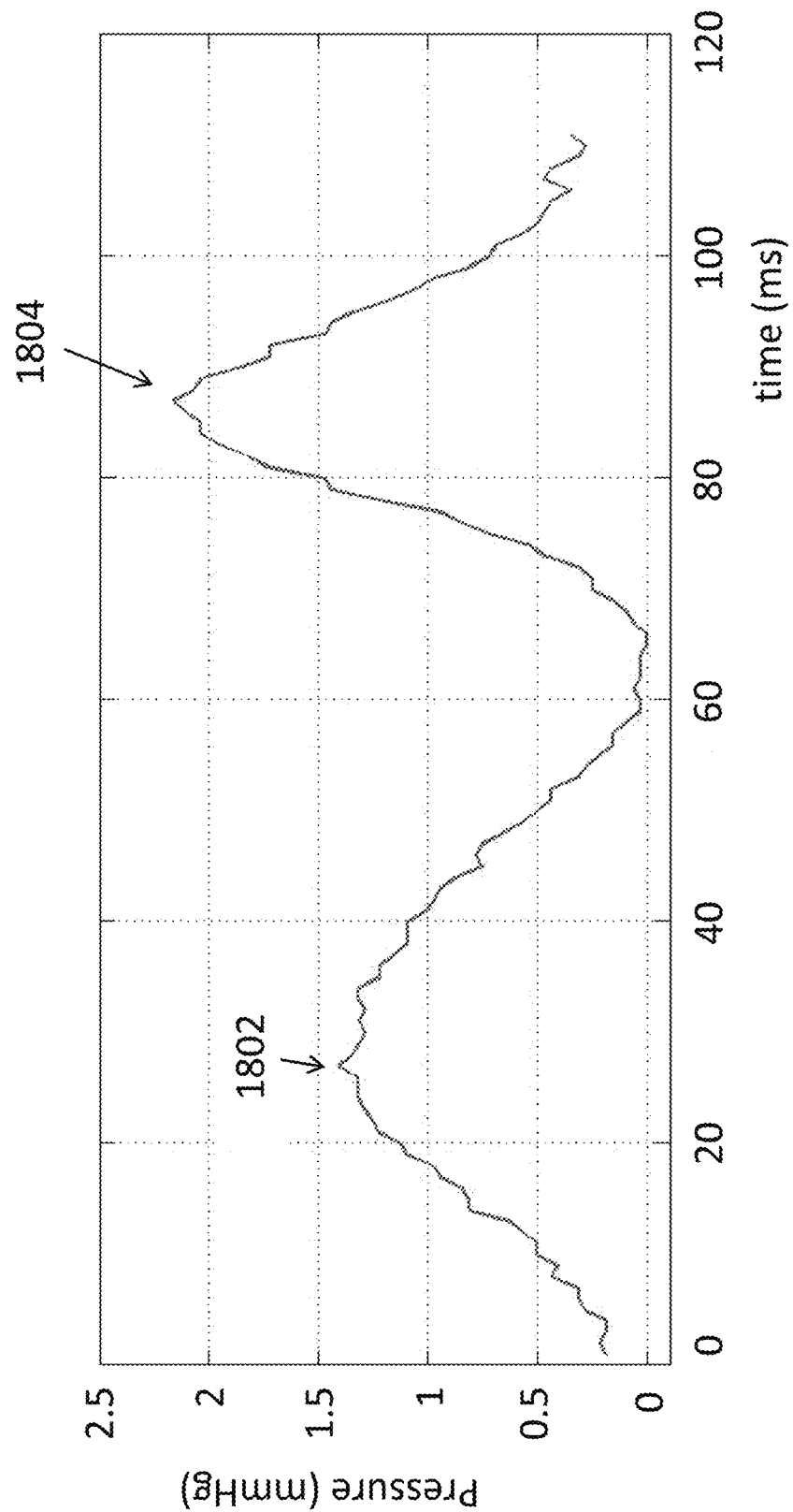
FIGS. 20A-20C are graphs of atrial pressure over time, illustrating different degrees of overlapping between an atrial pressure resulting from an atrial contraction and passive pressure build-up in the atrium taking place at different time intervals between them, with FIG. 20A illustrating an example of no overlap between atrial pressure resulting from an atrial contraction and passive pressure build-up in the atrium, with FIG. 20B illustrating an example for combining an atrial pressure resulting from an atrial contraction and passive pressure build-up in the atrium at a delay of 30 ms between their onsets, and with FIG. 20C comparatively illustrating different degrees of overlap due to delays of 0, 10, 20, 30, 40, 50 and 60 ms.
Figure 20B:
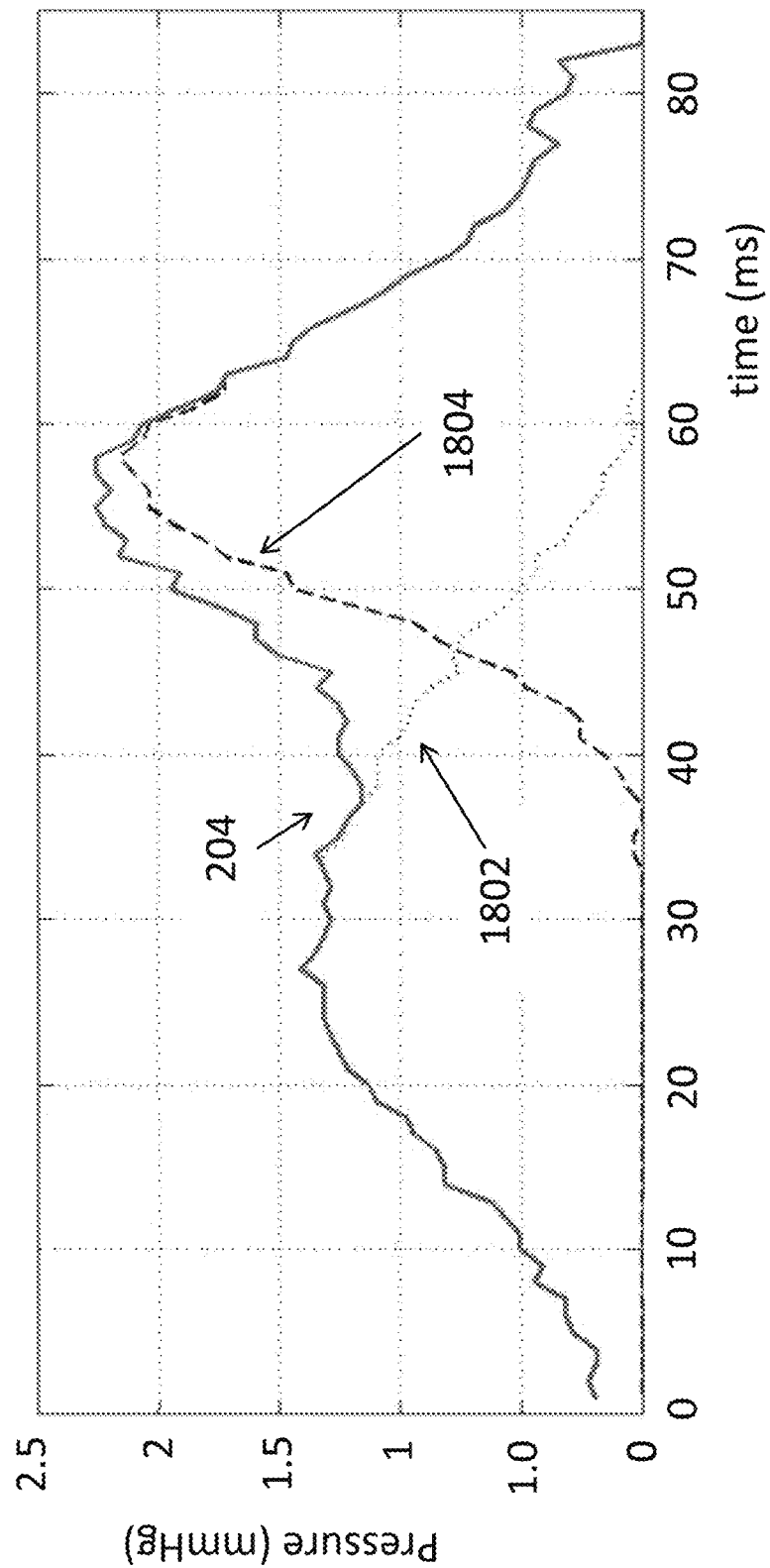
Figure 20C:
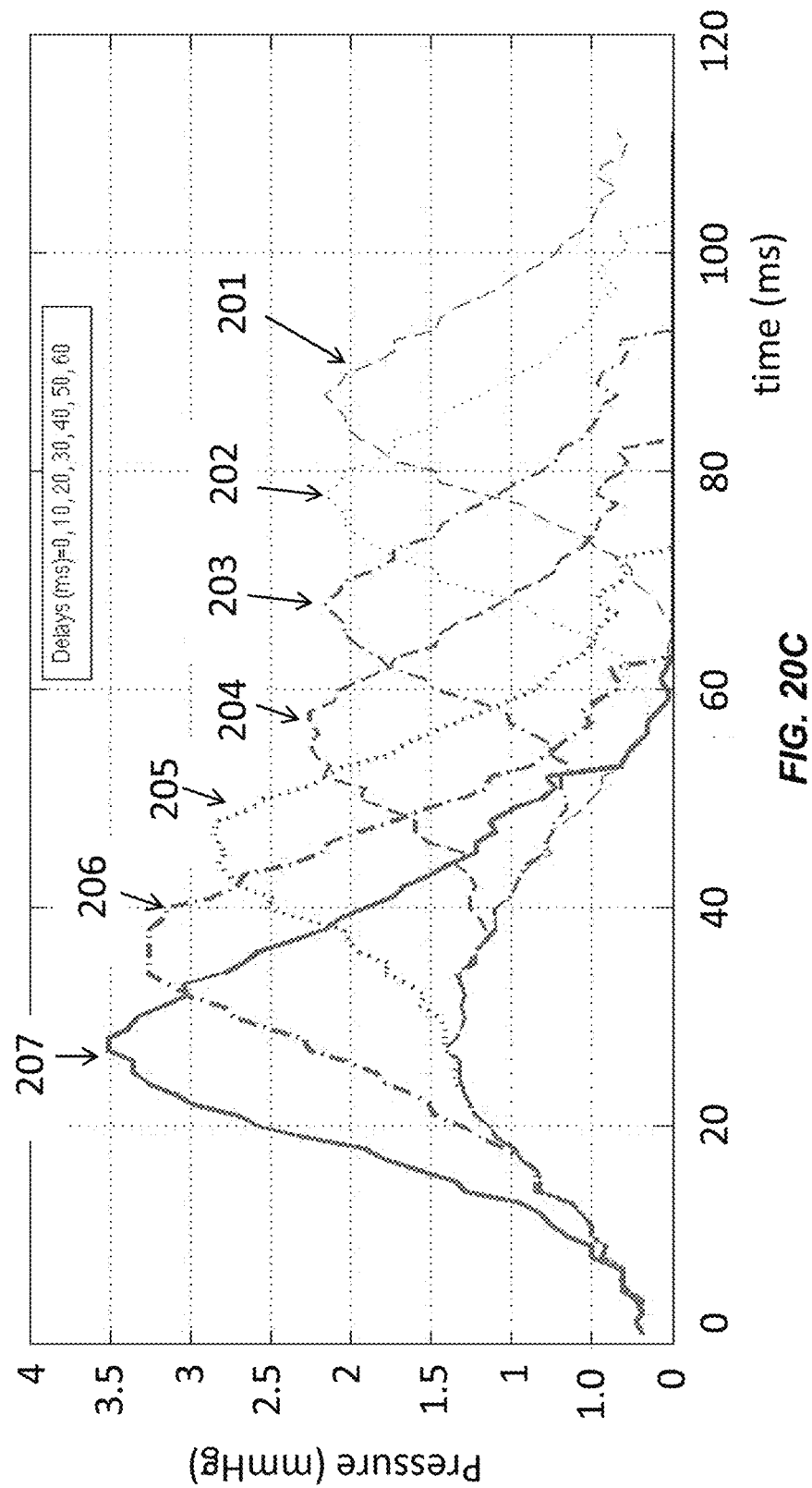

FIGS. 20A-20C depict some theoretical examples for combining atrial pressure due to atrial contraction and passive pressure build-up in the atrium. In these examples, different degrees of overlap are shown, as detailed below, and pressure due to atrial contraction and passive pressure build-up is summed. Initially, atrial pressure was traced during a natural cardiac cycle, such as shown in FIGS. 18 and 19 in the period of time of sinus rhythm 1802. From this tracing, atrial pressure due to atrial contraction 1804 and passive pressure build-up 1804 were extracted. In FIG. 20A, the two pressure curves (corresponding to 1802 and 1804 of FIG. 18) were summed assuming a 60 ms delay between the onset of atrial contraction and the onset of passive pressure build-up. As seen, atrial contraction lasted about 60 ms and reached a maximum pressure of nearly 1.5 mmHg, while passive pressure build-up lasted about 50 ms and reached a maximum pressure a little higher than 2 mmHg. Since the atrial contraction lasted about 60 ms (which is roughly the same as the assumed delay), the two pressure increases are observed as distinct portions in the trace, having two distinct maxima, and the maximal pressure observed is that of passive pressure build-up 1804.

FIG. 20B illustrates in more detail a theoretical combining of atrial pressure due to atrial contraction and passive pressure build-up in the atrium. In this tracing, the onset of passive pressure build-up 1804 (dashed line) was assumed to take place 30 ms after the onset of atrial contraction 1802 (dotted line), as shown. The two traces were summed and the sum was traced as pressure tracing 204 (solid line). As seen in this example, due to some degree of overlap, the combined pressure line 204 had a maximum pressure that was slightly higher than the maximum pressure observed in passive pressure build-up 1804 (dashed line) without the overlap, while two maxima are still seen, one corresponding to each of the combined tracings 1802 and 1804.

Although timing a maximum atrial pressure due to atrial contraction to occur simultaneously with a maximum passive pressure build-up—such that the maxima occur as a singular event—may yield a maximum attainable atrial pressure, embodiments may provide significant beneficial increases in atrial pressure through a range of times beyond that singular event. In other words, to stimulate a heart to obtain an atrial pressure that is a combination of the atrial pressure resulting from atrial contraction and the passive pressure build-up and is higher than an atrial pressure of the atrium would be without stimulation, the timing of stimulation need only provide that the combination (e.g., sum) of the atrial pressure resulting from atrial contraction and the passive pressure build-up is greater than the maximum pressure generated in the atrium without stimulation. If the maximum atrial pressure due to atrial contraction occurs simultaneously with the maximal passive pressure build-up of the atria, the combination (e.g., sum) of those pressures is likely to be greater than each of the individual pressures. However, providing a combined atrial pressure that is greater than both of the individual pressures is not limited to that singular event of simultaneously occurring maxima points and will be true for a range of times over which the pressures overlap each other, as discussed in more detail below.

In FIG. 20C, pressure due to atrial contraction and passive pressure build-up were combined at various hypothetical degrees of overlap between them, thus exemplifying how controlling the relative timing of atrial and ventricular contraction may affect the combined atrial pressure. In this example, like in FIG. 20B, a time delay between the onset of atrial contraction and onset of passive pressure buildup was assumed, and accordingly, at each point in time the atrial pressure due to atrial contraction was summed with the passive pressure build-up at the same point in time, thereby providing a combined pressure. The combined (e.g., summed) pressures of different examples are traced in FIG. 20C.

Trace 201 of FIG. 20C is identical to the trace shown in FIG. 20A, with a delay of 60 ms between the onset of pressure due to atrial contraction and passive pressure build-up. In trace 207, on the other hand, the atrial pressure due to atrial contraction and the passive pressure build-up were combined at close to maximal overlap (a 0 ms delay between the onset of the two changes in pressure, which due to the different durations may not exactly coincide), i.e., assuming that they both commenced at about the same time. As seen, in this case, trace 207 shows the sum of the pressures reaching a single maximum value of about 3.5 mmHg. Similarly, at a delay of 10 ms (trace 206) a single maximum was observed, slightly later than in trace 207 and having a lower maximum value than that of trace 207. As the time delay increased, in trace 205 (20 ms delay), the tracings begin to separate but still yield a single maximal value (between 2.5 mmHg and 3 mmHg). Trace 204 (30 ms delay; which is identical to the trace shown in FIG. 20B) clearly displays two maxima, but there is still sufficient overlap and the sum of atrial pressure is slightly higher than that of trace 201. Finally, at even lower degrees of overlap, in traces 203 and 202 (40 ms and 50 ms delays, respectively), while there is some overlap between pressure due to atrial contraction and passive pressure build-up, in each of the traces the two maxima are more than 30 ms apart and the maximal pressure is about the same as in trace 201, where no overlap was shown.

In some embodiments, a stimulation pattern may be used to lower the blood pressure by applying stimulation patterns comprising one or more AC pulses or consisting of AC pulses, only intermittently. For example, applying intermittent AC pulses may allow natural heartbeats to occur in between the AC pulses and/or the pulses that are not configured to cause an overlap between the atrial pressure due to atrial contraction and atrial pressure due to passive pressure build-up (or do not cause an overlap of the respective maxima), thereby providing an atrial pressure of the atrium that is a combination of the atrial pressure resulting from atrial contraction and the passive pressure build-up and is higher than an atrial pressure of the atrium would be without the stimulation. Optionally, the periods of time between the application of AC pulses may be selected according to time constants of secretion and/or absorption of natriuretic peptides, such that sufficient stimulation will be delivered to essentially provide the desired effect but without much excessive stimulation. This may have the benefit of reducing the power used by an implanted device and/or reduce the degree of manipulation of the heart.

Figure 23:
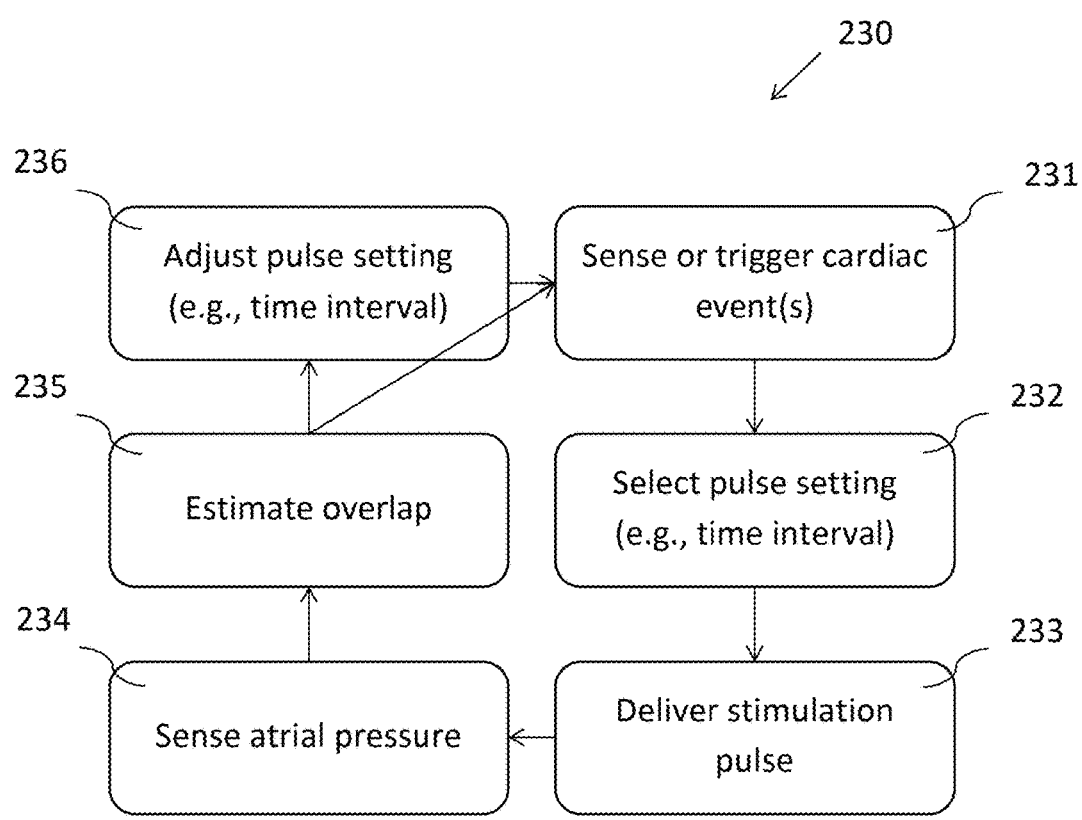
FIG. 23 is a flow chart showing an exemplary method for controlling atrial pressure and atrial stretch, according to an embodiment.

An exemplary method 230 for controlling atrial pressure is depicted schematically in FIG. 23. Method 230 may be performed by an implanted device as described herein. Accordingly, the device may be configured to perform any or all steps of method 230. Similarly, method 230 may include any steps that the device is configured to perform. For example, method 230 may include any of the functions discussed below with respect to device 50 of FIG. 14.

In some embodiments, method 230 may include sensing cardiac event(s), as shown in step 231. This event, or events, may include one or more electrical events and/or mechanical events and may be sensed as known in the art and as described in further detail herein. For example, the sensed events may include sensing of atrial and/or ventricular excitation and/or the timing of steps in the cardiac mechanical activity such as opening and/or closure of one or more cardiac valves. The sensed events may include a deduction of relative timing between cardiac events. In some embodiments, step 231 may include triggering one or more cardiac events, such as atrial or ventricular excitation. Optionally, step 231 may include sensing an intrinsic heart rate, or setting the heart rate. For example, step 231 may include sensing the closure of the AV valve thus defining the beginning of the isovolumic phase, and/or sensing the opening of the aortic valve thus defining the point in time at which the rapid ejection phase begins. Step 231 may also include determining the time difference between sensing the activation of the ventricle or stimulation of the ventricle and the closure of the AV valve that define the beginning of the isovolumic phase.

Method 230 may include a step 232 in which pulse settings are selected. The settings may include or comprise setting a time interval between atrial and ventricular excitations. The settings may include selecting a ratio between atrial excitations and ventricular excitations for a given stimulation pulse. The settings may include power settings based on the sensed or estimated timing of delivery of an excitatory pulse in a relative refractory period of the target chamber.

Method 230 may include a step 233 of delivering at least one stimulation pulse using the pulse settings optionally set in step 232, which pulse settings may be selected based on the timing of the sensed events in step 231. In some embodiments, an excitatory current may be applied to both ventricles, at the same time or in sequence. In some embodiments in which both ventricles are paced in sequence, a time interval may be measured between the onset of excitation of at least one atrium (e.g., the right atrium) and the onset of excitation of the corresponding ventricle to be paced (e.g., the right ventricle). In some embodiments in which a time interval is set to be zero or negative, step 233 may be performed before or at the same time as step 231. In some embodiments, the time interval may be measured in milliseconds.

The pulse settings selected in step 232 may be selected based on feedback. In such cases, method 230 may include sensing atrial pressure, as shown in step 234. For example, feedback information may be obtained by using an implanted sensor for feedback and adjustment of pulse settings, on an ongoing basis and/or on a periodic basis, such as during implantation and/or periodic checkups. Method 230 may include a step 235 of estimating the overlap in time between an atrial pressure (preferably, a maximum atrial pressure) resulting from atrial contraction and a passive pressure build-up of the atrium (preferably, a maximum passive pressure build-up). For example, the estimating of step 235 may include detecting a number of maxima in atrial pressure and their length in time and/or the distance in time between the maxima, and/or detecting a number of maxima and minima in atrial pressure and estimating the duration of a contraction or change in pressure based on the time between maxima and minima, and/or detecting the maximal value of atrial pressure compared to atrial pressure of the same heart without the stimulation. This comparison may be performed using a stored value corresponding to a pressure measured before treatment commenced, and/or may include a step of sensing atrial pressure in at least one heartbeat without the delivery of a stimulation pulse, according to method 230.

Method 230 may include step 236 of adjusting the pulse setting selected in step 232 based on the sensed overlap estimated in step 235. For example, step 236 may include adjusting the time interval to provide the highest degree of overlap observed between a plurality of settings. Optionally, a higher degree of overlap may be defined as a function of the proximity of atrial pressure maxima—the closer the maxima, the higher the overlap, until the maxima overlap completely and a single maximum pressure is observed. Optionally, the degree of overlap is a function of the maximal sensed atrial pressure, with a higher pressure characterizing a higher degree of overlap.

As shown by the arrow directed from step 236 to step 231 in FIG. 23, step 231, step 232, step 233, step 234, and/or step 235 may be repeated after performing step 236. In some embodiments, the time pulse setting may be initially set at a first value during step 231 and, based on feedback sensing performed during steps 234 and 235, the pulse setting may be adjusted (e.g., a time interval reduced or increased) during step 236 until the degree of overlap is within a given range (or above or below a given value).

The steps of method 230 may be performed in any order. For example, the steps may be performed in the order indicated by the arrows shown in FIG. 23. In another embodiment, step 232 may be performed before step 231.

The timing of atrial contraction, atrial excitation, ventricular contraction, closing and/or opening of the AV valve(s), and/or the flow or lack thereof of blood from one or more atria to the respective ventricle(s) and/or blood pressure may be detected by any method known in the art and may be used as feedback control. In some embodiments, the onset of excitation may be used as a trigger for the delivery of an excitatory stimulus to one or more heart chambers (e.g., one or two ventricles or an atrium and a ventricle). The sensed information may be additionally or alternatively used in the adjusting of a timing interval of the device.

Embodiments may provide a method for adjusting a pulse setting in a system for controlling blood pressure. The method may include receiving atrial pressure data associated with an atrium of a heart of a patient during at least one cardiac cycle. The atrial pressure data may result from the system's delivering to the heart a stimulation pulse having a first pulse setting. The method may further comprise analyzing the atrial pressure data, and providing an adjusted second pulse setting according to the analysis, with the adjusted second pulse setting being different from the first pulse setting. The analyzing may include analyzing the atrial pressure data to estimate an overlap in time between an atrial pressure resulting from atrial contraction and a passive pressure build-up of the atrium. The analyzing may also include plotting the atrial pressure data and/or mathematically analyzing the atrial pressure data.

Figure 14:
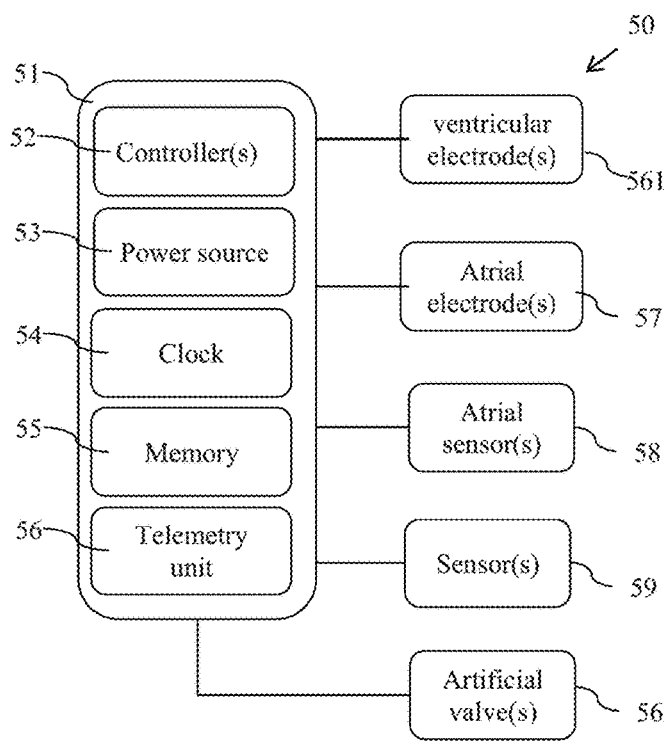
FIG. 14 is a flow chart showing an exemplary device for reducing blood pressure, which may perform one or more of the methods described herein, such as the methods of FIG. 13 and FIG. 23.

Embodiments may provide a system for reducing blood pressure, which may include components such as those shown in FIG. 14. A system may include means for providing information about pressure variation in an atrium during at least one cardiac cycle of a heart, means for generating stimulation pulses, and means for applying the stimulation pulses to at least one cardiac chamber. The means for generating stimulation pulses may be arranged to generate the stimulation pulses so as to control the timing of an atrial contraction relative to the timing of a ventricular contraction in a single cardiac cycle according to the information about pressure variation in the atrium. In one implementation, a means for providing information may first sense the information (e.g., pressures and the time between changes in pressure) and a means for generating stimulation pulses may later time stimulation based on the information.

The information about pressure variation in an atrium may include information about occurrence of an atrial contraction and/or information about occurrence of a ventricular contraction. The information may include information about the relative timing between a maximum atrial pressure resulting from atrial contraction and a maximum passive pressure build-up of the atrium. The information may include information relating to the occurrence and/or timing of one or more cardiac events as described in this specification, including for example one or more of contraction of an atrium, contraction of a ventricle, opening of an atrioventricular valve, closure of an atrioventricular valve, electrical activity of the atria, electrical activity of the ventricle, blood flow, a refractory period of an atrium, and heart rate.

The means for generating stimulation pulses may be arranged for generating for at least one cardiac cycle: at least one atrial stimulation pulse for generating an atrial contraction; and/or at least one ventricular stimulation pulse for generating a ventricular contraction. The means for generating stimulating pulses may be arranged: for generating the at least one atrial stimulation pulse, on the basis of the information about the occurrence of the atrial contraction and/or the information about the occurrence of the ventricular contraction, in a timed relationship to the occurrence of the atrial contraction and/or to the occurrence of the ventricular contraction; and/or for generating the at least one ventricular stimulation pulse on the basis of the information about the occurrence of the ventricular contraction and/or the information about the occurrence of the atrial contraction, in a timed relationship to the occurrence of the ventricular contraction and/or to the occurrence of the atrial contraction. The information about the occurrence of the atrial contraction may include information about the occurrence of a P wave pattern in the natural stimulation pattern of a cardiac cycle. The information about the occurrence of the ventricular contraction may include information about the occurrence of a QRS complex in the natural stimulation pattern of a cardiac cycle.

The timing of atrial contraction relative to ventricular contraction may correspond to an AV delay within a range of about 30 ms to about 0 ms. The means for generating stimulation pulses may be arranged to generate the stimulation pulses so as to: provide an excitatory stimulus to the atrium within a range of about 30 ms to about 0 ms before ventricular excitation occurs; provide an excitatory stimulus to the ventricle within a range of about 30 ms to about 0 ms after atrial excitation occurs; and/or provide an excitatory stimulus to the atrium and then within a range of about 30 ms to about 0 ms later provide an excitatory stimulus to the ventricle.

Other embodiments may provide another system for reducing blood pressure, which may also include components such as those shown in FIG. 14. In those other embodiments, a system for reducing blood pressure may include means for providing information about timing of one or more heart activity events, means for generating stimulation pulses, and means for applying the stimulation pulses to at least one cardiac chamber. The information about timing of one or more heart activity events may include at least one of: occurrence of an atrial contraction of an atrium, occurrence of a ventricular contraction of a ventricle, opening of an atrioventricular valve, closure of an atrioventricular valve, electrical activity of the atria, electrical activity of the ventricle, blood flow, atrial pressure of the atrium, changes in atrial pressure of the atrium, a refractory period of an atrium, and heart rate. The means for generating stimulation pulses may be arranged to generate the stimulation pulses so as to set a timing of atrial contraction relative to ventricular contraction based on the information.

The timing of atrial contraction relative to ventricular contraction may correspond to an AV delay within a range of about 30 ms to about 0 ms. The means for generating stimulation pulses may be arranged to generate the stimulation pulses so as to: provide an excitatory stimulus to the atrium within a range of about 30 ms to about 0 ms before ventricular excitation occurs; provide an excitatory stimulus to the ventricle within a range of about 30 ms to about 0 ms after atrial excitation occurs; and/or provide an excitatory stimulus to the atrium and then within a range of about 30 ms to about 0 ms later provide an excitatory stimulus to the ventricle.

The information about timing of one or more heart activity events may include information about timing between two or more heart activity events in a single cardiac cycle.

The means for generating stimulation pulses may be arranged for generating for at least one cardiac cycle: at least one atrial stimulation pulse for generating an atrial contraction; and/or at least one ventricular stimulation pulse for generating a ventricular contraction. The means for generating stimulating pulses may be arranged: for generating the at least one atrial stimulation pulse, on the basis of the information about the occurrence of the atrial contraction and/or the information about the occurrence of the ventricular contraction, in a timed relationship to the occurrence of the atrial contraction and/or to the occurrence of the ventricular contraction; and/or for generating the at least one ventricular stimulation pulse on the basis of the information about the occurrence of the ventricular contraction and/or the information about the occurrence of the atrial contraction, in a timed relationship to the occurrence of the ventricular contraction and/or to the occurrence of the atrial contraction. The information about the occurrence of the atrial contraction may include information about the occurrence of a P wave pattern in the natural stimulation pattern of a cardiac cycle. The information about the occurrence of the ventricular contraction may include information about the occurrence of a QRS complex in the natural stimulation pattern of a cardiac cycle.

Controlling Atrial Kick

In some embodiments, stimulating the heart such that the contribution of atrial contraction to the filling of the ventricles (atrial kick) is reduced or even prevented, reduces cardiac filling at the end of diastole and consequently reduces blood pressure. For simplicity, in the following description, such stimulation will be termed "BPR (Blood Pressure Reducing) stimulation." BPR stimulation may include delivering at least one stimulation pulse to at least a chamber of a heart such that atrial kick is reduced or even prevented. Such a pulse will be referred to herein as a "BPR stimulation pulse" or "BPR pulse" herein. As described above, a "stimulation pulse" may comprise a sequence of one or more electrical pulses delivered to one or more chambers of the heart within the timeframe of a single heartbeat or cardiac cycle. For example, in some embodiments, a stimulation pulse may comprise one or more electrical pulses delivered to one or more locations in a ventricle and/or one or more electrical pulses delivered to one or more locations in an atrium. Thus, in some embodiments, the stimulation pulse may include a first electrical pulse delivered to an atrium and a second electrical pulse delivered to the corresponding ventricle. In some embodiments a stimulation pulse may include a single pulse being delivered to a plurality of locations on one or more chambers of the heart.

A stimulation setting means one or more parameters of one or more stimulation pulses delivered in a single cardiac cycle. For example, these parameters may include one or more of: power, a time interval between electrical pulses that are included in a single stimulation pulse (e.g., AV delay), a period of delivery with respect to the natural rhythm of the heart, the length of a stimulation pulse or a portion thereof, and the site of delivery between two or more chambers and/or within a single chamber. A BPR stimulation setting, or "BPR setting," may include a setting of one or more BPR pulses.

A stimulation pattern may include a series of pulses having identical stimulation settings or a stimulation pattern may include multiple pulses each having different stimulation settings. For example, a stimulation pattern may have one or more pulses having a first setting and one or more pulses having a second setting that is different from the first setting. When stating that a stimulation pattern has a setting, it is understood that this means a stimulation pattern may include at least one stimulation pulse having that setting. It is also understood that, in some embodiments a stimulation pattern may include one or more cardiac cycles where no stimulation pulse is delivered, in which case the pulse(s) may be viewed as being delivered at zero power. A stimulation pattern may include a plurality of identical pulses or a sequence of pulses including two or more different settings. Two stimulation sequences in a pattern may differ in the order of pulses provided within a setting. Two or more stimulation sequences may optionally differ in their lengths (in time and/or number of heartbeats). In some embodiments, a stimulation pattern may include pulses having BPR settings. In some embodiments, a stimulation pattern may include pulses that do not have BPR settings.

Examples of stimulation settings that are configured to reduce or prevent atrial kick in at least one ventricle may include any of the stimulation settings disclosed herein that are configured to cause a reduction of a patient's ventricular filling volume from the pretreatment ventricular filling volume. This may be caused by having at least part of an atrial contraction take place against a closed AV valve. Some such examples include:

a. Delivering one or more stimulation pulses to a ventricle of a patient 0-50 ms before the onset of excitation in an atrium of the patient. Optionally, this delay is set based on sensing of atrial excitation. Optionally, this includes delivering one or more stimulation pulses to the atrium 0-50 ms after the delivery of stimulation pulses to the ventricle. Optionally, this is performed at a rate that is slightly higher than the natural heart rate of the patient.

b. Delivering one or more stimulation pulses to a ventricle of a patient 0-70 ms after the onset of excitation in an atrium of the patient. Optionally, this delay is set based on sensing of atrial excitation. Optionally, this includes delivering one or more stimulation pulses to the atrium 0-70 ms before the delivery of stimulation pulses to the ventricle. Optionally, this is performed at a rate that is slightly higher than the natural heart rate of the patient.

Some embodiments may provide a system for reducing blood pressure configured to deliver stimulation at a rate higher than the natural heart rate based on sensed natural heart rate or natural excitation. For example, the system may be configured to sense the natural excitation between delivery of stimulation pulses and if a natural activity is sensed, the system may be configured to inhibit the delivery of the stimulation pulse to the chamber. If in a given time frame the amount of sensed activations exceeds a threshold, the natural heart rate may be regarded as higher than the rate of delivery of the stimulation pulses, in which case the rate of delivery may be increased, e.g., to accommodate increased heart rate of a patient. On the other hand, if in a given time frame the amount of sensed activations is lower than a threshold (this threshold may be 0), the natural heartbeat may be regarded as lower than the rate of delivery of the stimulation pulses, in which case the rate of delivery may be reduced, e.g., to avoid over excitation of a patient's heart. To achieve this effect, according to one embodiment, a system for reducing blood pressure may include a sensor for sensing an excitation rate of at least one of an atrium and a ventricle of a patient's heart, a stimulation circuit configured to deliver stimulation pulses to an atrium and a ventricle, and a processor circuit coupled to the stimulation circuit. Optionally, a sensor for sensing the excitation rate of at least one of an atrium and a ventricle may comprise an electrode for sensing atrial excitation. The processor circuit may be configured to detect the patient's heart rate based on the sensing and operate in an operating mode in which a stimulation pulse is provided to each of the at least one of an atrium and a ventricle. The stimulation pulse may be delivered at a rate that is higher than the sensed excitation rate and may be configured to stimulate the ventricle at a time between about 50 ms before and about 70 ms after stimulation of the atrium.

Reducing atrial kick may have an immediate effect on blood pressure while hormone mediated mechanisms may take a longer period. While some devices may be configured to have both an immediate and a hormone mediated effect, optionally, some of the BPR settings and/or stimulation patterns may be configured to reduce or prevent atrial kick without a significant increase in atrial stretch. For example, when the AV valve closes at a time that atrial contraction is at peak pressure or thereafter, premature closure of the valve does not increase atrial stretch. Thus, in some embodiments, a device may be configured to cause the relative timing of atrial excitation and ventricular excitation to be comparable with an AV delay that is at least 40 ms long or at least 50 ms long. Atrial stretch may be measured, calculated, and/or estimated as known in the art. In some embodiments, atrial stretch determination may include measuring atrial pressure. In some embodiments, atrial stretch determination may include measuring or estimating the dimension of an atrium (e.g., diameter, size, or circumference).

In some embodiments, atrial kick may be reduced because the BPR stimulation setting may be set such that atrial contraction of a cardiac cycle is incomplete when the AV valve is open. In some embodiments, atrial contraction may take place completely or in part against a closed AV valve. In some embodiments atrial contraction may be prevented or reduced in pressure and/or force.

In some embodiments, only one or more ventricles may be stimulated and the stimulation pulse may be timed to have an abnormal AV delay (e.g., 50 ms before to 120 ms after atrial excitation). In some embodiments, a BPR stimulation setting may include the delivery of at least one electrical pulse or stimulus to one or more atria. In some embodiments, this at least one atrial stimulus may cause atrial contraction. In some embodiments, the at least one atrial stimulus may interfere with atrial contraction. In some embodiments, the at least one atrial pulse may cause an atrial spasm or another type of inefficient atrial contraction.

The reduction in blood pressure resulting from BPR stimulation may be observed practically immediately upon application of the stimulation signal (e.g., within 1 or 3 seconds (sec) or within 1, 3, or 5 heartbeats) and may reach a minimal blood pressure value within less than 5 heartbeats from the beginning of stimulation.

By controlling the settings of BPR stimulation, one may control the degree to which BP is reduced. This degree is sometimes patient specific and/or related to the precise positioning of one or more stimulation and/or sensing electrodes in or on the heart.

Adaptation a. The inventors found that while stimulation is maintained, blood pressure may display an adaptation pattern wherein blood pressure increases after a time (some of which often occurs in a short time being less than 5 minutes or even less than a minute), and potentially reaches near pre-stimulation blood pressure values (possibly due at least to baroreflex) or even higher. The adaptation, at least in part, may be attributed to changes in properties of the cardiovascular system, such as increase in total peripheral resistance. The inventors further found that termination of stimulation results in a quick return of blood pressure to pre-stimulation values or even higher values, and thereafter that the heart becomes responsive to the blood pressure reducing stimulation signal at a degree similar to a heart that was not so stimulated. In addition, it was found that different stimulation patterns that comprise a plurality of BPR stimulation settings result in different blood pressure adaptation patterns.

b. Stimulation patterns may, for example, comprise at least a first stimulation setting and a second stimulation setting different from the first stimulation setting, the first stimulation setting and the second setting configured to reduce or prevent atrial kick and/or to control atrial pressure and/or stretch. The stimulation pattern may even comprise more than two different stimulation settings. The second setting in some embodiments has a longer AV-delay than the first setting. The second setting in some embodiments may not be configured to reduce atrial kick and/or to control atrial pressure and/or stretch.

Figure 1:
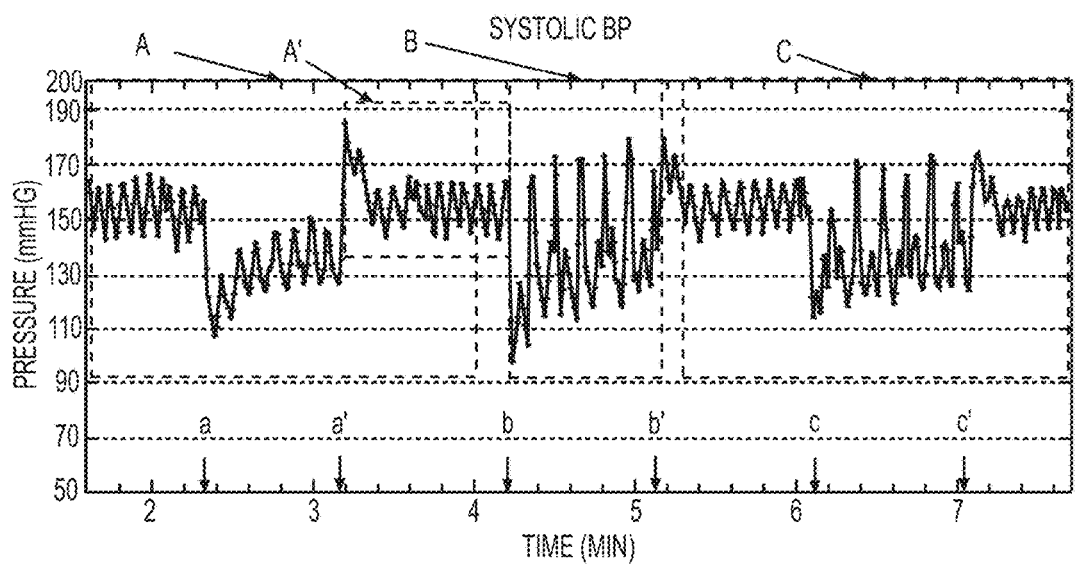
FIG. 1 shows the systolic blood pressure of a hypertensive patient receiving a stimulation signal, plotted against time.

In FIG. 1, the systolic blood pressure of a hypertensive patient receiving a stimulation signal is plotted against time. The crosses along the plotted line depict the peak systolic blood pressure for every heartbeat. During approximately the first 2 plotted minutes, no stimulation signal was delivered. As seen, the patient's initial blood pressure was on average more than 150 mmHg. The oscillations in blood pressure (about ±10 mmHg) are attributed to the breathing cycle, as known in the art.

Then, a first stimulation pattern was applied during time interval a-a', a second stimulation pattern was applied during time interval b-b', and a third stimulation pattern was applied during time interval c-c'. In between the stimulation patterns and after the third stimulation pattern, the heart was not stimulated.

Figure 2:
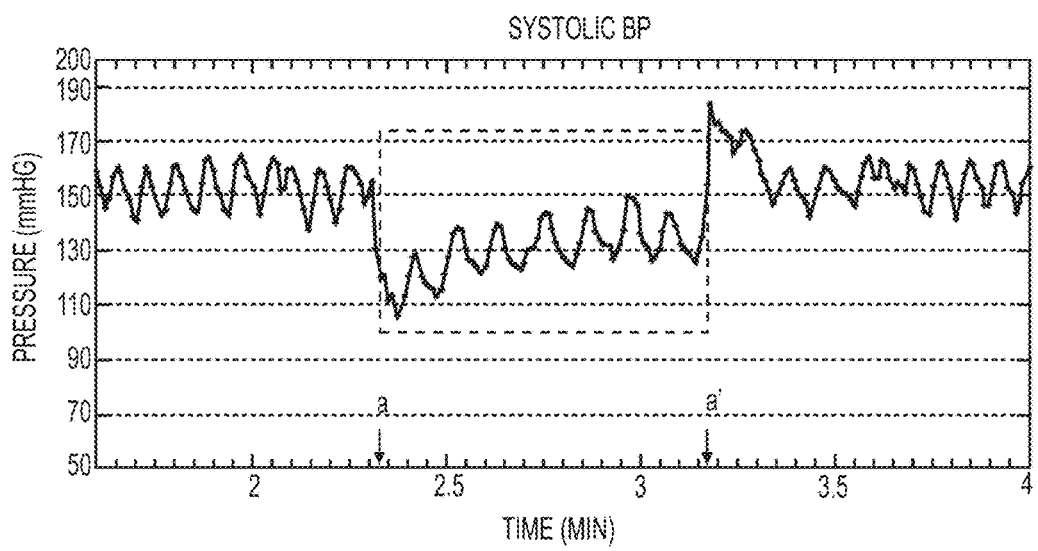
FIG. 2 shows an enlarged view of the portion of FIG. 1 marked by dashed rectangle A.

Attention is now drawn to FIG. 2, depicting an enlarged portion of FIG. 1 marked by dashed rectangle A. During the time marked by the dashed rectangle in FIG. 2, which corresponds with the time interval a-a' in FIG. 1, a stimulation commenced and was delivered to the patient's right atrium and right ventricle, such that the atrium received a BPR stimulation signal (pulse) 2 ms before the ventricle. Stimulation ended at the time marked a' in FIGS. 1 and 2. During the time interval a-a', the patient's systolic pressure initially reduced to a minimal value below 110 mmHg, and then gradually increased to intermediate values, between the initial blood pressure and the achieved minimum. At point a', stimulation stopped and an immediate overshoot in blood pressure was observed, to a value above 170 mmHg. Within about a dozen heartbeats, the blood pressure returned to its initial range.

The changes in blood pressure presented in FIGS. 1 and 2 represent, at least in part, the cardiovascular system's response to changes in blood pressure, known as the baroreflex. The baroreflex acts to restore blood pressure to its pre-stimulation level by changing cardiovascular characteristics (e.g., peripheral resistance and/or cardiac contractility). It may be assumed that the reduction in blood pressure that resulted from the reduction in ventricular filling provoked a baroreflex response directed towards restoration of the pre-stimulation blood pressure. The effect of the baroreflex on the cardiovascular system is evident, for example, at point a' in FIG. 2. At that point, the stimulation that affected ventricular filling was withdrawn and blood pressure immediately exceeded pre-stimulation blood pressure. This may be taken to indicate baroreflex changes to the cardiovascular system (e.g., peripheral resistance increased and contractility increased). At point a', where stimulation stopped and blood pressure peaked, the baroreflex responded to the increase in blood pressure by again changing one or more characteristics of the cardiovascular system, this time in order to lower the blood pressure to the level before the change. As can be clearly seen, the response of the baroreflex feedback to increase and decrease in blood pressure is asymmetric in that the response to an increase in blood pressure is much faster than the response to a decrease in blood pressure. Some embodiments may make use of this asymmetry of the baroreflex to reduce or even prevent adaptation of the reduction in blood pressure due to reduced filling, for example, by controlling a stimulation pattern accordingly, as detailed herein.

Figure 3A:
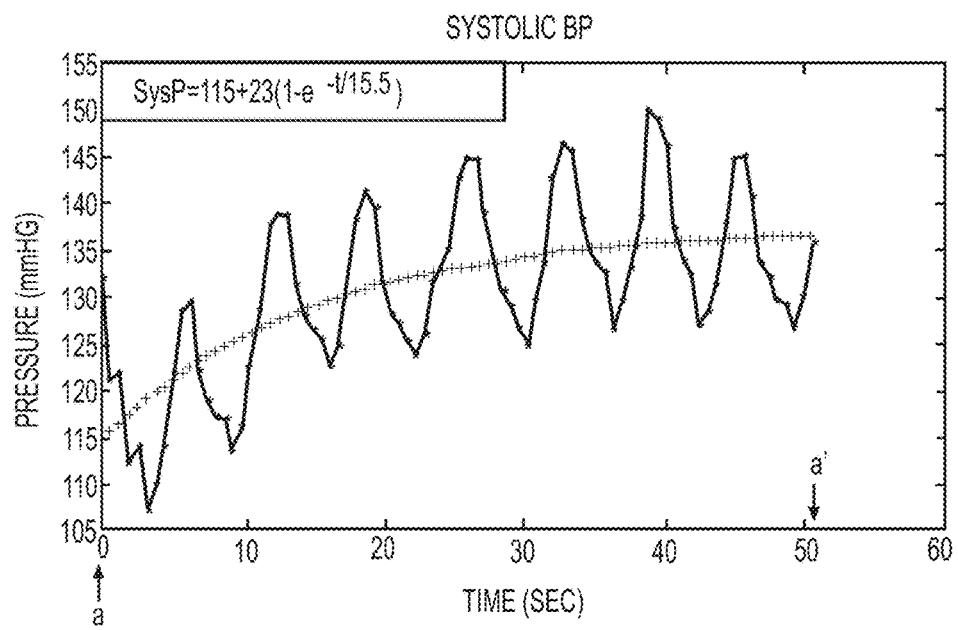
FIG. 3A depicts an enlarged view of the portion of FIG. 2 between time point a and point a'.

FIG. 3A depicts an enlarged view of the curve of FIG. 1 between time point a and point a'. In FIG. 3A, an exponential function was fitted to the plotted curve showing an adaptation response, the function describing a relation between time and SysBP, and having the following formula:

$$P = Pi + DP(1 - e^{-t/k})$$

Where P (in mmHg) denotes the systolic blood pressure, Pi (mmHg) is a first average reduced blood pressure upon commencement of BPR stimulation, DP (mmHg) is a constant representing the amount of increase in pressure after the initial decline to a new steady state level, k (sec) is a response time constant, e is the mathematical constant, being the base of the natural logarithm, and t (sec) is time.

In FIG. 3A, the matching function was as follows:

$$P = 115 + 23(1 - e^{-t/15.5})$$

Where Pi was found to be 115 mmHg, DP was 23 mmHg, and k was 15.5 sec.

Figure 3B:
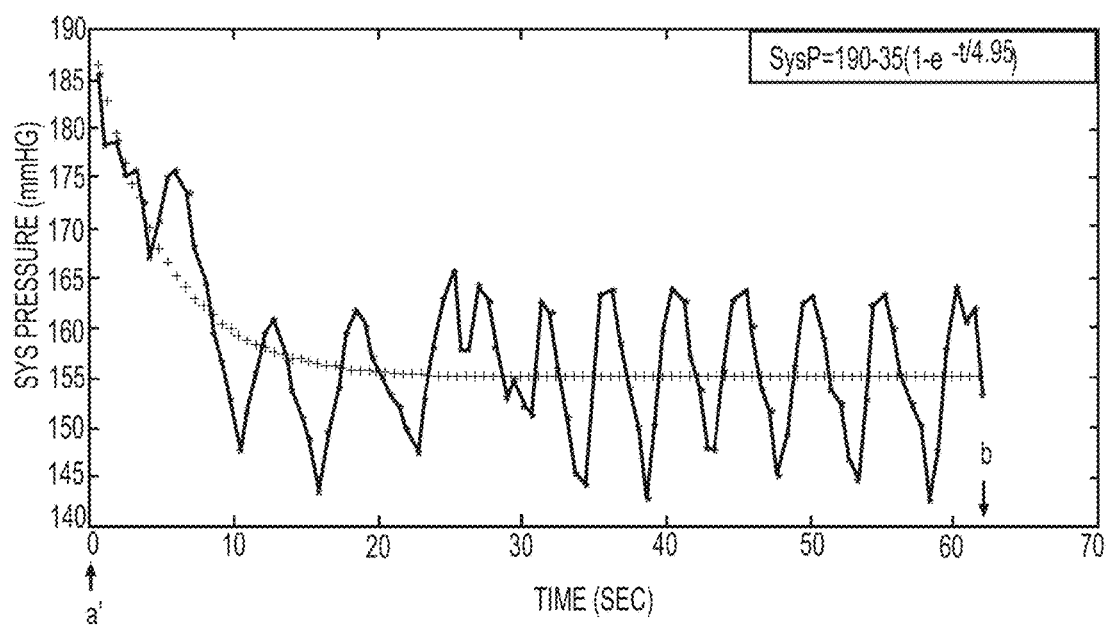
FIG. 3B depicts an enlarged view of the portion of FIG. 1 marked by dashed rectangle A'.

FIG. 3B depicts an enlarged view of the portion of FIG. 1 marked by dashed rectangle A'. In FIG. 3B, an exponential function was fitted to the plotted curve showing an adaptation response to the termination of the delivery of BPR stimulation. As seen, this response, which manifested in a reduction of blood pressure, was faster than the response to BPR stimulation.

In FIG. 3B, the matching function was as follows:

$$P = 190 - 35(1 - e^{-t/4.946})$$

Where Pi was found to be 190 mmHg, DP was −35 mmHg, and k was 4.946 sec.

As mentioned above, the baroreflex response to a reduction in blood pressure is much slower than the baroreflex response to an increase in blood pressure. This is indicated by the ratio of the aforementioned time constants k (about 15 sec to about 5 sec) with a much faster response to the increase in blood pressure. This asymmetry in the speed of the baroreflex response may provide means to design a stimulation pattern that generates an average reduction in blood pressure and reduction or even prevention of adaptation. For example, in a preferred embodiment, a stimulation pattern may alternate between two stimulation settings in a way that the weighted response favors the changes in the cardiovascular system invoked by increase in blood pressure. In this embodiment, the heart may be stimulated using a stimulation pattern having two stimulation settings: the first setting designed to reduce ventricular filling and thereby reduce blood pressure, and the second setting designed to have normal ventricular filling, or at least a higher ventricular filling, than that of the first setting. This stimulation pattern may comprise pulses having the first setting (BPR) delivered for a period of time that is shorter than the time constant of the baroreflex response to the decrease in blood pressure. In such case, adaptation may begin to manifest and blood pressure may increase from the reduced level, but may not reach its pre-stimulation level. The stimulation pattern may also comprise pulses having the second setting (e.g., natural AV delay) delivered for a period of time that is longer than the time constant of the baroreflex response to increase in blood pressure. In this case, full advantage may be taken of the baroreflex caused reduction in blood pressure, and blood pressure may even return to its level before the stimulation pattern switched to this second setting. The weighted response of the baroreflex in such a pattern may reduce or prevent adaptation while the average pressure may be lower than a pre-stimulation level. The relation between the time constants and the period of time allotted to the delivery of pulses having different settings may determine the level of baroreflex response that takes effect during the whole stimulation pattern. If, for a given stimulation setting, the period of delivery is selected to be shorter than the time constant of response, the baroreflex may not be able to change the cardiovascular system back to a pre-stimulation level, and if the period selected is greater than the time constant, the baroreflex effect may be more pronounced.

Figure 4:
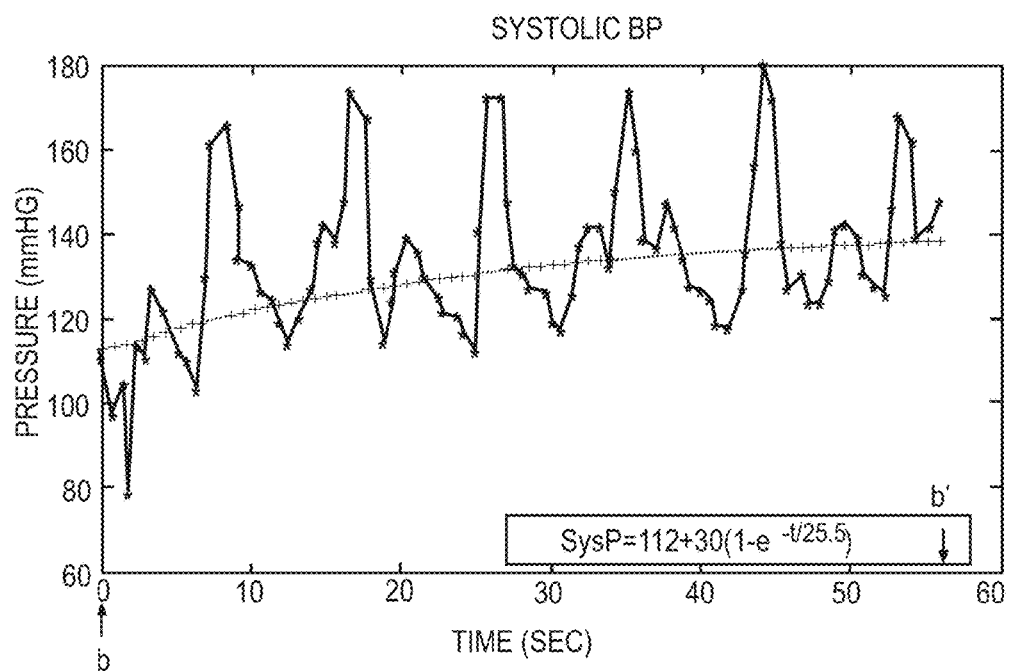
FIG. 4 depicts an enlarged view of the portion of FIG. 1 marked by dashed rectangle B.

As seen in FIG. 1, at the interval between points b and b', a second stimulation pattern was delivered. FIG. 4 depicts an enlarged version of this portion of FIG. 1 (marked by dashed rectangle B in FIG. 1). In the second stimulation pattern, a sequence of 12 BPR pulses were delivered to both an atrium and a corresponding ventricle at an AV delay of 2 ms, followed by 3 heartbeats at which only atrial stimulation and no ventricular stimulation was artificially delivered. During these last 3 heartbeats, ventricular excitation occurred by the natural conductance through the AV node that resulted in an AV delay of ~180 ms. This second stimulation pattern was repeated for the duration of the shown time interval. In FIG. 4, the exponential function matching the curve was found to be the following:

$$P=112+30(1-e^{-t/25.5})$$

As seen, Pi and also DP were comparable to the corresponding values of the first stimulation pattern (a-a' in FIG. 3A). However, k of the second pattern was nearly twice the time constant of the first stimulation pattern. In this time interval, adaptation occurred at a slower rate than in FIG. 3A, but blood pressure spiked more than it did in FIG. 3A when the pattern switched between the stimulation pulses. This result demonstrates that the use of a stimulation pattern having alternating stimulation settings reduced adaptation.

Figure 5A:
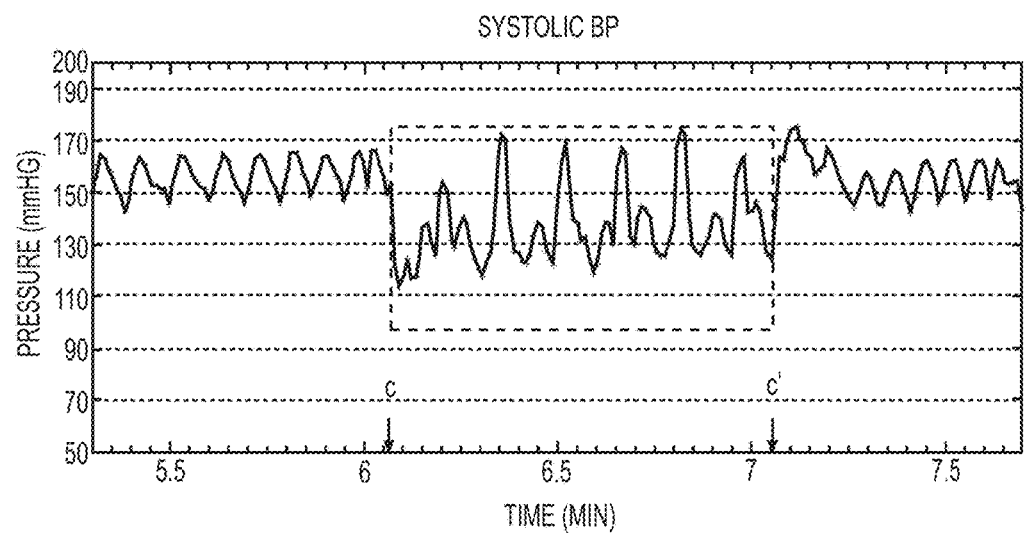
FIG. 5A depicts an enlarged view of the portion of FIG. 1 marked by dashed rectangle C.

A third stimulation pattern was delivered as well, as seen in FIG. 1, between points c and c'. FIG. 5A depicts an enlarged view of the portion of FIG. 1 marked by dashed rectangle C, which includes the portion of the curve between point c and point c'. In the third stimulation pattern, a sequence of 12 BPR pulses was delivered at an AV delay of 2 ms, followed by 3 BPR pulses, each with a 120 ms AV delay. This was repeated for the duration of the shown time interval.

Figure 5B:
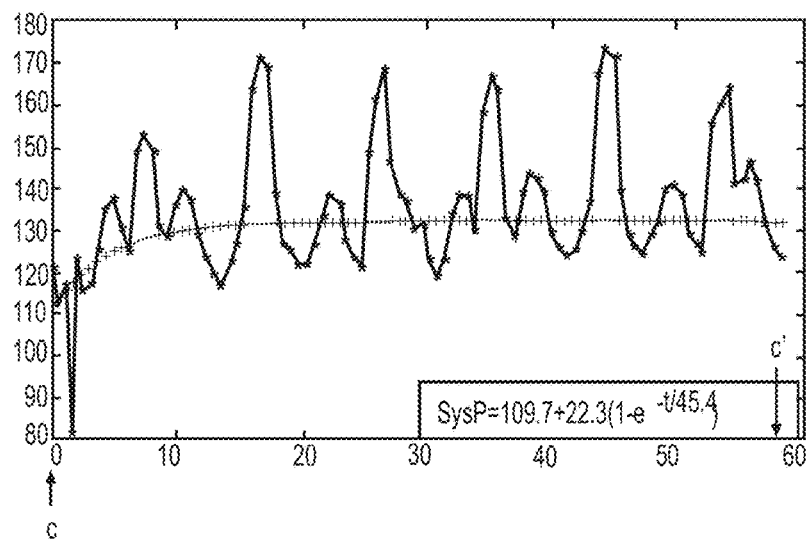
FIG. 5B depicts an enlarged view of the portion of FIG. 5A between time point c and point c'.

The portion of the curve of FIG. 5A that is marked by a dashed rectangle is plotted in FIG. 5B. In FIG. 5B, an exponential function was fitted to the plotted curve showing an adaptation response to the delivery of the stimulation pattern of 12 BPR pulses delivered at an AV delay of 2 ms followed by 3 BPR pulses, each with a 120 ms AV delay.

In FIG. 5B, the matching function was as follows:

$$P=109.7+22.3\ (1^{-}e^{-t/45.4})$$

Where Pi was found to be 109.7 mmHg, DP was 22.3 mmHg, and k was 45.4 sec. As seen, while the initial reduction in blood pressure was comparable with the one shown in FIG. 3A (Pi=115 or 109.5), the adaptation time constant (k) was much higher (45.4 sec v. 15.5 sec), meaning that a low blood pressure was maintained for a period of time that is about 3 times greater than in FIG. 3A.

Figure 6:
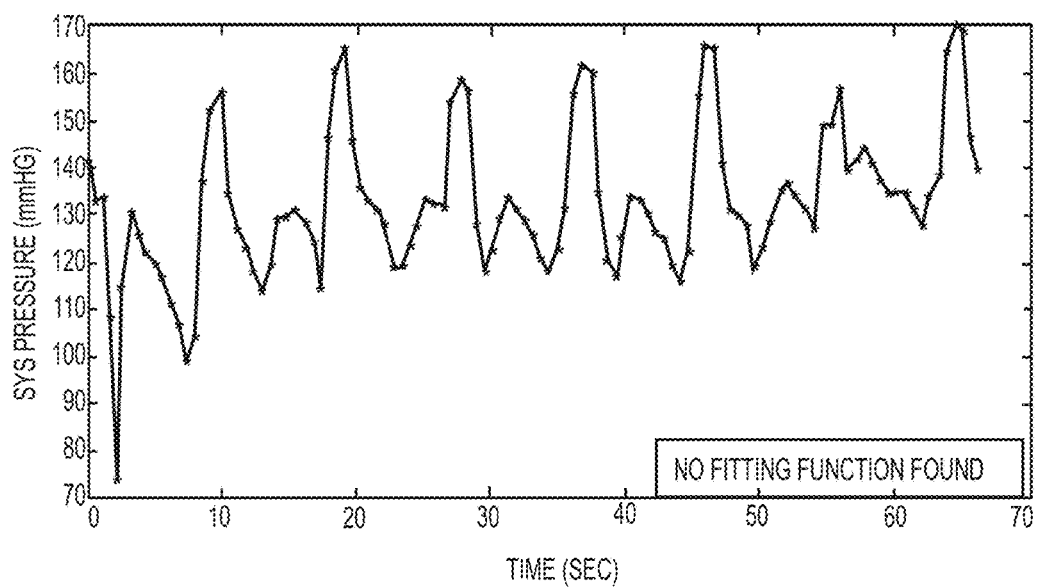
FIG. 6 shows the systolic blood pressure of a hypertensive patient receiving a stimulation signal, plotted against time.

Attention is now drawn to FIG. 6, wherein a hypertensive patient's heart was stimulated at a stimulation pattern having a sequence of 12 BPR pulses delivered at an AV delay of 2 ms, followed by 3 BPR pulses, each with an 80 ms AV delay.

As seen, in this case, the adaptation rate was very low and almost undetectable at the allotted time interval. An exponential formula could not be matched, suggesting that the adaption was extremely slow or did not exist.

Figure 7:
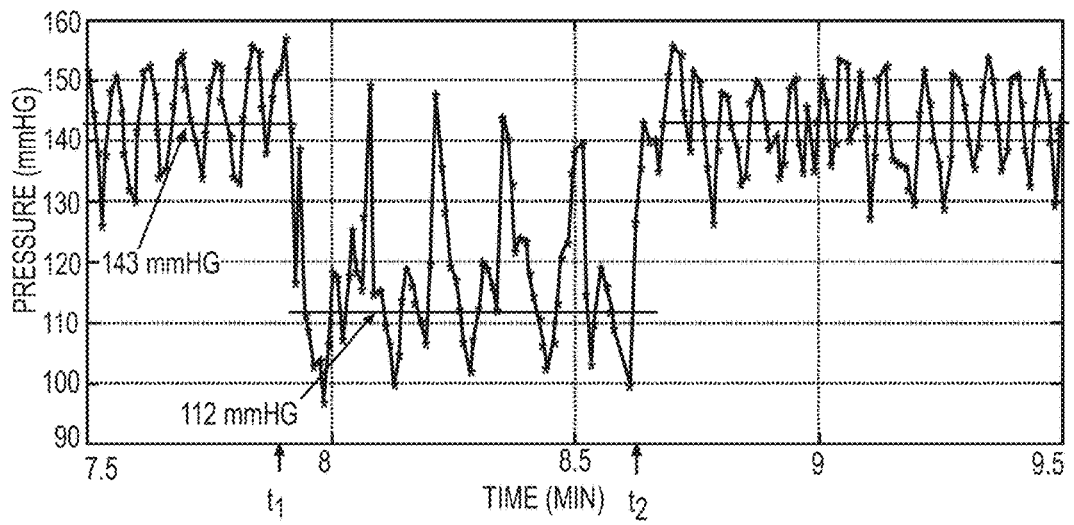
FIG. 7 shows the systolic blood pressure of a hypertensive patient receiving a stimulation signal, plotted against time.

In FIG. 7, a hypertensive patient's heart was stimulated with a stimulation pattern having a sequence of 12 BPR pulses delivered at an AV delay of 2 ms, followed by 3 BPR pulses, each with a 40 ms AV delay. Stimulation commenced at point $t_1$ and ended at point $t_2$. There was no measured adaptation response and the fitting curve was in fact linear and had a fixed average reduced blood pressure of about 112 mmHg, which is about 31 mmHg lower than the blood pressure immediately before and after the time interval $t_1$-$t_2$.

As apparent from the different stimulation patterns shown before, a stimulation pattern comprising at least one BPR stimulation can be set to at least approach one or more targets. For example, in some embodiments, a stimulation pattern may be set to cause an initial reduction in blood pressure (systolic and/or diastolic) that will exceed a predetermined threshold or will be within a predetermined range. In a more specific embodiment, the blood pressure may be reduced by at least a given percentage or by at least a given measure (e.g., 10 or 20 mmHg or even 30 mmHg) or the blood pressure may be reduced to be within a given range (e.g., between 90 and 130 mmHg SysBP) or below a given target (e.g., 130 mmHg SysBP or less). In some embodiments, a target may include maintaining a reduced blood pressure for a prolonged period of time within a reduced average range. For example, the pretreatment blood pressure may be reduced to a predetermined average blood pressure for a period of time or a number of heartbeats. In another embodiment, the target may include causing a given percentage of heartbeats to be at the reduced range/threshold. In some embodiments, the target may include reducing blood pressure while also reducing the level of spikes between stimulation pulses. For example, a stimulation pattern may be used to lower the blood pressure to a constant blood pressure for a predetermined interval of time. In some embodiments, a stimulation pattern may be used to lower the blood pressure without significantly influencing the cardiac output. For example, applying intermittent BPR pulses may allow pulses with a higher (or even full) atrial kick to occur between BPR pulses. The pulses with a higher (or even full) atrial kick may prevent the BPR pulses from significantly lowering the cardiac output. In another embodiment, reducing adaptation that relates to lowering total peripheral resistance together with reduction of blood pressure (afterload) can positively affect cardiac output by affecting flow via the blood system. In yet another embodiment, pacing at a higher rate than the patient's natural rhythm may avoid a negative effect on cardiac output that might be associated with lower stroke volume.

In some embodiments, a time constant of the change in blood pressure of a given pattern may be calculated and the stimulation pattern may be set to have one or more BPR stimulation parameters for an amount of time or number of heartbeats that are set as a certain percentage of the calculated time constant. For example, in FIGS. 3A and 3B, k was measured to be about 15 sec for the rate of increase in blood pressure during delivery of a BPR pulses and about 4.9 sec for the rate of adaptation to the termination of the delivery of BPR pulses. In some embodiments, it may be desired to prevent blood pressure from increasing beyond a given value, in which case, the period of delivery of the BPR pulses may be selected to be significantly smaller than k (e.g., 30% to 60% of k). In this embodiment, the interval may be selected to be less than 15 sec. Such an interval may include about 6-10 sec or about 8-14 heartbeats where the heart rate is about 80 heartbeats per minute.

Optionally, it is desired to take advantage of the adaptation response to the withdrawal of BPR pulses. In such case, a greater portion of k might be applied. For example, based on FIG. 3B, a period of 3-5 heartbeats may be selected (where k is about 4.9 sec). Thus, for example, based on FIGS. 3A and 3B, the inventors applied the stimulation pattern of FIG. 4.

The stimulation pattern may be set, for example, to be the best of a plurality of stimulation patterns (i.e., the one closest to a set target parameter) and/or it may be selected as the first tested stimulation pattern that conformed to a set target.

Embodiments of Methods for Setting and/or Selecting a Stimulation Pattern

Figure 8:
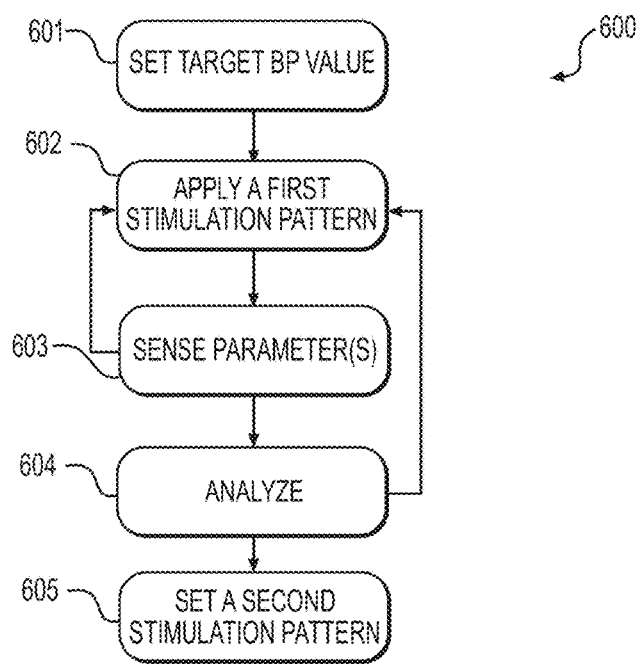
FIG. 8 is a flow chart showing an exemplary method for setting and/or selecting a stimulation pattern.

An exemplary method 600 for setting and/or selecting a stimulation pattern is schematically depicted in FIG. 8. Method 600 may be performed during implantation of a device for performing BPR and/or AC stimulation and/or periodically to adjust the device operation parameters and/or continuously during operation. Method 600 may be performed by system 700, described below. Accordingly, system 700 may be configured to perform any step of method 600. Similarly, method 600 may include any steps system 700 is configured to perform. For example, method 600 may include any of the functions discussed below with respect to system 700. Additionally, method 600 may be performed by device 50, described below in reference to FIG. 14. Method 600 may include any steps device 50 is configured to perform.

Throughout the present disclosure, the terms "first," "second," and "third" are not meant to always imply an order of events. In some cases, these terms are used to distinguish individual events from one another without regard for order.

In some embodiments, step 601 may include setting a target blood pressure value. This target may be an absolute blood pressure value (e.g., a target blood pressure range, a target threshold of spike value, and/or number or portion of spikes in a given timeframe), a relative value (e.g., as compared with the pre-treatment blood pressure of the patient or as a comparison between a plurality of tested stimulation patterns), or both. The target blood pressure value may be a blood pressure value (e.g., measured in mmHg) and/or a value associated with a formula calculated to match a blood pressure measurement of a stimulation pattern, etc. This target blood pressure value may be set before, during, and/or after the other method steps and it may also be amended, for example, if not reached by any tested simulation pattern.

Step 602 may include delivery of one or more stimulation patterns, including a first stimulation pattern, to one or more chambers of a patient's heart. The first stimulation pattern may be a generic stimulation pattern or the first stimulation pattern may already be selected to match a given patient (e.g., when implanting a replacement device). The first stimulation pattern may include at least one stimulation setting configured to reduce or prevent atrial kick in at least one ventricle and/or to control atrial pressure and/or stretch, for a first time interval.

Step 603 may include sensing one or more parameters before, during, and/or after the delivery of each of one or more stimulation patterns (step 602). The sensed parameter(s) may include sensing atrial pressure to assess an overlap between the maximum of atrial pressure due to contraction and the maximum of atrial pressure that is due to ventricular contraction. The sensed parameter(s) may include sensing atrial pressure as a result of delivery of each of one or more stimulation patterns (step 602), to assess a pressure obtained with the stimulation and optionally compare it with one or more of pressures obtained with a different stimulation or without stimulation. Optionally, the parameter(s) may include a blood pressure value or a blood pressure related parameter (e.g., a change in blood pressure). In some embodiments, the sensed parameter(s) may include information relating to the timing and/or extent of closure and/or opening of an AV valve. In some embodiments, the sensed parameter(s) may include information relating to the timing and/or rate of blood flow between an atrium and ventricle of the heart. In some embodiments, the sensed parameter(s) may include sensing pressure within a heart chamber (e.g., an atria and/or ventricle). In some embodiments, sensing of a patient's AV valve status, or position, (i.e., opened or closed) may include sensing of heart sounds, for example, using audio sensors. In some embodiments, sensing of a patient's AV valve status may include Doppler sensing and/or imaging of cardiac movement. In some embodiments, the patient's AV valve status may be sensed by a blood flow sensor.

In some embodiments, sensing of blood flow may be performed by one or more implanted sensors in one or more cardiac chambers. For example, one or more pressure sensors may be placed in the right ventricle. In some embodiments, a plurality of pressure sensors may be placed in a plurality of chambers. Optionally, measurements of a plurality of sensors may be combined. Optionally, pressure changes, trends of pressure changes, and/or pressure change patterns may be used to provide information relating to blood flow. In some embodiments, comparing relative changes between two or more sensors in different chambers may be used.

When a stimulation pattern is delivered to a heart (step 602), the one or more parameters may be measured at least once during delivery of the stimulation pattern or at a plurality of times or even continuously. Each stimulation pattern may be delivered more than once.

Step 604 may include analyzing the sensed parameter(s). In some embodiments, once at least one stimulation pattern is delivered and corresponding parameter(s) are sensed, analysis may be performed (604). In embodiments in which multiple parameters are sensed, step 604 may include the following: comparing sensed parameter values to a target; comparing sensed parameters between two or more stimulation patterns; comparing calculated values (e.g., the k constant) relating to two or more stimulation patterns; and comparing additional sensed parameters between two or more stimulation patterns. In some embodiments, this last function may be performed to determine and select which stimulation pattern yields a higher ejection fraction, stroke volume, cardiac output, and/or a lower battery use.

Step 605 may include setting a pacing (stimulation) pattern. When more than one parameter is sensed, the stimulation pattern used in step 605 may be selected based on the plurality of parameters, a plurality of target values, and/or a plurality of target ranges.

In some embodiments, the steps shown in FIG. 8 may be performed in the order shown by the arrows in FIG. 8. In other embodiments, the steps may be performed in another order. For example, step 602 may be performed before setting a target blood pressure value in accordance with step 601. In some embodiments, a stimulation pattern may be set to be performed indefinitely. In some embodiments, a stimulation pattern may be set to be performed for a predetermined period of time. For example, in some embodiments, the stimulation pattern set during step 605 may be performed for a predetermined period of time and then step 602, step 603, and step 604 may be repeated to determine how another stimulation pattern affects the patient's blood pressure. Then, based on the analysis performed in step 604, step 605 may also be repeated.

In some embodiments, method 600 may include a step of adjusting a first stimulation pattern, thus making the first stimulation pattern into a second stimulation pattern. In some embodiments, step 605 of setting a stimulation pattern may include adjusting a stimulation pattern. For example, step 605 may include adjusting a parameter of a first stimulation setting, e.g., the time interval from step 602. In another embodiment, step 605 may include adjusting a parameter of a first stimulation setting configured to reduce or prevent the atrial kick in at least one ventricle and/or to control atrial pressure and/or stretch. In some embodiments, step 605 may include adjusting first stimulation pattern to be a second stimulation pattern configured to cause a reduction in blood pressure by at least a predetermined amount. In some embodiments, the predetermined amount may include, for example, about 8 mmHg to about 30 mmHg. In some embodiments, the predetermined amount may be at least 4% of a patient's pretreatment blood pressure. For example, the predetermined amount may be about 4% of a patient's pretreatment blood pressure to about 30% of a patient's pretreatment blood pressure.

In some embodiments, step 605 may include adjusting the stimulation pattern to be a stimulation pattern configured to cause an immediate reduction in blood pressure by at least a predetermined amount. For example, in some embodiments, step 605 may include adjusting the stimulation pattern to be a stimulation pattern configured to cause a reduction in blood pressure by at least a predetermined amount within about 3 sec from an application of electricity to the heart. In some embodiments, step 605 may include adjusting the stimulation pattern to be a stimulation pattern configured to cause a reduction in blood pressure by at least a predetermined amount within at least 5 heartbeats of the applied electricity. In some embodiments, the reduction in blood pressure resulting from a stimulation pattern set during step 605 may occur within 1-3 sec of the application of electricity to the heart or within 1, 3, or 5 heartbeats of the application of electricity to the heart.

In some embodiments, the reduction in blood pressure resulting from a stimulation pattern set during step 605 may be such that a patient's average blood pressure at rest is at least 8 mmHg below the patient's initial blood pressure at rest. In some embodiments, the reduction in blood pressure resulting from a stimulation pattern set during step 605 may be maintained for at least 1 minute. In some embodiments, the reduction in blood pressure resulting from a stimulation pattern set during step 605 may be maintained for at least 5 minutes. In some embodiments, the blood pressure may reach a minimal blood pressure value within less than 5 heartbeats from the beginning of stimulation. For example, step 605 may include adjusting a first stimulation pattern to be a second stimulation pattern configured to cause a reduction in blood pressure. In some embodiments, step 605 may include adjusting the first stimulation pattern to a second stimulation pattern configured to cause a reduction in blood pressure for a predetermined time interval. For example, the predetermined time interval may include at least 1 minute or at least 5 minutes.

In some embodiments, the second stimulation pattern may be configured to maintain a blood pressure that does not exceed a predetermined average value during the predetermined interval by more than a predetermined degree. For example, the predetermined degree may be a difference of about 20 mmHg or less. In some embodiments, the predetermined degree may be a difference of about 1 mmHg to about 8 mmHg. In some embodiments, a patient's blood pressure may exceed a predetermined average value for some heartbeats, but the patient's average blood pressure may not exceed the predetermined average value.

In some embodiments, the second stimulation pattern may include a second stimulation setting configured to reduce or prevent the atrial kick in at least one ventricle and/or to control atrial pressure and/or stretch. The second stimulation setting may be based upon at least one blood pressure variation parameter calculated from an input data sensed during application of the first stimulation pattern.

In some embodiments, the second stimulation pattern may be configured to reduce or limit the magnitude of spikes in blood pressure between stimulation pulses. In some embodiments, the spikes in blood pressure between stimulation pulses may be reduced to a percentage of a baseline blood pressure value. For example, the second stimulation pattern may be configured to prevent more than an 80% increase in blood pressure between pulses. In other words, the second stimulation pattern may be configured to prevent the blood pressure from spiking more than about 80% between pulses. In some embodiments, the second stimulation pattern may be configured to prevent more than a 40% increase in blood pressure between pulses. In some embodiments, the second stimulation pattern may be configured to prevent a blood pressure spike of more than about 10 mmHg to about 30 mmHg between pulses. For example, in some embodiments, the second stimulation pattern may be configured to prevent a blood pressure spike of more than 20 mmHg between pulses.

In some embodiments, the second stimulation pattern may comprise multiple stimulation pulses. At least one stimulation pulse of the multiple stimulation pulses may have a first stimulation setting configured to reduce atrial kick in at least one ventricle and/or to control atrial pressure and/or stretch. At least one stimulation pulse of the multiple stimulation pulses may have a second stimulation setting configured to reduce the baroreflex response to the reduction in atrial kick or to the control of atrial stretch such that the increase in blood pressure values occurring between stimulation pulses is limited to a predetermined value. In some embodiments, the second stimulation setting may be configured to increase blood pressure for about 1 heartbeat to 5 heartbeats to invoke negation of the baroreflex response. In some embodiments, the second stimulation pattern may include multiple stimulation pulses having the first stimulation setting and multiple stimulation pulses having the second stimulation setting. In such embodiments, between about 1% of the multiple stimulation pulses and 40% of the multiple stimulation pulses of the stimulation pattern may have the second stimulation setting. In some embodiments, the second stimulation pattern may include multiple stimulation pulses having the first stimulation setting and multiple stimulation pulses having the second stimulation setting. In such embodiments, between about 1% of the multiple stimulation pulses and 40% of the multiple stimulation pulses of the stimulation pattern may have the second stimulation setting. In some embodiments, the stimulation pattern may include a ratio of stimulation pulses having the first setting to the stimulation pulses having the second setting based on a ratio of time constants of the response to increase and decrease in blood pressure. For example, the ratio of stimulation pulses having the first setting to the stimulation pulses having the second setting may be based on a ratio of the time constants of the changes in blood pressure resulting from each of the first setting and the second setting. In some embodiments, the first stimulation setting may include a first AV delay and the second stimulation setting may include a second AV delay, the first AV delay being shorter than the second AV delay. In some embodiments, the second stimulation pattern may include multiple stimulation pulses having the first stimulation setting and one or more stimulation pulses having the second stimulation setting. In some embodiments, the second stimulation pattern may include a ratio of about 8 stimulation pulses to about 13 stimulation pulses having the first setting to about 2 stimulation pulses to about 5 stimulation pulses having the second setting. In some embodiments, the second stimulation pattern may include at least one stimulation pulse having a stimulation setting configured to invoke a hormonal response from the patient's body. In some embodiments, the first stimulation pattern may include at least one stimulation pulse having a stimulation setting configured not to invoke a hormonal response from the patient's body. In some embodiments, the second stimulation pattern may be applied before the first stimulation pattern in a given sequence of stimulation patterns.

In some embodiments, method 600 may include alternating between two or more stimulation patterns. For example, method 600 may include alternating between two to ten stimulation patterns.

In some embodiments, the blood pressure sensor and the controller may be configured to operate at least partially as a closed loop.

In some embodiments, method 600 may include the controller executing a plurality of stimulation patterns and receiving for each of the stimulation patterns a corresponding input data relating to a patient's blood pressure during the stimulation. The plurality of stimulation patterns may include at least two stimulation patterns each comprising at least one stimulation pulse having a stimulation setting configured to reduce or prevent the atrial kick in at least one ventricle and/or to control atrial pressure and/or stretch. The at least two stimulation patterns may differ from one another by the number of times or the length of time the at least one stimulation pulse is provided in sequence. The at least two stimulation patterns may differ from one another by the number of times or the length of time a predetermined AV delay occurs in sequence. In some embodiments, the stimulation setting may be identical in each of the at least two stimulation patterns. In some embodiments, the stimulation setting may include an identical AV delay for each of the at least two stimulation patterns. In some embodiments, the at least two stimulation patterns may differ from one another by one or more stimulation settings included within each of the at least two stimulation patterns.

In some embodiments, method 600 may include the controller calculating for each of the plurality of stimulation patterns at least one blood pressure variation parameter relating to the input data. Method 600 may include the controller adjusting the stimulation pattern according to the blood pressure variation parameter. In some embodiments, method 600 may include the controller adjusting the stimulation pattern to be the stimulation pattern with the best blood pressure variation parameter. For example, the best blood pressure variation parameter may include the blood pressure variation parameter that displays the lowest degree of baroreflex. The best blood pressure variation parameter may include the blood pressure variation parameter that displays a baroreflex within a predetermined range.

In some embodiments, the second stimulation pattern may include at least one stimulation pulse having a stimulation setting configured to invoke a hormonal response from the patient's body, while in some embodiments, the first stimulation pattern may include at least one stimulation pulse having a stimulation setting configured not to invoke a hormonal response from the patient's body.

In some embodiments, the plurality of stimulation patterns may include a first stimulation pattern and a second stimulation pattern executed after the first stimulation pattern. The second stimulation pattern may have at least one stimulation setting that was set based on an algorithm using blood pressure variation parameters relating to the input data of the first stimulation pattern.

Embodiments of Systems for Reducing Blood Pressure

Figure 9:
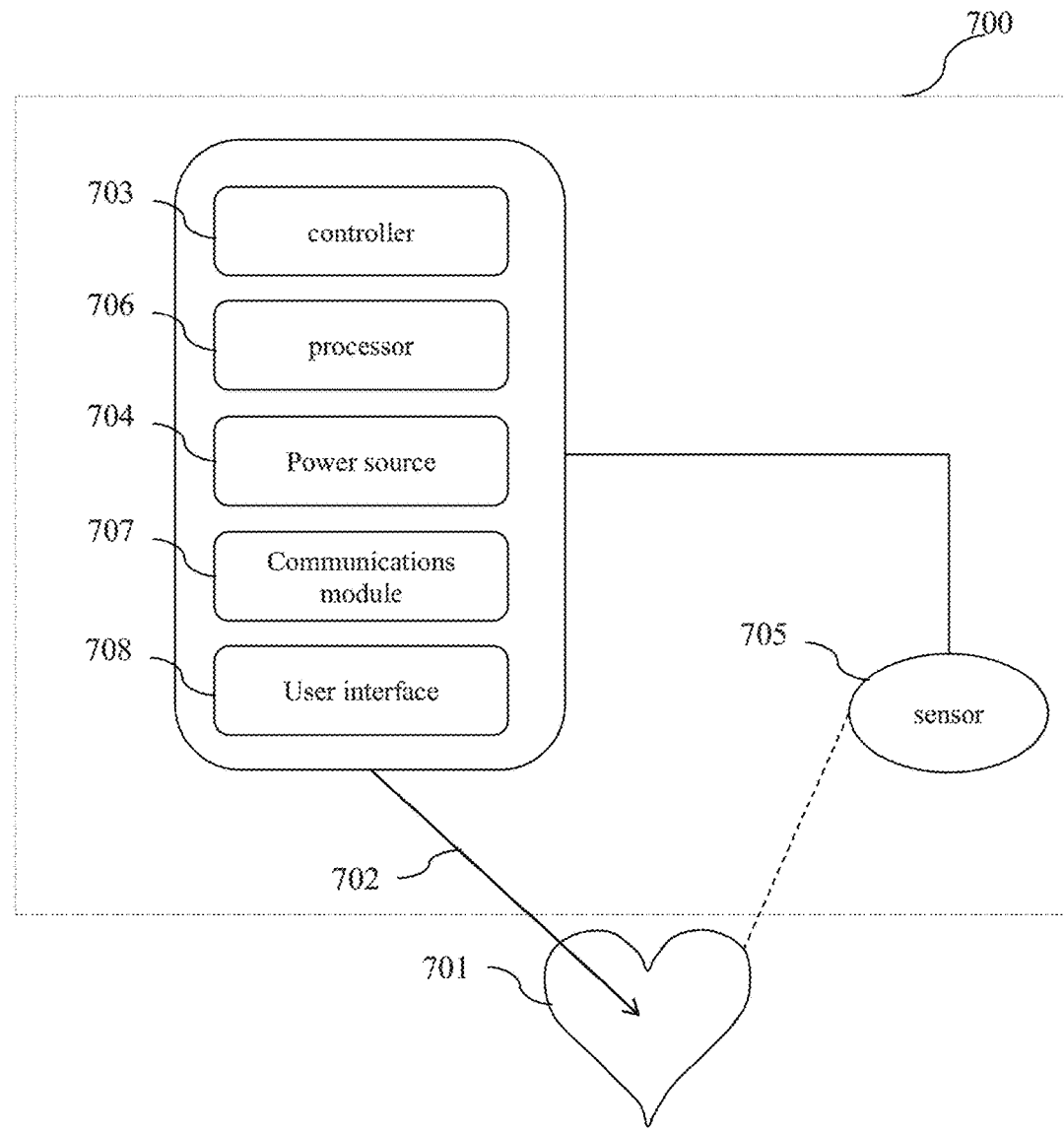
FIG. 9 is a schematic diagram illustrating an exemplary system for reducing blood pressure.

FIG. 9 schematically depicts an exemplary system 700 for reducing blood pressure according to some embodiments. System 700 may be a device or may comprise a plurality of devices, optionally associated by wire or wireless communication. The device(s) may have multiple components disposed inside a housing and/or connected to the housing electronically and/or by wires. As shown in FIG. 9, a heart 701 is connected to a system 700 by one or more stimulation electrodes 702. The stimulation electrode(s) may be configured to stimulate at least one chamber of a heart of a patient with a stimulation pulse. In some embodiments, multiple electrode(s) 702 may each be positioned in a different chamber of the heart. For example, one electrode may be positioned in an atrium and another electrode may be positioned in a ventricle. In some embodiments, multiple electrodes 702 may be positioned in a single chamber. For example, two electrodes may be positioned in an atrium and/or two electrodes may be positioned in a ventricle. In some embodiments, one electrode may be positioned in a first chamber and multiple electrodes may be positioned in a second chamber.

In the present embodiment, the electrode(s) 702 may include typical cardiac pacemaker leads, such as the Medtronic Capsure® pacing leads. These leads are used to connect the heart 701 to system 700. The pacing leads may be constructed with an industry standard IS-1 BI connector at one end (reference standard ISO 5148-3:2013), electrodes at the other end, and an insulated conductor system between them. In some embodiments, the IS-1 BI connector is constructed using stainless steel for the two electrode contacts and silicone as an insulating material. Some embodiments may use polyurethane as an insulating material.

Stimulation of one or more cardiac chambers may be accomplished by placing a voltage between the two electrodes of the atrial or ventricular cardiac pacing leads described above. The stimulation circuit uses a network of transistors (e.g., MOSFETS) to charge a capacitor to a specific programmable voltage, such as 2.0V, and then control its connection to the electrodes for a fixed period of programmable time, such as 0.5 ms. The same network may also manage a discharge of any residual charge that may be accumulated on the electrodes after stimulation is complete. The same network may control the type of stimulation applied, such as bipolar (between the two electrodes) or unipolar (between one electrode and the stimulator housing).

One or more electrodes may be placed in contact with one or both ventricles and/or one or both atria, as known in the art. Such electrodes may be used to sense and/or deliver stimuli to the respective cardiac chamber(s). For example, pacing electrodes can be introduced to both ventricles, with one electrode implanted into the right ventricle and an additional electrode placed on the left ventricle through the coronary sinus, and with the system 700 including means to generate biventricular stimulation of both ventricles in order to reduce dyssynchrony caused by ventricular stimulation.

System 700 may include a controller 703. System 700 may be an electrical stimulator including a power source 704 (e.g., a battery as known in the art of electrical stimulators). Controller 703 and/or electrode(s) 702 may draw power from power source 704.

Optionally, the electrical stimulator of system 700 is constructed of a hermetically sealed housing and a header. The housing may be constructed of titanium or any other biocompatible material, and may contain a power source 704, electronics, and a telemetry coil or communication module 707 for communication with an external device. The power source 704 may be an implantable grade, hermetically sealed, primary battery. The battery chemistry may be lithium-iodine. Other embodiments may use larger or smaller batteries. Other embodiments may use rechargeable batteries such as Li-ion rechargeable batteries. The electronics in some embodiments may be constructed of standard off-the-shelf electronics (e.g., transistors and diodes) and/or custom electronics (e.g., ASIC).

In order to detect the onset of atrial excitation and/or ventricular excitation, one or more sensing electrodes may be implanted at or near a site of interest in the heart. These sensing electrodes may be the same electrodes used for delivering pulses to the heart or dedicated sensing electrodes. The electrical activity may be band-pass filtered to remove unwanted noise and may conform to an international standard for cardiac pacemakers (reference EN45502-2-1: 2003), with programmable cutoff frequencies. An electrical circuit may be used to amplify the electrical signals generated by a propagating activation of the cardiac chamber and to determine the onset of activation once the electrical signals fulfill specified criteria, for example, crossing of a predefined threshold. The signal may, for example, be amplified, with programmable gains, and then passed to a comparator for threshold detection, with programmable detection thresholds in steps of 0.2 mV (atrial) and 0.4 mV (ventricle). These means of detecting excitation may introduce a delay between the actual onset of activation in the chamber and its detection, since the detecting electrodes may be away from the origin of excitation and the time it takes for the signal to fulfill the detection criteria might not be negligible and may be in the range of 5 to 50 ms or even more. In such cases, the timing of the onset of excitation may be estimated based on the timing of a sensed excitation, and the delivery of stimulation pulses would be calculated to compensate for this delay.

Optionally, the controller 703 interfaces with an accelerometer to measure patient activity level. This patient activity level may be used to adjust the pacing rate and/or BPR settings and/or the stimulation pattern based upon the patient's needs. Activity level may also be used to control a desired level of effect on blood pressure. For example, reduction in blood pressure may be reduced at high levels of activity to enable better performance when an increase in blood pressure is required. Optionally, when a patient is inactive (e.g., when sleeping) blood pressure may reduce naturally, in which case pacing may be adjusted in order to avoid reducing blood pressure below a desired threshold. Activity level may also be used to adjust settings based on baroreflex to allow better response when needed. The sensor may be, for example, a piezoelectric sensor. Other embodiments may use a MEMS-based accelerometer sensor. Other embodiments may use a minute ventilation sensor, optionally in combination with an accelerometer.

Controller 703 may be configured to deliver electricity to the heart 701 via one or more electrodes 702. Controller 703 may be configured to execute a stimulation pattern of stimulation pulses according to any embodiment of this disclosure. In some embodiments, the stimulation pulses may be delivered to at least a ventricle of the heart. In some embodiments, the stimulation pattern may include a first stimulation setting and a second stimulation setting different from the first stimulation setting, with the first stimulation setting and the second setting configured to reduce or prevent the atrial kick and/or to control atrial pressure and/or stretch. In some embodiments, the first stimulation setting has a different AV delay than the second stimulation setting. In some embodiments, the first stimulation setting and/or the second stimulation setting may be configured such that an atrial pressure resulting from atrial contraction of an atrium overlaps in time a passive pressure build-up of the atrium, thereby providing an atrial pressure of the atrium that is a combination of the atrial pressure resulting from atrial contraction and the passive pressure build-up and is higher than an atrial pressure of the atrium would be without the stimulation. In some embodiments, the first stimulation setting and/or the second stimulation setting may be configured such that maximum atrial stretch is at a value that is about equal to or lower than the maximum atrial stretch of the same heart when not receiving stimulation. In some embodiments, the first stimulation setting and/or second stimulation setting are configured to cause an atrium to be at maximum contraction force when the AV valve is open. In some embodiments, the first stimulation setting and/or second stimulation setting are configured to alter the mechanics of at least one atrial contraction such that the mechanics of the at least one atrial contraction are different from the mechanics of a previous natural atrial contraction. In some embodiments, the first stimulation setting and/or second stimulation setting are configured to reduce the force of at least one atrial contraction. In some embodiments, the first stimulation setting and/or second stimulation setting are configured to prevent at least one atrial contraction.

In some embodiments, the controller 703 may be configured to deliver a variety of different AV delays. The controller 703 may be configured to sense when the atrial contraction or excitation occurs (as described herein) and then deliver ventricular stimulation a fixed interval after that or before a future anticipated atrial excitation or contraction. The interval may be programmable. The controller 703 may also be configured to stimulate the atrium and then deliver ventricular stimulation at a fixed interval after that, which may also be programmable. The programmable interval may, for example, be changed between 2 ms and 70 ms to accommodate a desired therapeutic effect or even provide a negative AV delay of up to −50 ms.

In some embodiments, controller 703 may be configured to repeat a stimulation pattern multiple times. For example, controller 703 may repeat a stimulation pattern twice. In another embodiment, controller 703 may be configured to repeat a stimulation pattern at least twice in a period of an hour. The stimulation pattern repeated by controller 703 may include any type of stimulation pattern. For example, the stimulation pattern may include a stimulation setting configured to reduce or prevent the atrial kick in at least one ventricle and/or to control atrial pressure and/or stretch. In another embodiment, the stimulation pattern may include two different stimulation settings each configured to reduce or prevent the atrial kick in at least one ventricle and/or to control atrial pressure and/or stretch. These two stimulation settings may differ by one or more parameters, for example, by AV delay.

In some embodiments, controller 703 may be configured to execute one or more consecutive stimulation patterns for a predetermined time interval. For example, in some embodiments, the time interval may be 10 minutes or longer. In another embodiment, the time interval may be 30 minutes or longer, one hour or longer, or 24 hours or longer. In some embodiments, the time interval may be a period of months, such as one month to one year. In some embodiments, the time interval may be longer than one year. In some embodiments, the one or more consecutive stimulation patterns may include a first stimulation setting configured to reduce or prevent the atrial kick in at least one ventricle and/or to control atrial pressure and/or stretch, for a portion of the time interval. For example, the one or more consecutive stimulation patterns may include a first stimulation setting configured to reduce or prevent the atrial kick in at least one ventricle and/or to control atrial pressure and/or stretch, for about 50% of a time interval to about 100% of the time interval. In another embodiment, the one or more consecutive stimulation patterns may include a first stimulation setting configured to reduce or prevent the atrial kick in at least one ventricle and/or to control atrial pressure and/or stretch, for about 50% of a time interval to about 85% of the time interval. In some embodiments, the one or more consecutive stimulation patterns may include a second stimulation setting having a longer AV delay than the first stimulation setting for at least one heartbeat during the time interval. In some embodiments, the one or more consecutive stimulation patterns may include a second stimulation setting and/or a third stimulation setting. The second stimulation setting and/or third stimulation setting may each be different from the first stimulation setting. In some embodiments, the second stimulation setting and/or third stimulation setting may each be configured to reduce or prevent the atrial kick in at least one ventricle and/or to control atrial pressure and/or stretch. In some embodiments, the second stimulation setting and/or third stimulation setting may each be configured not to reduce or prevent the atrial kick in at least one ventricle and/or not to control atrial pressure and/or stretch. In some embodiments, the second stimulation setting and/or third stimulation setting may include about 0% of a time interval to about 50% of the time interval. In some embodiments, the second stimulation setting and/or third stimulation setting may include about 0% of a time interval to about 30% of the time interval. In some embodiments, the second stimulation setting and/or third stimulation setting may include about 0% of a time interval to about 20% of the time interval. In some embodiments, the second stimulation setting and/or third stimulation setting may include about 5% of a time interval to about 20% of the time interval.

Blood pressure is known to vary in a circadian manner, and in some cases abnormally high blood pressure is prevalent only or mostly during part of a 24-hour period (e.g., nighttime or daytime or parts thereof). Additionally, blood pressure is known to vary according to physical activity, with an active person having a higher blood pressure than the same person at rest. In some cases, it may thus be desired to control the delivery of treatment according to need, for example, by changing therapy parameters or even withholding the delivery of cardiac stimulation to reduce blood pressure. In other words, at different times of the day and/or when a patient is active or at rest, cardiac stimulation may be changed to adjust parameters of the stimulation, or may be simply turned on/off. Optionally, the delivery of such stimulation may be controlled according to the time of day and adjusted to a patient's circadian BP rhythm.

Figure 21:
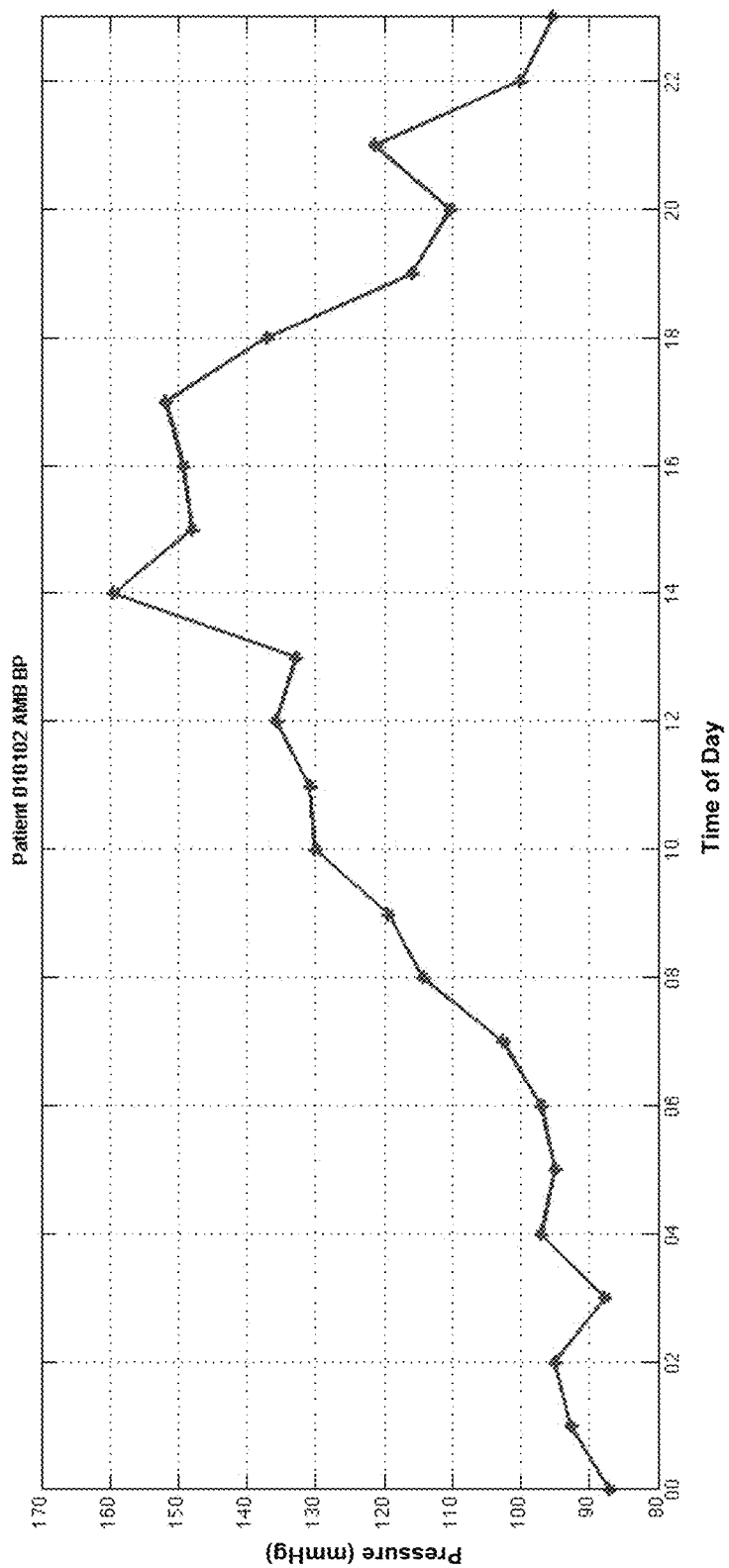
FIG. 21 is a graph plotting a patient's average blood pressure during a 24-hour period.

For example, FIG. 21 shows the systolic BP of an untreated patient during a 24-hour period of monitoring. An hourly average is presented. As shown, the patient's BP was abnormally high only during the day (circa 10 a.m. to 6 p.m.). In such types of cases, it may be preferred to set a device to deliver pulses configured to reduce atrial kick and/or to provide AC stimulation only during the time of day when BP is expected to be abnormally high (i.e., when there is a need or where a need is expected).

Figure 22:
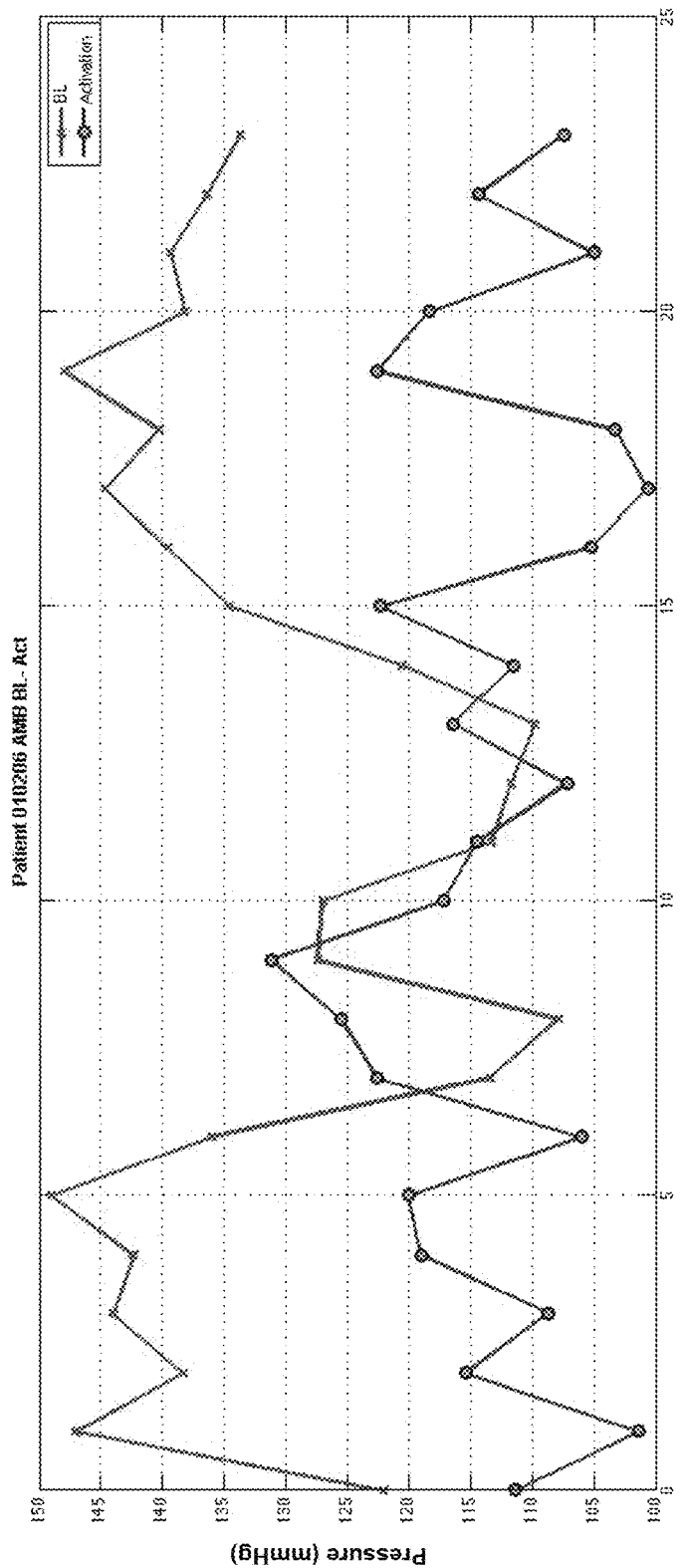
FIG. 22 is a graph plotting a patient's average blood pressure during a 24-hour period, when not treated and when treated according to an embodiment.

Another example is shown in FIG. 22. Here a patient's untreated blood pressure (represented in FIG. 22 by the line with "x" data points) was shown to be abnormally high during the night (after 2 p.m. and before 7 a.m.). An increase in BP during the day was within normal range and may be attributed to an increase in patient activity. Optionally, it may be assumed that this patient would be in need of treatment only during the night, and a device may be set to deliver stimulation accordingly. Optionally it may be assumed that the patient does not need treatment during the day, and a device may be set such that even if an increase in blood pressure is measured during the day, such increase should not elicit the delivery of treatment to reduce blood pressure. Optionally, the device may be set not to measure blood pressure during the day. In the example shown in FIG. 22, the patient was then treated with a blood pressure reducing pulse having the following setting: pacing both an atrium and ventricle with an AV delay of 15 ms for 10 heartbeats followed by pacing the atria and the ventricle for 3 heartbeats with an AV delay of 40 ms. The therapy was delivered every day starting at 3 p.m. and lasting 13 hours. The resulting BP was plotted (represented in FIG. 22 by the with circle data points), and as can be seen, BP was within normal range essentially throughout the day and displayed much less variation than it did during pre-treatment (under treatment, BP varied by no more than about 30 mmHg, while the untreated range varied by more than 40 mmHg).

In some embodiments, an intrinsic (without stimulation) blood pressure profile of a patient is first determined, and based on that intrinsic profile, stimulation parameters that generate a desired reduction in blood pressure are then determined accordingly. FIG. 22 illustrates one example of such an approach. In some embodiments, blood pressure is measured continuously or intermittently during operation of the device, and the stimulation parameters that generate a desired reduction in blood pressure are then determined accordingly.

In some embodiments, controller 703 may be configured to execute one or more consecutive stimulation patterns including a sequence of 10-60 stimulation pulses having a first stimulation setting configured to reduce or prevent the atrial kick in at least one ventricle and/or to control atrial pressure and/or stretch. In some embodiments, controller 703 may be configured to execute one or more consecutive stimulation patterns including a sequence of 1-10 heartbeats embedded within the 10-60 stimulation pulses and the sequence of 1-10 heartbeats may have a longer AV delay than the first stimulation setting. For example, the 10-60 stimulation pulses may include 5 stimulation pulses having the first stimulation setting, followed by one heartbeat having a longer AV delay than the first stimulation setting, followed by 50 stimulation pulses having the first stimulation setting. The sequence of 1-10 heartbeats may include at least one stimulation pulse having a first stimulation setting configured to reduce or prevent the atrial kick in at least one ventricle and/or to control atrial pressure and/or stretch. The sequence of 1-10 heartbeats may include a natural AV delay. The sequence of 1-10 heartbeats may occur without stimulation.

System 700 may further comprise one or more sensors 705. In some embodiments, such sensor(s) 705 may include one or more sensing electrode(s) for sensing electrical activity of the heart. In some embodiments, one or more sensing electrode(s) may include one or more stimulation electrode(s) 702. In some embodiments, sensor(s) 705 may include one or more blood pressure sensors (implantable and/or external). In some embodiments, one or more sensors 705 may include one or more pressure sensors implanted in the heart (e.g., in the atria and/or ventricle). In some embodiments, sensor(s) 705 may include one or more blood flow sensors (implantable and/or external). For example, one or more sensors 705 may include ultrasound sensing of blood flow through the AV valve. In some embodiments, sensor(s) 705 may include one or more sensors configured to monitor the timing of closure of the AV valve. One or more of these sensors may be configured to operate as a closed loop with the controller.

Information from sensor(s) 705 may be provided to controller 703 by any form of communication, including wired communication and/or wireless communication. Optionally, system 700 may comprise one or more communication modules 707 for receiving and/or transmitting information between system components and/or to devices that are external to the system. In some embodiments, controller 703 may be configured to receive input data relating to the patient's blood pressure. For example, the input data relating to the patient's blood pressure may include data indicative of BP measured at one or more points in time or of a variation in BP (e.g., a degree of change and/or a rate of change or a function describing the change of blood pressure over time) and/or statistical data relating to BP or variation in BP, maximum and/or minimum BP values Optionally, system 700 may comprise one or more user interfaces 708 for providing information and/or for allowing input of information. Providing information may include, for example, a display of operational information relating to the system and/or data that was recorded by the system and/or received by the system during operation. This may include sensed parameter(s) and/or a relation between sensed parameter(s) and operational information (such as stimulation pattern settings and/or relative timing between delivery of a given pace and sensed information).

Optionally, user interface 708 may be comprised of a commercially available laptop computer (e.g., Windows®-based computer) running a software application. The software application may serve to generate orders to be delivered to an interface that is, in turn, connected to a hand-held wand that contains a telemetry circuit for communication with the implantable stimulator. The orders sent to the wand may be used to set stimulation parameters and/or to retrieve device diagnostics, device data, cardiac data, and real-time cardiac sensing. The interface also allows for connection of a 3-lead ECG and this data is displayed on the laptop computer screen by the software application. Other embodiments may not include the 3-lead ECG circuitry or may include 12-lead ECG circuitry. Other embodiments may incorporate the functionality of the wand, interface, and laptop computer into a dedicated piece of hardware that performs all three functions. Other embodiments may also add printing capability to the user interface 708.

In some embodiments, interface(s) 708 may be configured such that a user (e.g., medical practitioner) may provide a set of control instructions to the system (e.g., target values and/or ranges and/or other limitations or instructions). Optionally, interface(s) 708 may allow a user to input data from one or more sensors 705 (e.g., the results of a manual blood pressure measurement and/or results of an ultrasound monitor).

Optionally, the one or more user interfaces 708 may allow a user to select a stimulation pattern (for example, from a set of stimulation patterns stored in system 700) or impose constraints on the setting and/or selecting of a stimulation pattern.

Optionally, system 700 may comprise one or more processors 706. Processor(s) may be configured to process sensed parameters from sensor(s) 705 and/or input data from user interface(s) 708 to select a stimulation pattern for delivery by system 700. Optionally, processor(s) 706 may be configured to analyze sensed parameters and extract information and/or formula constants to be used in the selection and/or evaluation of stimulation patterns.

One or more components of system 700 or portions of such components may be implanted in the patient, while some components of system 700 or portions of such components may be external to the patient. When some components (or component parts) are implanted and others are not, communication between the components may take place by wired and/or wireless means, essentially as known in the art. For example, some or all functions of both controller 703 and/or processor 706 may be performed outside the body. Having some components of system 700 external to the patient's body may assist in reducing the size and/or energy requirements of an implanted device, and/or in the enhancement of the system's computation capabilities.

System 700 may include additional functions relating to control of heart function and overall cardiovascular system performance. For example, system 700 may include one or more algorithms and/or electrodes to enable biventricular pacing or resynchronization therapy to reduce dyssynchrony that may be caused by ventricular stimulation. In some embodiments, system 700 may include one or more algorithms to compensate for a possible reduction in cardiac output. Such an algorithm that may change heart rate in order to increase cardiac output or implement other methods known in the art for controlling cardiac output. In some embodiments, system 700 may include rate response algorithms to affect changes in heart rate as a response to certain circumstances. For example, system 700 may include rate response algorithms to affect changes in heart rate as a response to changes in level of exercise, ventilation activity, and/or oxygen consumption. In some embodiments, system 700 may include a sensor that detects activity and the algorithm may turn off stimulation while a patient is exercising such that a patient's blood pressure is not reduced. In some embodiments, system 700 may include a real-time clock. Such a clock may be used to control the timing of the stimulation. For example, system 700 may include an algorithm that turns stimulation on and off depending upon the time of day. This type of algorithm may be used to prevent hypotension during the night when a patient is sleeping.

In some embodiments, a kit including one or more components of system 700 and a set of instructions for adjusting the stimulation pattern based on input relating to a patient's blood pressure may be provided.

Some embodiments may provide a system for reducing blood pressure configured to deliver stimulation at a rate higher than the natural heart rate based on sensed natural heart rate or natural excitation. For example, the system may be configured to sense the natural excitation between delivery of stimulation pulses and if a natural activity is sensed, the system may be configured to inhibit the delivery of the stimulation pulse to the chamber. If in a given time frame the amount of sensed activations exceeds a threshold, the natural heart rate may be regarded as higher than the rate of delivery of the stimulation pulses, in which case the rate of delivery may be increased, e.g., to accommodate increased heart rate of a patient. On the other hand, if in a given time frame the amount of sensed activations is lower than a threshold (this threshold may be 0), the natural heartbeat may be regarded as lower than the rate of delivery of the stimulation pulses, in which case the rate of delivery may be reduced, e.g., to avoid over excitation of a patient's heart. To achieve this effect, according to one embodiment, a system for reducing blood pressure may include a sensor for sensing an excitation rate of at least one of an atrium and a ventricle of a patient's heart, a stimulation circuit configured to deliver stimulation pulses to an atrium and a ventricle, and a processor circuit coupled to the stimulation circuit. The processor circuit may be configured to detect the patient's heart rate based on the sensing and operate in an operating mode in which a stimulation pulse is provided to each of the at least one of an atrium and a ventricle. The stimulation pulse may be delivered at a rate that is higher than the sensed excitation rate and may be configured to stimulate the ventricle at a time between about 50 ms before and about 70 ms after stimulation of the atrium.

Some embodiments may provide a system for reducing blood pressure based on a predicted next atrial contraction. For example, a system for reducing blood pressure may include a sensor for sensing an excitation rate of at least one of an atrium and a ventricle, a stimulation circuit configured to deliver a stimulation pulse to at least one of an atrium and a ventricle, and a processor circuit coupled to the stimulation circuit. The processor circuit may be configured to operate in an operating mode in which a timing of a next atrial excitation is predicted based on the sensed excitation rate of the previous atrial excitations, and at least one ventricle is stimulated at a time between about 50 ms before and about 10 ms after the predicted next atrial excitation. The predicted timing may be based on the time interval between the two previous sensed atrial excitations and on a function that will be based on previously sensed time intervals between atrial excitations. The function may include the change in time interval, the rate of change in time intervals, and/or detection of periodic variations in time intervals (e.g., periodic variation due to breathing).

Optionally, a sensor for sensing the excitation rate of at least one of an atrium and a ventricle may comprise an electrode for sensing atrial excitation.

In a further aspect, prediction of a next atrial contraction may be based on a function of previous sensed excitations including rate of change of intervals and periodic variations.

In a further aspect, the timing of the predicted next atrial excitation may be adjusted to reflect a delay between an atrial excitation and a sensing of the atrial excitation.

In a further aspect, the system may further comprise an additional sensor for sensing a parameter relating to cardiac activity and for adjusting the time at which the ventricle is stimulated accordingly. The parameter may be a member of a group consisting of data relating to blood pressure, blood flow, AV valve status, and wall motion of the heart or a part thereof. The additional sensor may be selected from the group consisting of pressure sensors, impedance sensors, ultrasound sensors, and/or one or more audio sensors and/or one or more blood flow sensors. The additional sensor may be implantable.

Reducing Atrial Kick

Some embodiments stem from the inventors realization that blood pressure can be reduced by causing a closure of at least one AV valve during at least part of an atrial contraction. This will reduce, or even prevent, the contribution of the contraction of the atria to the filling of the ventricles, and thus reduce cardiac filling at the end of diastole and consequently reduce blood pressure.

In some embodiments, at least part of an atrial contraction may occur against a closed AV valve. For example, in some embodiments, 40% or more of an atrial contraction may occur against a closed AV valve. In some embodiments, at least 80% of an atrial contraction may occur against a closed AV valve. For example the contraction may start approximately 20 ms or less before the contraction of the ventricle or the excitation of the atria may occur 20 ms or less before the excitation of the ventricle. In some embodiments, 100% of an atrial contraction may occur against a closed AV valve, in which case ventricle excitation is timed such that ventricle contraction will begin before the commencement of atrial contraction. This may include exciting the ventricle before the onset of atrial excitation. The higher the percentage is of an atrial contraction that occurs with the AV valve closed, the more the atrial kick is reduced. Stimulation of both the atrium and the ventricle may provide better control of the percentage of an atrial contraction occurring against a closed valve. Various embodiments may be implemented to cause at least part of an atrial contraction to occur against a closed valve. For example, the AV valve may be closed 70 ms or less after the onset of mechanical contraction of the atrium or 40 ms or less after the onset of mechanical contraction of the atrium or even 5 or 10 ms or less after the onset of mechanical contraction of the atrium. In some embodiments, the AV valve may be closed before the onset of mechanical contraction of the atrium. For example, the AV valve may be closed within 5 ms before the onset of the mechanical contraction of the atrium. In some embodiments, the AV valve may be closed at the same time as the onset of the mechanical contraction. In some embodiments, the AV valve may be closed after the onset of the mechanical contraction of the atrium. For example, the AV valve may be closed within 5 ms after the onset of mechanical contraction of the atrium.

In some embodiments, the onset of a contraction of a chamber may be sensed and a stimulation pulse may be timed relative to the sensed onset of a contraction. The onset of contraction in a chamber is the start of active generation of contractile force in the chamber. The onset of contraction can be sensed by a rapid change in pressure that is not related to the flow of blood into the chamber. The onset of contraction may also be sensed by measuring the movement of the walls of a cardiac chamber or measuring the reduction in volume of a chamber using an ultrasound. These methods of sensing the onset of a contraction may have a delay between the actual onset of the contraction and the sensing of an onset of contraction.

In some embodiments, the AV valve may be closed after the onset of contraction of at least one atrium. For example, the AV valve may be closed about 0 ms to about 70 ms after the onset of contraction of at least one atrium. In some embodiments, the AV valve may be closed about 0 ms to about 40 ms after the onset of contraction of at least one atrium. In some embodiments, the AV valve may be closed about 0 ms to about 10 ms after the onset of contraction of at least one atrium. In some embodiments, the AV valve may be closed about 0 ms to about 5 ms after the onset of contraction of at least one atrium.

Typically, an atrial contraction may begin about 40 ms to about 100 ms after the onset of atrial excitation. In some embodiments, the AV valve may be closed after the onset of atrial excitation. For example, the AV valve may be closed about 40 ms to about 170 ms after the onset of atrial excitation. For example, the AV valve may be closed about 40 ms to about 110 ms after the onset of atrial excitation. In another embodiment, the AV valve may be closed about 40 ms to about 80 ms after the onset of atrial excitation. For example, the AV valve may be closed about 40 ms to about 75 ms after the onset of atrial excitation. For example, the AV valve may be closed about 40 ms to about 50 ms after the onset of atrial excitation.

In some embodiments, the onset of excitation in a chamber may be sensed and a stimulation pulse may be timed relative to the sensed onset of excitation. The onset of excitation is the initiation of a propagating action potential through a chamber. The onset of excitation may be sensed by sensing the local electrical activity of a chamber using a sensing electrode connected to an amplifier. The onset of excitation can also be detected by electrocardiography.

In some embodiments, methods of sensing the onset of excitation may have a delay between the actual onset of the excitation and the sensing of an onset of excitation. The timing of a sensed atrial excitation may be determined by taking into account the delay between actual onset of excitation and the sensing thereof. For example, if a sensing delay is estimated to be 20-40 ms, and stimulation pulses are to be delivered 0-70 ms after onset of atrial excitation, a system may be set to deliver pulses between 40 ms before the next anticipated sensing event to 30 ms after the next anticipated sensing event or 30 ms after the next sensing event. Likewise, if the stimulation pulses are to be delivered to the ventricle 0-50 ms before onset of atrial excitation, assuming the same 20-40 ms sensing delay, a system may be set to deliver pulses between 40 ms before the next anticipated sensing event to 90 ms before the next anticipated sensing event. Sensing delays may be due to one or more of a distance between the site of onset of excitation and a sensing electrode, the level of the electrical signal, characteristics of the sensing circuit, and the threshold set of a sensing event. The delay may include, for example, the duration of the signal propagation from the origin of excitation to the electrode location, the duration related to the frequency response of the sensing circuit, and/or the duration necessary for the signal propagation energy to reach a level detectable by a sensing circuit. The delay may be significant and can range, for example, between about 5 ms to about 100 ms. One approach for estimating the delay is to use the time difference between an AV delay measured when both atrium and ventricle are sensed and the AV delay when the atrium is paced and the ventricle is sensed. Other approaches may use calculation of the amplifier response time based on the set threshold, signal strength, and frequency content. Other approaches may include modifying the delay used with atrial sensing until the effect on blood pressure is the same as the effect obtained by pacing both atrium and ventricle with the desired AV delay.

In some embodiments, the AV valve may be closed before the onset of excitation or contraction of at least one atrium. For example, the AV valve may be closed within about 0 ms to about 5 ms before the onset of excitation or contraction of at least one atrium. In some embodiments, the AV valve may be closed at the same time as the onset of excitation or contraction of at least one atrium.

In some embodiments, direct mechanical control of AV valve closure may be performed. In such embodiments, a mechanical device or a portion thereof may be implanted in the patient, and operated to cause the closing of a valve between the atrium and ventricle. For example, an artificial valve may be implanted in the patient's heart and operated to close mechanically in accordance with some embodiments. In such embodiments, instead of or in addition to providing a stimulation pattern, the aforementioned closure of the AV valves may be accomplished by controlling the functioning of the implanted valve.

In some embodiments, a shortened or even negative time interval between the onset of atrial excitation and ventricular excitation is employed to reduce cardiac filling, thereby reducing blood pressure. As used herein, a negative time interval between the onsets of atrial excitation and ventricular excitation means that in a single cardiac cycle, the onset of excitation for the at least one ventricle occurs before the onset of atrial excitation. In this case, atrial contraction may take place, at least partially, against a closed AV valve, since the generated pressure in the ventricles may be greater than the pressure in the atria. A short time after the initiation of ventricular contraction, the pressure in the ventricles may exceed the pressure in the atria and may result in the passive closure of the valve. This closure of the valve may reduce or even obliterate the atrial kick and, in turn, reduce ventricular filling. Consequently, the force of ventricular contraction may be reduced and blood pressure may drop.

The time between the start of excitation and the start of the mechanical contraction in each cardiac chamber is not fixed. Thus, the timing of excitation does not guarantee the same effect on the timing between contractions. However, in some embodiments, the timing between excitations is used as a frame of reference for practical reasons. The ultimate purpose of controlling the timing of excitation is to control the timing of a contraction.

In some embodiments, a shortened or even negative time interval between the onset of atrial contraction and ventricular contraction may be employed to reduce cardiac filling, thereby reducing blood pressure. In this case, better control over the contribution of the atria may be obtained since the start of the contraction of the ventricle will result with the closure of the valve.

In some embodiments, 40% or more of an atrial contraction may occur during ventricular systole. For example, the atrial contraction may start approximately 60 ms or less before the contraction of the ventricle, or the excitation of the atria may occur 60 ms or less before the excitation of the ventricle. In some embodiments 80% or more of an atrial contraction may occur during ventricular systole. For example, the contraction may start approximately 20 ms or less before the contraction of the ventricle, or the excitation of the atria may occur 20 ms or less before the excitation of the ventricle. In some embodiments, 100% of an atrial contraction may occur during ventricular systole, in which case ventricle excitation is timed such that ventricle contraction will begin before the commencement of atrial contraction. This may include exciting the ventricle before the onset of atrial excitation.

Some embodiments provide a method for causing the contraction of at least one ventricle of a heart, such that the at least one ventricle contracts during or before the contraction of the corresponding atrium. One way to achieve this goal is by exciting the ventricle at a point in time between about 50 ms before to about 70 ms after the onset of excitation of the corresponding atrium. In some embodiments, the time interval between the onset of excitation of at least one ventricle and the onset of excitation of the corresponding atrium may be zero. In other words, the onset of excitation for the at least one ventricle may occur at the same time as the onset of excitation of the corresponding atrium. In some embodiments, the onset of excitation of the ventricle may occur between about 0 ms to about 50 ms before the onset of atrial excitation. In some embodiments, the onset of excitation of the ventricle may occur at least 2 ms before to at least 2 ms after the onset of excitation of the at least one atrium. In some embodiments, the onset of excitation of the ventricle may occur at least 10 ms before to at least 10 ms after the onset of excitation of the at least one atrium. In some embodiments, the onset of excitation of the ventricle may occur at least 20 ms before to at least 20 ms after the onset of excitation of the at least one atrium. In some embodiments, the onset of excitation of the ventricle may occur at least 40 ms before to at least 40 ms after the onset of excitation of the at least one atrium.

In some embodiments, a method may comprise delivering a stimulation pulse from a stimulation circuit to at least one of an atrium and a ventricle, and operating a processor circuit coupled to the stimulation circuit to operate in an operating mode in which a ventricle is stimulated to cause ventricular excitation to commence between about 0 ms and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. The time interval between the onset of atrial excitation and the moment that atrial excitation is sensed may be known and used to calculate the timing of the onset of atrial excitation. For example, if it is known that atrial excitation is sensed 20 ms after the onset of atrial excitation and the ventricle is to be stimulated 40 ms before the onset of atrial excitation, then the ventricle is to be stimulated 60 ms before the anticipated sensing of atrial excitation. In other embodiments, the method may comprise operating a processor circuit coupled to the stimulation circuit to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the processor circuit may be configured to operate in an operating mode in which one or more excitatory pulses are delivered to an atrium between about 0 ms and about 50 ms after one or more excitatory pulses are provided to the patient's ventricle. In such embodiments, the pacing may be timed without relying on sensing atrial excitation. Optionally, in such embodiments atrial excitation is sensed in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

In some embodiments, a device may comprise a stimulation circuit configured to deliver a stimulation pulse to at least one of an atrium and a ventricle. The device may comprise a processor circuit coupled to the stimulation circuit. The processor circuit may be configured to operate in an operating mode in which a ventricle is stimulated to cause ventricular excitation to commence between about 0 ms and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. The time interval between the onset of atrial excitation and the moment that atrial excitation is sensed may be known and used to calculate the timing of the onset of atrial excitation. For example, if it is known or estimated that atrial excitation is sensed 20 ms after the onset of atrial excitation and the ventricle is to be stimulated 40 ms before the onset of atrial excitation, then the ventricle is to be stimulated 60 ms before the anticipated sensing of atrial excitation. In other embodiments, the processor circuit may be configured to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the processor circuit may be configured to operate in an operating mode in which one or more excitatory pulses are delivered to an atrium between about 0 ms and about 50 ms after one or more excitatory pulses are provided to the patient's ventricle. In such embodiments, the pacing may be timed without relying on sensing atrial excitation. Optionally, in such embodiments atrial excitation is sensed in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

Figure 10A:
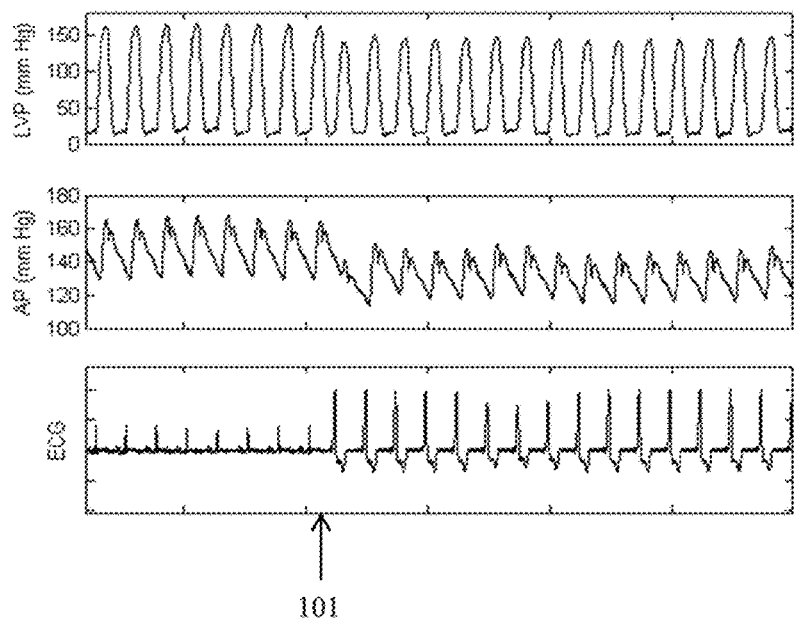
FIG. 10A shows a time plot including: electrocardiogram, aortic pressure and left ventricular pressure of a healthy canine heart.
Figure 10B:
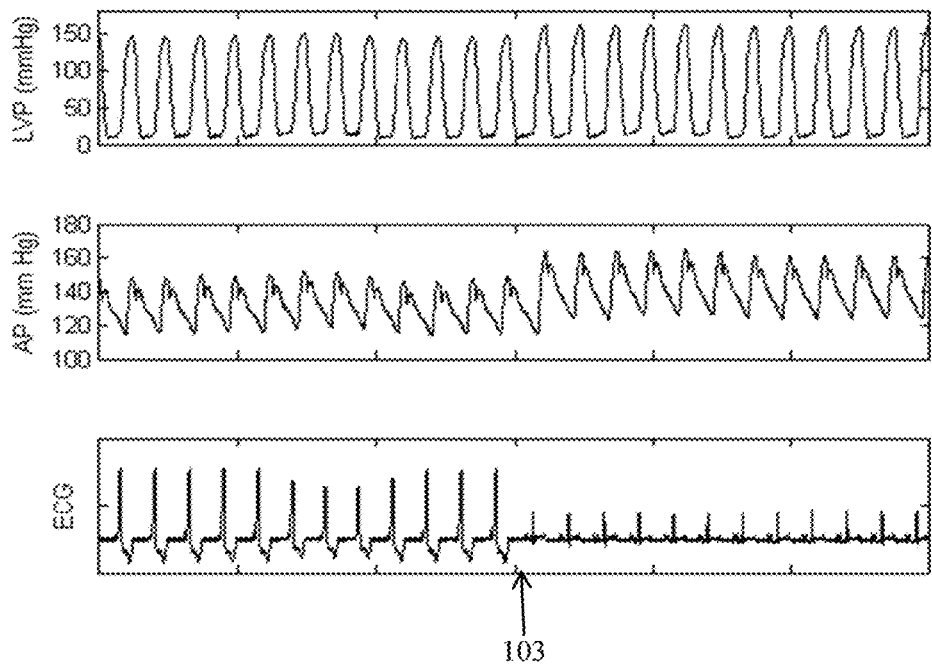
FIG. 10B shows a time plot including: electrocardiogram, aortic pressure and left ventricular pressure of a healthy canine heart.

FIGS. 10A and 10B depict a healthy anesthetized canine heart, showing an electrocardiogram (ECG), left ventricle pressure (LVP) and arterial (blood) pressure (AP) traced over a period of time. In FIG. 10A, before point 101, the heart was allowed to beat naturally, and the ECG, LVP, and AP were traced. At point 101, ventricular pacing commenced. The ventricle was paced 2 ms after the onset of atrial excitation. This pacing caused an immediate change in the ECG, which was concomitant with a reduction of both LVP and AP. The pacing continued at a 2 ms time interval between the onset of atrial contractions and the onset of ventricular pacing until point 103 in FIG. 10B, where pacing ceased. As seen, immediately upon cessation of pacing, the ECG, LVP, and BP all returned essentially to the same values as before pacing.

Figure 11A:
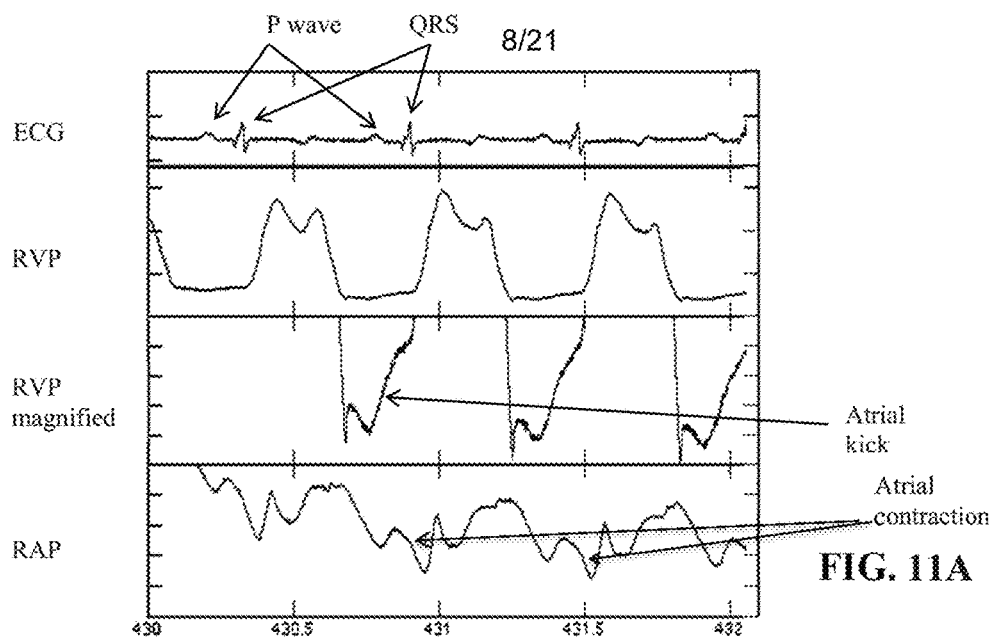
FIG. 11A shows a time plot of a hypertensive canine heart, including right atria pressure, magnified diastolic portion of right ventricular pressure, right ventricular pressure and electrocardiogram.
Figure 11B:
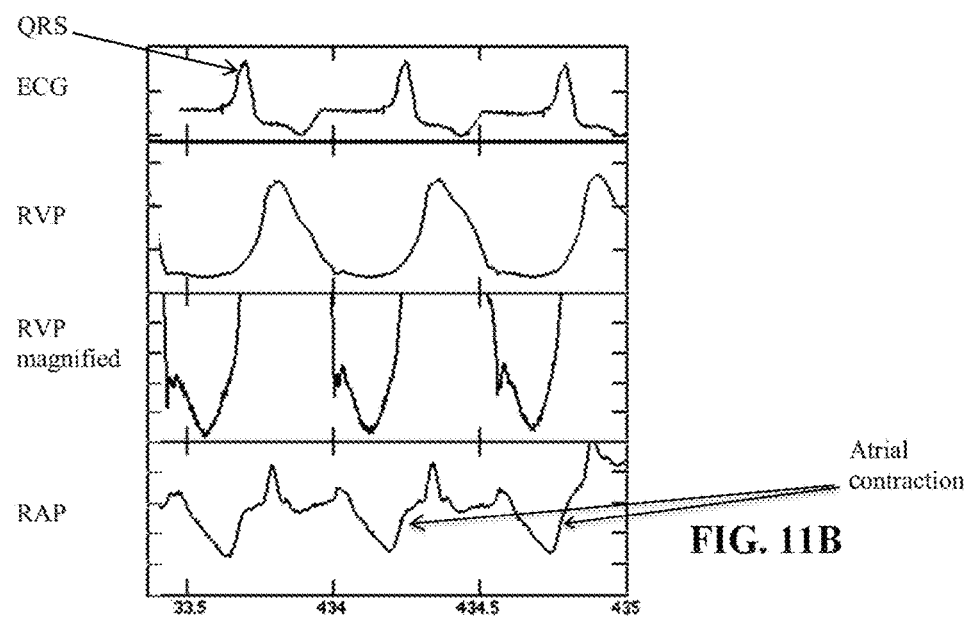
FIG. 11B shows a time plot of a hypertensive canine heart, including right atria pressure, magnified diastolic portion of right ventricular pressure, right ventricular pressure and electrocardiogram.

FIGS. 11A and 11B show a hypertensive canine heart under a natural heartbeat (FIG. 11A) and when paced at a time interval of 2 ms between the onset of atrial contractions and ventricular pacing (FIG. 11B). Each of these figures shows traces of an ECG, right ventricular pressure (RVP), a magnified portion of the RVP, and right atrial pressure (RAP) of the heart.

In FIG. 11A, the P wave and QRS of the natural heartbeat are clearly seen. An increase in atrial pressure is seen following the P wave as a result of atrial contraction. In the RVP trace, a sharp increase in RVP is seen following a QRS complex on the ECG. This is a manifestation of ventricular contraction. When observed at a higher magnification, this sharp increase in RVP is preceded by an earlier, smaller increase in RVP, which coincides with atrial contraction and a reduction in atrial pressure and is a result of blood emptying from the atrium into the chamber. This is the atrial kick. In FIG. 11B, where pacing is at a time interval of 2 ms, the P wave is essentially unnoticeable on the ECG, and an artifact of the electrical stimulator is discernible. The atrial kick in this case is not visible on the magnified trace of right ventricular pressure because the atrial contraction occurred at the same time or even a little after the start of ventricular contraction.

In FIG. 12, a hypertensive canine heart was paced either at a time interval of 60 ms between the pacing of the atria and the pacing of the ventricle (trace portions 105 and 107) or a time interval 120 ms of between atrial and ventricular pacing (trace portion 109). The trace shows the ECG of the heart, left ventricular pressure (LVP), right ventricular pressure (RVP), a magnification of RVP, and right atrial pressure (RAP). As seen in trace portions of RVP magnified corresponding with trace portions 105 and 107, the atrial kick during pacing at the 60 ms time interval is very slight and the contraction of the ventricle begins slightly after the peak of atrial contraction. In this case the contribution of atrial kick to ventricular filling is markedly reduced but not totally eliminated and, on the other end, the peak of atrial contraction does not occur against a closed valve and atrial stretch does not increase. During pacing at a time interval of 120 ms, the atrial kick is clearly seen (portion 109 in trace RVP magnified), but the start of the ventricular contraction and the closure of the AV valve occur before the completion of atrial contraction, thereby slightly reducing the contribution of the atrial kick to ventricular filling.

Figure 16:
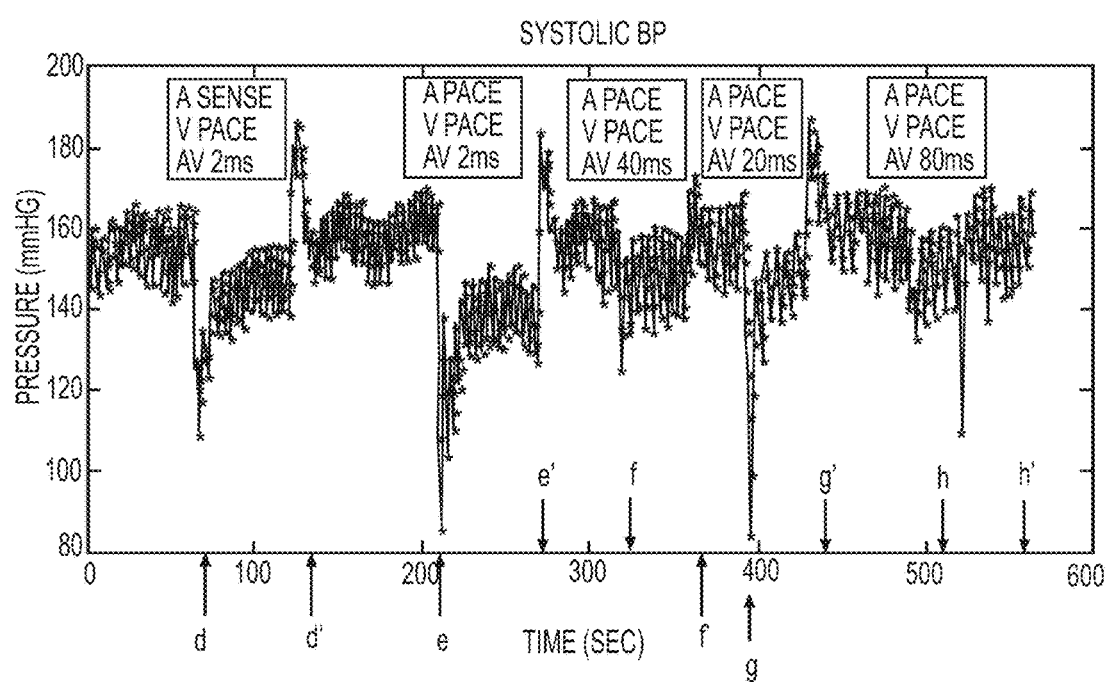
FIG. 16 shows the systolic blood pressure of a hypertensive patient receiving a stimulation signal, plotted against time.

In FIG. 16, the heart of a hypertensive patient was paced with different AV delays. This example shows the results obtained by pacing in both an atrium and a corresponding ventricle versus pacing only the ventricle based on the sensed pulses in the atrium. During interval d-d', atrial pulses were sensed and ventricular pulses were paced with an AV delay of 2 ms. During interval e-e', the atrium and ventricle were both paced with an AV delay of 2 ms. During interval f-f', the atrium and the ventricle were both paced with an AV delay of 40 ms. During interval g-g', the atrium and the ventricle were both paced with an AV delay of 20 ms. During interval h-h', the atrium and the ventricle were both paced with an AV delay of 80 ms. As shown in this example, when comparing interval d-d' with interval e-e', the blood pressure is reduced more when the atrium is paced during interval e-e' than when atrial activity was just sensed. As also shown in this example, when comparing interval e-e', interval f-f', interval g-g', and interval h-h', the shorter AV delays caused more of a reduction in blood pressure than the longer ones. For example, interval g-g' (20 ms AV-delay) shows a higher blood pressure than interval e-e' (2 ms AV-delay). As shown from the results of this example, the changes in blood pressure may be caused at least partially by the different AV delays, which result in different percentages of atrial contraction against a closed valve.

Exemplary Embodiments of Methods for Reducing Atrial Kick

Figure 13:
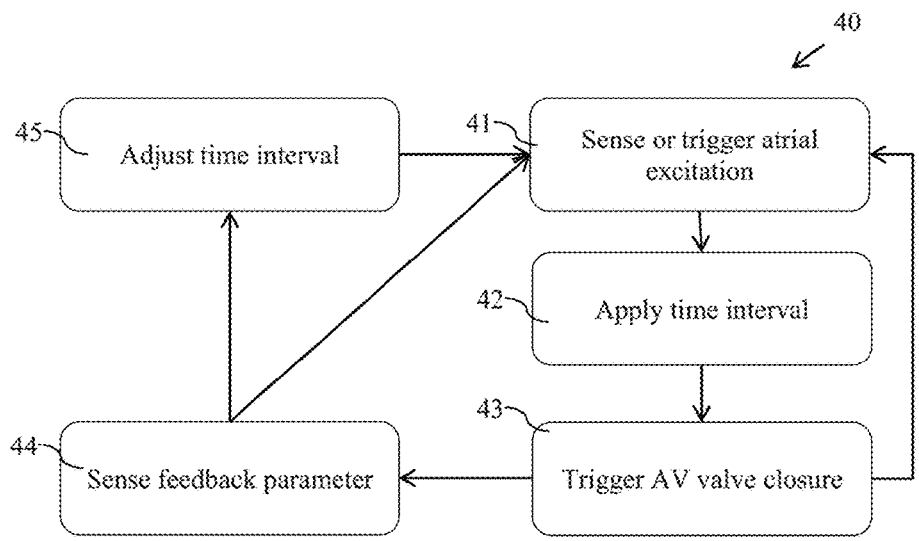
FIG. 13 is a flow chart showing an exemplary method for reducing blood pressure.

An exemplary method 40 for reducing blood pressure is depicted schematically in FIG. 13. Method 40 may be performed by device 50 of FIG. 14, described below. Accordingly, device 50 may be configured to perform any or all steps of method 40. Similarly, method 40 may include any steps device 50 is configured to perform. For example, method 40 may include any of the functions discussed above with respect to device 50. Method 40 may include any steps from method 600. Similarly, method 600 may include any steps from method 40. Method 40 may include any steps that system 700 may be configured to perform. System 700 may be configured to perform any or all steps of method 40.

In some embodiments, method 40 may include a step 41 of atrial excitation. In some embodiments, step 41 includes sensing an atrial excitation. For example, step 41 may include sensing an intrinsic atrial excitation. In some embodiments, step 41 includes triggering atrial excitation. Method 40 may include a step 42 in which a time interval is applied. Method 40 may include a step 43 of triggering AV valve closure. In some embodiments, step 43 may be performed by applying an excitatory current to the at least one ventricle and/or by actuating an artificial valve between the at least one atrium and the corresponding ventricle(s) to close. In some embodiments, step 41, step 42, and step 43 may be repeated as depicted by a return arrow leading back to step 41 from step 43. In some embodiments, an excitatory current may be applied to both ventricles, at the same time or in sequence. In some embodiments, where both ventricles are paced in sequence, the time interval may be measured between the onset of excitation of at least one atrium (e.g., the right atrium) and the onset of excitation of the corresponding ventricle to be paced (e.g., the right ventricle). In some embodiments, where the time interval is set to be zero or negative, step 43 may be performed before or at the same time as step 41. In some embodiments, the time interval may be measured in milliseconds.

Optionally, contraction of the atrium and the ventricle may be caused by controlling both contractions (e.g., by controlling the excitations leading to the contractions). Optionally, the onset of excitation of the atrium is sensed, which sensing triggers the closing of a valve at the prescribed timing interval. Optionally, both atria are paced. In some embodiments, where both AV valves are closed in sequence (e.g., as both ventricles are paced in sequence), the timing interval is measured from the onset of excitation of the first atrium to be paced and the onset of the valve closing or the onset of excitation of at least one ventricle. Optionally the timing of an excitation (e.g., the onset of excitation) of one or more chambers is estimated, for example based on the timing in one or more preceding heart cycles, and one or more excitation stimuli are delivered to the same and/or to a different chamber at a desired time interval before and/or after the estimated timing.

In some embodiments, method 40 may be repeated for every heartbeat. In some embodiments, method 40 may be performed intermittently. For example, the method may be applied once every few heartbeats. Alternatively, method 40 may be applied for a few heartbeats, stopped for one or more heartbeats, and then applied again. For example, method 40 may be applied for 5 to 15 heartbeats, stopped for 2 to 5 heartbeats, and then resumed again. In some embodiments, the pattern of application/avoiding application may be more complex and may be optionally based on a predefined algorithm. For example, an algorithm may adjust parameters of stimulation rather than simply stop and start stimulation. Application of method 40 in some embodiments reduces ventricle filling between heartbeats thereby potentially reducing the ejection profile. As used herein, the ejection profile of a heart is the total amount of blood pumped by the heart in a given period of time. In some embodiments, an intermittent application of method 40 may be applied to counteract a reduction in the ejection profile of the heart.

In some embodiments, the time interval applied in step 42 may be selected based on feedback. In such cases, method 40 may include step 44 of sensing a feedback parameter from one or more of the heart chambers, any portion thereof, and/or the body of the patient. For example, feedback information may be obtained by monitoring directly or indirectly one or more of the atrial kick, blood pressure (e.g., at an artery), ventricular pressure, and/or atrial pressure. In some embodiments, feedback information may additionally or alternatively include the degree of overlap between the time when the atrium contracts and the time when the AV valve is closed and/or the time when the ventricle contracts. For example, an ultrasound sensor may be used to detect cardiac activity, for example, by ultrasound imaging of cardiac activity or by creating an echocardiogram (ECHO). In some embodiments, step 44 may include using an ultrasound sensor to detect the flow of blood (e.g., the velocity of flow) and/or cardiac tissue movement at any arbitrary point using pulsed or continuous wave Doppler ultrasound. Optionally, step 44 may include using an ultrasound sensor to detect an A wave corresponding to the contraction of the left atrium and the flow of blood to the left ventricle.

Method may include a step 45 of adjusting the time interval from step 42 based on the feedback information from step 44. For example, step 45 may include adjusting the time interval based on a sensed blood pressure. As shown by the arrow directed from step 45 to step 41 in FIG. 13, step 41, step 42, step 43, and/or step 44 may be repeated after performing step 45. In some embodiments, the time interval may be initially set at a first value during step 41 and, based on feedback sensing performed during step 44, the time interval may be reduced or increased during step 45 until the feedback value is within a given range (or above or below a given value). For example, the time interval may be adjusted until such time that systolic blood pressure is above 100 mmHg and/or below 140 mmHg and/or diastolic blood pressure is below 90 mmHg and/or above 60 mmHg.

In some embodiments, step 44 and step 45 may be performed during operation of method 40 for every application of step 43 (e.g., application of a ventricular pacing stimulus). In some embodiments, alternatively or additionally, step 44 and step 45 may be performed upon providing a device to a patient (e.g., by implantation of the device) according to one or more embodiments. The adjusting steps may be repeated periodically (for example by a care taker during a checkup) and/or intermittently (for example once an hour or once every few applications of a ventricular pacing stimulus). In some embodiments, step 45 may be performed when feedback information indicates that one or more sensed parameters exceed a preset range for a period of time that exceeds a predefined period.

The steps of method 40 may be performed in any order. For example, the steps may be performed in the order indicated by the arrows shown in FIG. 13. In another embodiment, step 42 may be performed before step 41.

The timing of atrial contraction, atrial excitation, ventricular contraction, closing and/or opening of the AV valve (s), and/or the flow or lack thereof of blood from one or more atria to the respective ventricle(s) and/or blood pressure may be detected by any method known in the art and may be used as feedback control. In some embodiments, the onset of excitation may be used as a trigger for the delivery of an excitatory stimulus to one or more ventricles. The sensed information may be additionally or alternatively be used in the adjusting of a timing interval of the device.

Optionally, feedback parameters may allow responding to conditions that require additional throughput from the heart, and rather than adjust the timing interval they may be used to automatically stop the causing of valve closing at a shortened timing interval. For example, the feedback parameters may lead to an adjustment during exercise. In this example, a heart rate sensor may be used to provide feedback information on the heart rate of the patient. If the heart rate is above a given threshold the feedback may be used to cause the device to stop. The device may be activated again based on sensed feedback information, for example, when the heart rate is below a given threshold and/or after a predetermined period has passed.

Embodiments of Devices for Reducing Blood Pressure

Attention is now drawn to FIG. 14, which schematically depicts an exemplary device 50 according to an embodiment. Device 50 may be constructed and have components similar to a cardiac pacemaker essentially as known in the art with some modifications as discussed herein. Optionally, the device is implantable. Optionally, the device comprises components that may provide additional and/or alternative electrical treatments of the heart (e.g., defibrillation). Device 50 may be configured for implantation in the body of a patient essentially as is known in the art for implantable pacemakers, optionally with some modifications as discussed herein. Device 50 may include any components of system 700 and system 700 may include any components of device 50.

Device 50 may include a biocompatible body 51, one or more controllers 52, a power source 53, and a telemetry unit 56. Body 51 may comprise a housing for encasing a plurality of components of the device. Controller(s) 52 may be configured to control the operation of the device, and may implement any of the embodiments and methods disclosed herein. For example, controller(s) 52 may control the delivery of stimulation pulses. In some embodiments, power source 53 may include a battery. For example, power source 53 may include a rechargeable battery. In some embodiments, power source 53 may include a battery that is rechargeable by induction. In some embodiments, telemetry unit 56 may be configured to communicate with one or more other units and/or components. For example, telemetry unit 56 may be configured to communicate with an external programmer and/or a receiving unit for receiving data recorded on device 50 during operation.

In some embodiments, device 50 may be configured to be attached to one or more electrodes and/or sensors. The electrodes and/or sensors may be integrated in device 50, attached thereto, and/or connectable therewith. In some embodiments, the electrodes may include ventricular electrode(s) 561 configured to pace at least one ventricle. Additionally or alternatively, the device may be connected, optionally via wires or wirelessly, to at least one implanted artificial valve 562. Additionally, device 50 may comprise one or more atrial electrode(s) 57 for pacing one or more atria, and/or one or more atrial sensors 58 for sensing the onset of atrial excitation, and/or one or more sensors 59 for providing other feedback parameters.

In some embodiments, sensor(s) 59 may comprise one or more pressure sensors, electrical sensors (e.g., ECG monitoring), flow sensors, heart rate sensors, activity sensors, and/or volume sensors. Sensor(s) 59 may include mechanical sensors and/or electronic sensors (e.g., ultrasound sensors, electrodes, and/or RF transceivers). In some embodiments, sensor(s) 59 may communicate with device 50 via telemetry.

In some embodiments, ventricular electrode(s) 561 and/or atrial electrode(s) 57 may be standard pacing electrodes. Ventricular electrode(s) 561 may be positioned relative to the heart at positions as known in the art for ventricular pacing. For example, ventricular electrode(s) may be placed in and/or near one or more of the ventricles. In some embodiments, atrial electrode(s) 57 may be placed in and/or near one or more of the atria. In some embodiments, atrial electrode(s) 57 may be attached to the one or more atria at one or more positions selected to provide early detection of atrial excitation or depolarization. For example, in some embodiments, atrial electrode(s) 57 may be attached to the right atrium near the site of the sinoatrial (SA) node.

One position of ventricular electrode(s) 561 may be such that pacing may reduce or minimize the prolongation of QRS when the heart is paced, to reduce or even minimize dyssynchrony. In some embodiments, this position is on the ventricular septum near the Bundle of His. Ventricular electrode(s) 561 may additionally or alternatively be placed on the epicardium of the heart or in coronary veins. More than one electrode can be placed on the ventricles to provide biventricular pacing, optionally to reduce dyssynchrony.

Device 50 may include a pulse generator, or stimulation circuit, configured to deliver a stimulation pulse to at least one cardiac chamber. The pulse generator, or stimulation circuit, may include some or all standard capabilities of a conventional pacemaker. Controller 52 may be configured to control the pulse generator, or stimulation circuit. Atrial sensor(s) 58 (and optionally other electrode sensors configured to sense other heart chambers) may be connected to device 50 via specific circuits that will amplify the electrical activity of the heart and allow sampling and detection of the activation of the specific chamber. Other circuits may be configured to deliver stimulation to a specific electrode to pace the heart, creating propagating electrical activation.

In some embodiments, one or more additional sensors 59 may be placed in and/or on one or more of the atria and/or in and/or on one or more of the ventricles and/or in and/or on one or more other locations that might optionally be adjacent the heart. For example, one or more sensors may be placed on and/or in vena cava and/or on one or more arteries and/or within one or more cardiac chambers. These sensors may measure pressure, or other indicators, such as, for example, impedance and/or flow.

In some embodiments, controller 52 may comprise or be a microprocessor powered by power source 53. In some embodiments, device 50 may comprise a clock 54, for example, generated by a crystal. Device 50 may comprise an internal memory 55 and/or be connected to external memory. For example, device may connect to an external memory via telemetry unit 56. In some embodiments, telemetry unit 56 may be configured to allow communication with external devices such as a programmer and/or one or more of sensors 59. Any and all feedback information and/or a log of device operation may be stored in internal memory 55 and/or relayed by telemetry unit 56 to an external memory unit.

In some embodiments, controller 52 may operate in accordance with at least one embodiment of a method described herein.

In some embodiments, device 50 may comprise one or more sensors for sensing one or more feedback parameters to control the application of the AV delay and/or its magnitude.

Embodiments of Artificial Valves

Additionally or alternatively, device 50 may be configured to directly control the operation of at least one implanted artificial valve 562. Attention is now drawn to FIG. 15, which schematically depicts an artificial valve 60 according to an embodiment of the invention. Valve 60 as depicted in the example is a bi-leaflet, essentially as known in the art for artificial valves. While the following example relates to a bi-leaflet valve it is appreciated that embodiments may be implemented in other artificial valves, for example, caged ball valves and disc valves as well.

Figure 15:
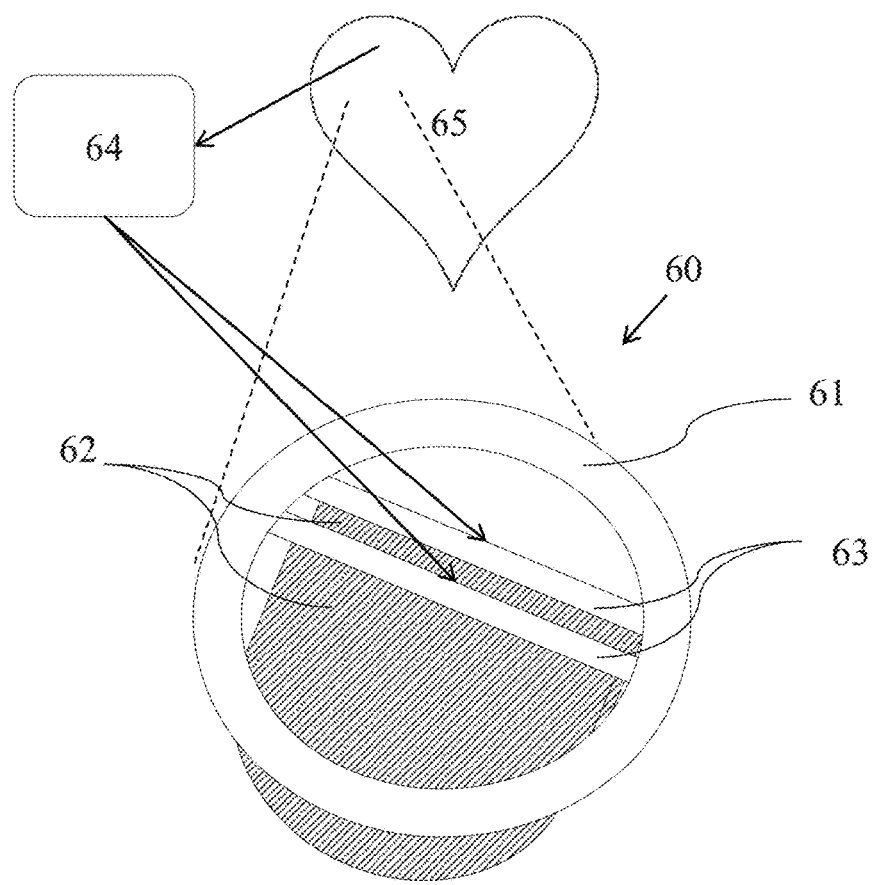
FIG. 15 is a schematic diagram illustrating an artificial valve according to an embodiment.

As shown in FIG. 15, valve 60 may comprise a ring 61 for suturing the valve in place when implanted in a heart of a patient. Valve 60 may include two semicircular leaflets 62 that rotate about struts 63 attached to ring 61. In this schematic representation, other device components are schematically depicted as body 64, which corresponds to body 51 as shown in FIG. 14. Body 64 may receive feedback information from heart 65, in which valve 60 is implanted.

Valve 60 differs from conventional artificial valves in that its closure may be directly controlled by device 50. Valve 60 may comprise a mechanism (for example, a coil or a hydraulic mechanism) that is configured to actively cause closure of the valve (for example, by rotating struts 63 or by inflating a portion of the one or more of leaflets 62). The mechanism may later be brought back to a relaxed position to allow opening of the valve and to allow its repeated closing as needed. The relaxation may be performed at a predetermined time after closing. Additionally or alternatively, relaxation may be affected in response to a sensor reading ventricular activity (e.g., a pressure sensor). Control over valve 60 may be operated wirelessly (using a telemetry unit associated with the valve) or by wired communication with components in body 64. In some embodiments, valve 60 may be a valve configured to be opened and closed independent of fluid pressure acting on the valve. For example, valve 60 may be a ball valve.

Effects of Embodiments for Reducing Blood Pressure

Overall, some embodiments of the disclosed methods and systems provide different approaches to reducing the filling of at least one ventricle, consequently reducing blood pressure. Unlike previous mechanical methods for reducing blood pressure, some embodiments described herein may achieve this goal without increasing pressure within the at least one corresponding atrium. Without an increase in atrial pressure to trigger the secretion of atrial natriuretic hormone, or atrial natriuretic peptide, the reduction of blood pressure can be mechanically controlled. The disclosed embodiments may prevent an unwanted effect on heart rate and may reduce the likelihood of canon atrial waves.

Some of the disclosed embodiments may reduce atrial kick while also increasing atrial stretch, causing the release of atrial natriuretic peptide. For example, disclosed embodiments may comprise a method including a step of stimulating a heart to cause an atrium thereof to contract while a heart valve associated with the atrium is closed such that the contraction distends the atrium. Some embodiments, as described above, may increase atrial pressure and atrial stretch by using cardiac stimulation that reaches maximum atrial pressure resulting from atrial contraction at a period of time overlapping maximum passive increase in atrial pressure, to cause secretion of atrial natriuretic hormone or atrial natriuretic peptide, which may reduce blood pressure are described above. Some embodiments, as described above, may increase atrial pressure and atrial stretch by using cardiac stimulation configured to have an atrium contract such that an atrial pressure resulting from atrial contraction of an atrium overlaps in time a passive pressure build-up of the atrium, thereby providing an atrial pressure of the atrium that is a combination of the atrial pressure resulting from atrial contraction and the passive pressure build-up and is higher than an atrial pressure of the atrium would be without the stimulation, thereby causing increased atrial stretch of the atrium that reduces blood pressure through hormonal or neuronal pathways. Reducing atrial kick and causing the release of atrial natriuretic peptide at the same time may have a synergistic effect on lowering blood pressure. In some embodiments, controlling the timing of valve closure relative to atrial contraction may control the amount one or more atria stretches.

Unlike previous pharmaceutical or mechanical methods for reducing blood pressure, some of the disclosed embodiments achieve the goal of reducing blood pressure immediately. For example, a reduction in blood pressure may occur within 1-3 sec or within 1, 3, or 5 heartbeats of the application of electricity and the blood pressure may reach a minimal blood pressure value within less than 5 heartbeats from the beginning of stimulation.

Examples discussed above strike a balance between mechanical treatment, neuronal feedback, and the natural release of hormones that cause adaptation. The mechanical treatment and the natural release of hormones may be additive or even synergistic mechanisms. The hormonal release affects the cardiovascular system while the mechanical treatment affects the heart itself. Intermittently delivering the mechanical treatment to reduce blood pressure may affect both the neuronal and hormonal feedback controlling the cardiovascular system and reduce adaptation.

The headings used in this specification are only meant to aid in organization and do not define any terms.

The present disclosure is related to the following applications, all of which are herein incorporated by reference in their entirety:

U.S. Patent Application Publication Number 2012/0215272 to Levin et al., published on Aug. 23, 2012, now U.S. Pat. No. 8,521,280, issued Aug. 27, 2013;

U.S. Patent Application Publication Number 2011/0172731 to Levin et al., published on Jul. 14, 2011, now U.S. Pat. No. 8,515,536, issued Aug. 20, 2013;

U.S. Patent Application Publication Number 2013/0331901 to Levin et al., published on Dec. 12, 2013; and U.S. Patent Application Publication Number 2012/0041502 to Schwartz et al., published on Feb. 16, 2012, now U.S. Pat. No. 8,428,729, issued Apr. 23, 2013.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A system for reducing blood pressure in a patient, the system comprising:
   a stimulation circuit configured to deliver a stimulation pulse to at least one cardiac chamber of a heart of the patient; and
   at least one controller configured to execute the delivery of one or more stimulation patterns of stimulation pulses to the at least one cardiac chamber,
   wherein at least one of the stimulation pulses stimulates the heart such that an atrial pressure resulting from atrial contraction of an atrium overlaps in time a passive pressure build-up of the atrium, such that an atrial pressure of the atrium resulting from the stimulation is a combination of the atrial pressure resulting from atrial contraction and the passive pressure build-up and is higher than an atrial pressure of the atrium would be without the stimulation, and such that the blood pressure of the patient is reduced.

2. The system of claim 1, wherein the atrial pressure of the atrium resulting from the stimulation causes an increased atrial stretch of the atrium that reduces blood pressure through hormonal and/or neural pathways.

3. The system of claim 1, wherein the passive pressure build-up of the atrium occurs during isovolumic contraction of a ventricle of the heart.

4. The system of claim 3, wherein the passive pressure build-up of the atrium occurs during a rapid ejection phase of the ventricle.

5. The system of claim 1, wherein the at least one of the stimulation pulses stimulates the heart such that a maximum of atrial pressure resulting from atrial contraction of an atrium overlaps in time a maximum passive pressure build-up of the atrium.

6. The system of claim 5, wherein the maximum passive pressure build-up of the atrium occurs at a time between about 25 ms after start of an isovolumic phase and about 10 ms after end of the isovolumic phase.

7. The system of claim 5, wherein the maximum passive pressure build-up of the atrium occurs between a start of a second half of an isovolumic phase and a first approximately 10 ms of a rapid ejection phase.

8. The system of claim 1, wherein the at least one of the stimulation pulses comprises stimulating a ventricle of the heart and/or stimulating the atrium of the heart.

9. The system of claim 1, wherein the at least one of the stimulation pulses comprises stimulating a ventricle of the heart and the atrium.

10. The system of claim 9, wherein the one or more stimulation patterns comprise pacing the atrium and the ventricle at a substantially equal rate.

11. The system of claim 9, wherein the one or more stimulation patterns comprise pacing the atrium at a rate higher than a rate at which the ventricle is paced.

12. The system of claim 1, wherein the at least one of the stimulation pulses comprises stimulating the atrium of the heart such that the atrium contracts only once during a single cardiac cycle.

13. The system of claim 1, wherein the at least one of the stimulation pulses comprises pacing the atrium of the heart and/or a ventricle of the heart, such that a relative timing of excitation corresponds to an atrioventricular delay of between approximately 60 ms and approximately 0 ms.

14. A method, carried out with an implanted heart muscle stimulator associated with a heart of a patient, for reducing blood pressure of the patient, the method comprising:
   stimulating the heart to provide an atrial pressure resulting from atrial contraction that overlaps in time a passive pressure build-up of the atrium, such that the overlapping atrial pressure resulting from the atrial contraction and passive pressure build-up elicits an atrial pressure that is a combination of the atrial pressure resulting from atrial contraction and the passive pressure build-up and is higher than an atrial pressure of the atrium would be without the stimulation, and such that the blood pressure of the patient is reduced.

15. The method of claim 14, wherein the atrial pressure of the atrium resulting from the stimulation of the heart causes an increased atrial stretch of the atrium that reduces blood pressure through hormonal and/or neuronal pathways.

16. The method of claim 14, wherein the passive pressure build-up of the atrium occurs during isovolumic contraction of a ventricle of the heart.

17. The method of claim 16, wherein the passive pressure build-up of the atrium occurs during a rapid ejection phase of the ventricle.

18. The method of claim 14, wherein stimulating the heart comprises stimulating the heart such that a maximum of atrial pressure resulting from atrial contraction of an atrium overlaps in time a maximum passive pressure build-up of the atrium.

19. The method of claim 18, wherein the maximum passive pressure build-up of the atrium occurs at a time between about 25 ms after start of an isovolumic phase and about 10 ms after end of the isovolumic phase.

20. The method of claim 18, wherein the maximum passive pressure build-up of the atrium occurs between a start of a second half of an isovolumic phase and a first approximately 10 ms of a rapid ejection phase.

21. The method of claim 14, wherein stimulating the heart comprises stimulating the atrium of the heart and/or stimulating a ventricle of the heart.

22. The method of claim 21, further comprising pacing the atrium and the ventricle at a substantially equal rate.

23. The method of claim 21, further comprising pacing the atrium at a rate higher than a rate at which the ventricle is paced.

24. The method of claim 14, further comprising stimulating the atrium such that the atrium contracts only once during a single cardiac cycle.

25. The method of claim 14, further comprising pacing the atrium of the heart and/or a ventricle of the heart, such that a relative timing of excitation corresponds to an atrioventricular delay of between approximately 60 ms and approximately 0 ms.

26. A system for reducing blood pressure comprising:
 means for providing information about pressure variation in an atrium during at least one cardiac cycle of a heart of a patient;
 means for generating stimulation pulses; and
 means for applying the stimulation pulses to at least one cardiac chamber of the heart of the patient,
 wherein the means for generating stimulation pulses are arranged to generate the stimulation pulses so as to control the timing of an atrial contraction relative to the timing of a ventricular contraction in a single cardiac cycle according to the information about pressure variation in the atrium.

27. The system of claim 26, wherein the information about pressure variation comprises information about occurrence of an atrial contraction and/or information about occurrence of a ventricular contraction.

28. The system of claim 27, wherein the means for generating stimulation pulses are arranged for generating for at least one cardiac cycle:
 at least one atrial stimulation pulse for generating an atrial contraction; and/or
 at least one ventricular stimulation pulse for generating a ventricular contraction.

29. The system of claim 28, wherein the means for generating stimulating pulses are arranged:
 for generating the at least one atrial stimulation pulse, on the basis of the information about the occurrence of the atrial contraction and/or the information about the occurrence of the ventricular contraction, in a timed relationship to the occurrence of the atrial contraction and/or to the occurrence of the ventricular contraction; and/or
 for generating the at least one ventricular stimulation pulse, on the basis of the information about the occurrence of the ventricular contraction and/or the information about the occurrence of the atrial contraction, in a timed relationship to the occurrence of the ventricular contraction and/or to the occurrence of the atrial contraction.

30. The system of claim 28, wherein the information about the occurrence of the atrial contraction includes information about occurrence of a P wave pattern in a natural stimulation pattern of a cardiac cycle.

31. The system of claim 28, wherein the information about the occurrence of the ventricular contraction includes information about occurrence of a QRS complex in a natural stimulation pattern of a cardiac cycle.

32. The system of claim 26, wherein the means for generating stimulation pulses are arranged to generate one or more stimulation patterns of the stimulation pulses,
 wherein at least one of the stimulation pulses stimulates the heart such that an atrial pressure resulting from atrial contraction of the atrium overlaps in time a passive pressure build-up of the atrium occurring during isovolumic contraction of a ventricle of the heart, such that an atrial pressure of the atrium resulting from the stimulation is a combination of the atrial pressure resulting from atrial contraction and the passive pressure build-up and is higher than an atrial pressure of the atrium would be without the stimulation, and such that the blood pressure of the patient is reduced, and
 wherein the one or more stimulation patterns comprise stimulating the heart such that atrial kick is reduced and/or prevented.

33. The system of claim 26, wherein the means for generating stimulation pulses are arranged to generate one or more stimulation patterns of the stimulation pulses,
 wherein the one or more stimulation patterns comprise alternating between a plurality of stimulation patterns having a different ratio of:
 first stimulation pulses that stimulate the heart such that an atrial pressure resulting from atrial contraction of an atrium overlaps in time a passive pressure build-up of the atrium occurring during isovolumic contraction of a ventricle of the heart, such that an atrial pressure of the atrium resulting from the stimulation is a combination of the atrial pressure resulting from atrial contraction and the passive pressure build-up and is higher than an atrial pressure of the atrium would be without the stimulation, and
 second stimulation pulses that do not provide an atrial pressure resulting from atrial contraction of an atrium that overlaps in time a passive pressure build-up of the atrium.

34. A system for reducing blood pressure in a patient, the system comprising:
 means for providing information about timing of one or more heart activity events, the information comprising information about at least one of:
 contraction of an atrium,
 contraction of a ventricle,
 opening of an atrioventricular valve,
 closure of an atrioventricular valve,
 electrical activity of the atrium,
 electrical activity of the ventricle,
 blood flow,
 atrial pressure of the atrium,
 changes in atrial pressure of the atrium,
 a refractory period of an atrium, or
 heart rate;
 means for generating stimulation pulses; and
 means for applying the stimulation pulses to at least one cardiac chamber of a heart of a patient, wherein the means for generating stimulation pulses are arranged to generate the stimulation pulses so as to set a timing of atrial contraction relative to ventricular contraction based on the information.

35. The system of claim 34, wherein the timing of atrial contraction relative to ventricular contraction corresponds to an atrioventricular delay within a range of about 60 ms to about 0 ms.

36. The system of claim 34, wherein the means for generating stimulation pulses are arranged to generate the stimulation pulses so as to:
provide an excitatory stimulus to the atrium within a range of about 60 ms to about 0 ms before ventricular excitation occurs;
provide an excitatory stimulus to the ventricle within a range of about 60 ms to about 0 ms after atrial excitation occurs; and/or
provide an excitatory stimulus to the atrium and then within a range of about 60 ms to about 0 ms later provide an excitatory stimulus to the ventricle.

37. The system of claim 34, wherein the information about timing of one or more heart activity events includes information about timing between two or more heart activity events in a single cardiac cycle.

38. The system of claim 34, wherein the means for generating stimulation pulses are arranged for generating for at least one cardiac cycle:
at least one atrial stimulation pulse for generating an atrial contraction; and/or
at least one ventricular stimulation pulse for generating a ventricular contraction.

39. The system of claim 38, wherein the means for generating stimulating pulses are arranged:
for generating the at least one atrial stimulation pulse, on the basis of the information about the contraction of the atrium and/or the information about the contraction of the ventricle, in a timed relationship to the contraction of the atrium and/or to the contraction of the ventricle; and/or
for generating the at least one ventricular stimulation pulse, on the basis of the information about the contraction of the ventricle and/or the information about the contraction of the atrium, in a timed relationship to the contraction of the ventricle and/or to the contraction of the atrium.

40. The system of claim 38, wherein the information about the contraction of the atrium includes information about occurrence of a P wave pattern in a natural stimulation pattern of a cardiac cycle.

41. The system of claim 38, wherein the information about the contraction of the ventricle includes information about occurrence of a QRS complex in a natural stimulation pattern of a cardiac cycle.

42. The system of claim 34, wherein the means for generating stimulation pulses are arranged to generate the stimulation pulses so as to cause the atrium to commence contraction about 60 ms or less before closure of the atrioventricular valve.

43. The system of claim 34, wherein the means for generating stimulation pulses are arranged to generate the stimulation pulses so as to start contraction of the atrium about 60 ms or less before start of passive pressure build-up in the atrium, and thereby combine atrial pressure due to atrial contraction with atrial pressure due to passive pressure build-up to yield an increased atrial pressure.

44. The system of claim 34, wherein the means for generating stimulation pulses are arranged to generate the stimulation pulses so as to start contraction of the atrium about 60 ms or less before start of contraction of the ventricle.

45. The system of claim 34, wherein the means for generating stimulation pulses, in generating the stimulation pulses, are arranged to take into account a delay between actual onset of excitation and sensing of the excitation.

46. The system of claim 45, wherein the means for generating stimulation pulses estimates the delay by:
using a time difference between a first atrioventricular delay measured when both the atrium and the ventricle are sensed and a second atrioventricular delay when the atrium is paced and the ventricle is sensed; and/or
calculating amplifier response time based on a set threshold, a signal strength, and a frequency content; and/or
modifying a delay used with atrial sensing until an effect on blood pressure is the same as an effect on blood pressure obtained by pacing both the atrium and the ventricle with a desired atrioventricular delay.

47. The system of claim 34, wherein the means for generating stimulation pulses, in generating the stimulation pulses, takes into account a delay between electrical activation of a cardiac chamber and occurrence of a corresponding mechanical contraction.

48. The system of claim 34, wherein the means for generating stimulation pulses are arranged to generate one or more stimulation patterns of the stimulation pulses,
wherein at least one of the stimulation pulses stimulates the heart such that an atrial pressure resulting from atrial contraction of the atrium overlaps in time a passive pressure build-up of the atrium occurring during isovolumic contraction of the ventricle, such that an atrial pressure of the atrium resulting from the stimulation is a combination of the atrial pressure resulting from atrial contraction and the passive pressure build-up and is higher than an atrial pressure of the atrium would be without the stimulation, and such that the blood pressure of the patient is reduced, and
wherein the one or more stimulation patterns comprise stimulating the heart such that atrial kick is reduced and/or prevented.

49. The system of claim 34, wherein the means for generating stimulation pulses are arranged to generate one or more stimulation patterns of the stimulation pulses,
wherein the one or more stimulation patterns comprise alternating between a plurality of stimulation patterns having a different ratio of:
first stimulation pulses that stimulate the heart such that an atrial pressure resulting from atrial contraction of an atrium overlaps in time a passive pressure build-up of the atrium occurring during isovolumic contraction of the ventricle, such that an atrial pressure of the atrium resulting from the stimulation is a combination of the atrial pressure resulting from atrial contraction and the passive pressure build-up and is higher than an atrial pressure of the atrium would be without the stimulation, and
second stimulation pulses that do not provide an atrial pressure resulting from atrial contraction of an atrium that overlaps in time a passive pressure build-up of the atrium.

50. The system of claim 34, wherein the means for generating stimulation pulses are arranged to generate one or more stimulation patterns of the stimulation pulses,
wherein the one or more stimulation patterns comprise alternating between:

a first period of stimulation pulses that stimulate the heart such that an atrial pressure resulting from atrial contraction of an atrium overlaps in time a passive pressure build-up of the atrium occurring during isovolumic contraction of the ventricle, such that an atrial pressure of the atrium resulting from the stimulation is a combination of the atrial pressure resulting from atrial contraction and the passive pressure build-up and is higher than an atrial pressure of the atrium would be without the stimulation, and a second period of natural heartbeats without stimulation.

51. The system of claim 34, wherein the means for generating pulses is configured to adjust parameters of the stimulation pulses based on sensing of a feedback parameter of the body of the patient.

* * * * *